(12) United States Patent
Koser

(10) Patent No.: US 9,999,855 B2
(45) Date of Patent: Jun. 19, 2018

(54) MICROFLUIDIC PROCESSING OF TARGET SPECIES IN FERROFLUIDS

(75) Inventor: Hur Koser, Glastonbury, CT (US)

(73) Assignee: YALE UNIVERSITY, New Haven, CT (US)

( * ) Notice: Subject to any disclaimer, the term of this patent is extended or adjusted under 35 U.S.C. 154(b) by 1117 days.

(21) Appl. No.: 13/882,013

(22) PCT Filed: Jun. 7, 2011

(86) PCT No.: PCT/US2011/039516
§ 371 (c)(1),
(2), (4) Date: Aug. 6, 2013

(87) PCT Pub. No.: WO2012/057878
PCT Pub. Date: May 3, 2012

(65) Prior Publication Data
US 2013/0313113 A1 Nov. 28, 2013

Related U.S. Application Data

(60) Provisional application No. 61/407,738, filed on Oct. 28, 2010.

(30) Foreign Application Priority Data

Dec. 7, 2010 (WO) ................ PCT/US2010/059270

(51) Int. Cl.
*G01N 21/00* (2006.01)
*B01D 57/02* (2006.01)
(Continued)

(52) U.S. Cl.
CPC ........ *B01D 57/02* (2013.01); *B01L 3/502753* (2013.01); *B01L 3/502761* (2013.01);
(Continued)

(58) Field of Classification Search
CPC ............ B01D 57/02; B01L 2200/0652; B01L 2300/0816; B01L 2400/0415;
(Continued)

(56) References Cited

U.S. PATENT DOCUMENTS 3,764,540 A 10/1973 Khalafalla et al.
5,194,133 A 3/1993 Clark et al.
(Continued)

FOREIGN PATENT DOCUMENTS

WO 2006/004558 A1 1/2006
WO WO 2006/004588 1/2006

OTHER PUBLICATIONS

Dittrich et al., "Lab-on-a-chip: microfluidics in drug discovery," 2006, *Nature Reviews Drug Discovery*, vol. 5, pp. 210-218.
(Continued)

*Primary Examiner* — Xiaoyun R Xu
(74) *Attorney, Agent, or Firm* — Riverside Law LLP

(57) ABSTRACT

Disclosed are systems, devices, methods, and other implementations, including a device to detect at least one target species in a sample, with the device including a microfluidic channel configured to receive the sample containing the at least one target species and a biocompatible ferrofluid in which the at least one target species is suspended, a detector to determine the at least one target species in the sample, and at least two of electrodes positioned proximate the microfluidic channel, the at least two electrodes configured to generate controllable magnetic forces in the sample containing the ferrofluid when a controllable at least one electrical current is applied to the at least two electrodes. The generated controllable magnetic forces causes the at least one target species to be directed towards the detector. Also
(Continued)

disclosed are devices for separating target species in a ferrofluid, and for focusing target species suspended in a ferrofluid.

14 Claims, 26 Drawing Sheets

(51) Int. Cl.
| | |
|---|---|
| B01L 3/00 | (2006.01) |
| B03C 1/033 | (2006.01) |
| B03C 1/253 | (2006.01) |
| B03C 1/28 | (2006.01) |
| G01N 15/14 | (2006.01) |
| G01N 27/447 | (2006.01) |
| B03C 1/32 | (2006.01) |

(52) U.S. Cl.
CPC ............ *B03C 1/0335* (2013.01); *B03C 1/253* (2013.01); *B03C 1/288* (2013.01); *B03C 1/32* (2013.01); *G01N 15/1404* (2013.01); *G01N 27/44786* (2013.01); *B01L 2200/0652* (2013.01); *B01L 2300/0816* (2013.01); *B01L 2400/043* (2013.01); *B01L 2400/0415* (2013.01); *B03C 2201/18* (2013.01); *B03C 2201/24* (2013.01); *B03C 2201/26* (2013.01)

(58) Field of Classification Search
CPC ......... B01L 2400/043; B01L 3/502753; B01L 3/502761; B03C 1/0335; B03C 1/24; B03C 1/253; B03C 1/288; B03C 2201/18; B03C 2201/24

See application file for complete search history.

(56) References Cited

U.S. PATENT DOCUMENTS

| | | | |
|---|---|---|---|
| 6,663,757 | B1 | 12/2003 | Führ et al. |
| 2003/0159999 | A1 | 8/2003 | Oakey et al. |
| 2003/0235504 | A1 | 12/2003 | Lemoff et al. |
| 2004/0018611 | A1 | 1/2004 | Ward et al. |
| 2007/0125941 | A1 | 6/2007 | Lee et al. |
| 2007/0134809 | A1 | 6/2007 | Cho et al. |
| 2007/0196820 | A1 | 8/2007 | Kapur et al. |
| 2007/0215553 | A1 | 9/2007 | Yellen et al. |
| 2008/0255006 | A1 | 10/2008 | Wang et al. |
| 2008/0302732 | A1 | 12/2008 | Soh et al. |
| 2009/0035838 | A1 | 2/2009 | Quake et al. |
| 2009/0050569 | A1 | 2/2009 | Jung et al. |
| 2009/0220932 | A1 | 9/2009 | Ingber et al. |

OTHER PUBLICATIONS

Beyor et al., "Immunomagnetic bead-based cell concentration microdevice for dilute pathogen detection," 2008, *Biomedical Microdevices*, vol. 10, pp. 909-917.
Kamei et al., "Microfluidic Genetic Analysis with an Integrated a-Si:H detector," 2005, *Biomedical Microdevices*, vol. 7, pp. 147-152.
Cheong et al., "Gold nanoparticles for one step DNA extraction and real-time PCR of pathogens in a single chamber," 2008, *Lab on a Chip*, vol. 8, pp. 810-813.
Ashkin et al., "Optical trapping and manipulation of single cells using infrared laser beams," 1987, *Nature*, vol. 330, pp. 769-771.
Chiou et al., "Massively parallel manipulation of single cells and microparticles using optical images," 2005, *Nature*, vol. 436, pp. 370-372.
Hughes et al., "Strategies for dielectrophoretic separation in laboratory-on-a-chip systems," 2002, *Electrophoresis*, vol. 23, pp. 2569-2582.

Lee et al., "Microelectromagnets for the control of magnetic nanoparticles," 2001, *Applied Physics Letters*, vol. 79, pp. 3308-3310.
Yan et al., "Near-field-magnetic-tweezer manipulation of single DNA molecules," 2004, *Physical Review E*, vol. 70, pp. 011905.
Davis et al., "Deterministic hydrodynamics: Taking blood apart," 2006, *Proceedings of the National Academy of Sciences of the United States of America*, vol. 103, pp. 14779-14784.
Dufresne et al., "Optical tweezer arrays and optical substrates created with diffractive optics," 1998, *Review of Scientific Instruments*, vol. 69, pp. 1974-1977.
Kremser et al., "Capillary electrophoresis of biological particles: Viruses, bacteria, and eukaryotic cells," 2004, *Electrophoresis*, vol. 25, pp. 2282-2291.
Cabrera et al., "Continuous concentration of bacteria in a microfluidic flow cell using electrokinetic techniques," 2001, *Electrophoresis*, vol. 22, pp. 355-362.
Liu et al., "Evidence for localized Cell Heating induced by Infrared Optical Tweezers," 1995, *Biophysical Journal*, vol. 68, pp. 2137-2144.
Ashkin et al., "Optical Trapping and Manipulation of Viruses and Bacteria," 1987, *Science*, vol. 235, pp. 1517-1520.
Applegate et al., "Optical trapping, manipulation, and sorting of cells and colloids in microfluidic systems with diode laser bars," 2004, *Optical Express*, vol. 12, pp. 4390-4398.
Pethig et al., "Applications of dielectrophoresis in biotechnology," 1997, *Trends in Biotechnology*, vol. 15, pp. 426-432.
Menachery et al., "Controlling cell destruction using dielectrophoretic forces," 2005, *NanoBiotechnology*, vol. 152, pp. 145-149.
Muller et al., "The potential of Dielectrophoresis for Single-Cell Experiments," 2003, *IEEE Engineering in Medicine and Biology Magazine*. vol. 22, pp. 51-61.
Sebastian et al., "Formation of multilayer aggregates of mammalian cells by dielectrophoresis," 2006, *Journal of Micromechanics and Microengineering*, vol. 16, pp. 1769-1777.
Gijs, "Magnetic bead handling on-chip: new opportunities for analytical applications," 2004, *Microfluidics and Nanofluidics*, vol. 1, pp. 22-40.
Kim et al., "Synthesis of ferrofluid with magnetic nanoparticles by sonochemical method for MRI contrast agent," 2005, *Journal of Magnetism and Magnetic Materials*, vol. 289, pp. 328-330.
Scherer et al., "Ferrofluids: Properties and Applications," 2005, *Brazilian Journal of Physics*, vol. 45, pp. 718-727.
Kashevsky et al., "Nonmagnetic particles in magnetic fluid: Reversal dynamics under rotating field," 1997, *Physics of Fluids*, vol. 9, pp. 1811-1818.
Rosensweig RE (1997) *Ferrohydrodynamics* (Dover, New York).
Odenbach S (2002) *Ferrofluids: Magnetically Controllable Fluids and Their Applications* (Springer, New York).
Yellen et al., "Arranging matter by magnetic nanoparticle assemblers," 2005, *Proceedings of the National Academy of Sciences of the United States of America*, vol. 102, pp. 8860-8864.
Mao et al., "Towards ferrofluidics for μ-TAS and lab on-a-chip applications," 2006, *Nanotechnology*, vol. 17, pp. 34-47.
Zahn et al., "Ferrohydrodynamic pumping in spatially uniform sinusoidally time-varying magnetic fields," 1995, *Journal of Magnetism and Magnetic Materials*, vol. 149, pp. 165-173.
Happel J, Brenner H (1983) "*Low Reynolds Number Hydrodynamics*."
Goldman et al., "Slow viscous motion of a sphere parallel to a plane wall-I Motion through a quiescent fluid," 1967, *Chemical Engineering Science*, vol. 22, pp. 637-651.
Ise, "When, why, and how does like like like?—Elecrostatic attraction between similarly charged species," 2007, *Proceedings of the Japan Acadmy. Series B, Physical and Biological Sciences*, vol. 83, pp. 192-198.
Massart, "Preparation of Aqueous Magnetic Liquids in Alkaline and Acidic Media," 1981, *IEEE Transactions on Magnetics*, vol. 17, pp. 1247-1248.
Fischer et al., "Ferro-microfluidic device for pathogen detection," 2008, *IEEE International Conference on Nano/Micro Engineered and Molecular Systems China*, pp. 907-910.

(56) References Cited

OTHER PUBLICATIONS

Maiorov, "Experimental Study of the Permeability of a ferrofluid in an alternating magnetic field," 1979, *Magnetohydrodynamics*, vol. 15, 135-139.
Horan et al., "Stable cell membrane labeling," 1989, *Nature*, vol. 340, pp. 167-168.
Green, "The Sigma-Aldrich Handbook of Stains, Dyes & Indicators," 1990, Aldrich Chemical Co. (Milwaukee, WI), pp. 721-722.
Bautista et al., "Comparative study of ferrofluids based on dextra-coated iron oxide and metal nanoparticles for contrast agents in magnetic resonance imaging," 2004, *Nanotechnology*, Vo. 15, pp. S154-S159.
Tung et al., "Magnetic properties of ultrafine cobalt ferrite particles," 2003, *Journal of Applied Physics*, vol. 93, pp. 7486-7488.
Blattner et al., "The complete genome sequence of *Escherichia coli* K-12," 1997, *Science*, vol. 277, pp. 1453-1474.
Lekka et al., "Elasticity of normal and cancerous human bladder cells studies by scanning force microscopy," 1999, *European Biophysics Journal*, vol. 28, pp. 312-316.
Kose et al., "Towards Ferro-microfluidics for Effective and Rapid Cellular Manipulation and Sorting," 2008, *Proceedings of the 3$^{rd}$ IEEE International Conference on Nano/Micro Engineered and Molecular Systems*, Jan. 6-9, China, pp. 903-906 (especially p. 903, col. 2, para 6; p. 904, col. 1, para 1; p. 905, col. 1, para 1; p. 906, col. 2, para 1; Fig. 3; Fig.4a; Fig. 4b).
International Search Report and Written Opinion of the International Searching Authority for International Application No. PCT/US2010/059270, dated Feb. 8, 2011; (8 pgs.).
Kose et al., "Label-free cellular manipulation and sorting via biocompatible ferrofluids," Dec. 22, 2009, *Proceedings of the National Academy of Sciences of the United States of America*, vol. 106, No. 51, pp. 21478-21483.
Ayse R. Kose et al., "Label-free cellular manipulation and sorting via biocompatible ferrofluids", Proc. Natl. Acad. Sci. USA., Dec. 22, 2009, vol. 106, No. 51, pp. 21478-21483.
International Search Report of PCT/US2011/039516, dated Oct. 18, 2011.
Kose, et al., "Supporting Information to Label-free Cellular Manipulation and Sorting via Biocompatible Ferrofluids," Proceedings of the National Academy of Sciences, USA, Dec. 7, 2009, Retrieved from the Internet: http://www.pnas.org/content/suppl/2009/12/07/0912138106.DCSupplemental/Appendix_PDF.pdf (Retrieved Dec. 4, 2017).

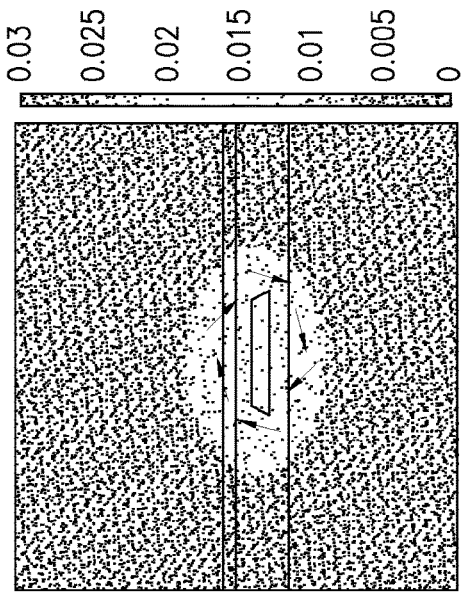
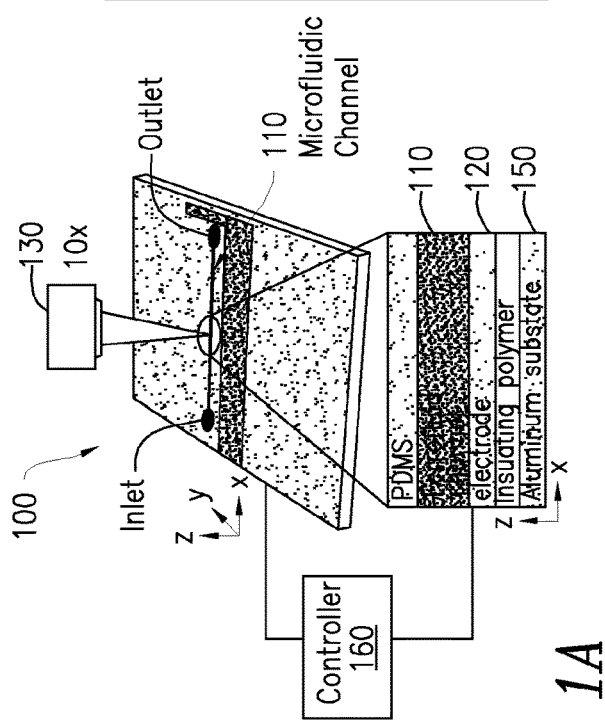
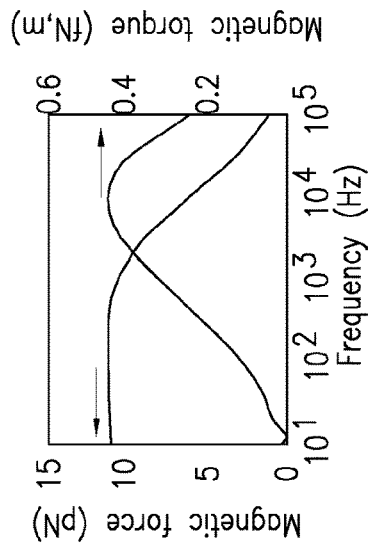
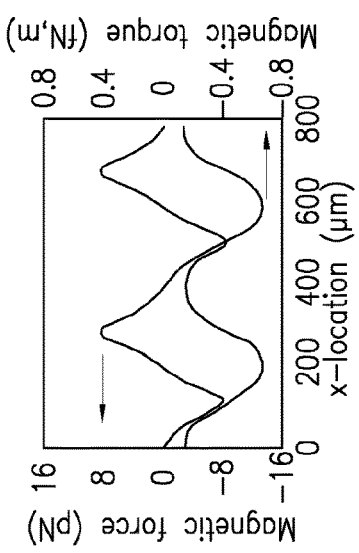
FIG. 1A
FIG. 1B
FIG. 1C
FIG. 1D

Focusing cells for separation and counting

MICROFLUIDIC PROCESSING OF TARGET SPECIES IN FERROFLUIDS

CROSS-REFERENCE TO RELATED APPLICATIONS

This application is a 35 U.S.C. § 371 national stage entry of PCT/US2011/039516, which has an international filing date of Jun. 7, 2011 which claims priority to PCT application No. PCT/US10/59270, entitled "Label-Free Cellular Manipulation and Sorting Via Biocompatible Ferrofluids," and filed Dec. 7, 2010, and to U.S. provisional application Ser. No. 61/267,163, filed Dec. 7, 2009, and 61/407,738, filed Oct. 28, 2010, the contents of all of which are hereby incorporated by reference it their entireties.

FIELD

This disclosure relates generally to microfluidic processing of ferrofluids, including ferrofluids containing a plurality of target species (such as biological target species). More particularly, the disclosure is directed to devices, systems, and methods to perform such operations as separating a plurality of target species in a biocompatible ferrofluid, focusing target species in a biocompatible ferrofluid, detecting target species in a sample, etc.

BACKGROUND

Early diagnosis of diseases involving rare cells in blood (such as metastatic cancer or low-level bacteremia) and accurate monitoring of certain genetic conditions (such as sickle cell anemia) require rapid and accurate separation, sorting, and direction of target cell types toward a sensor surface. In that regard, cellular manipulation, separation, and sorting are increasingly finding application potential within various bioassays in the context of cancer diagnosis (Dittrich et al., 2006, *Nat Rev Drug Discovery* 5:210-218), pathogen detection (Beyor et al., 2008, *Blamed Microdevices* 10:909-917), and genomic testing (Kamei et al. 2005, *Biomed Microdevices* 7:147-152; Cheong et al., 2008, *Lab Chip* 8:810-813).

A variety of contactless micromanipulation methods exist, including optical tweezers (Ashkin et al., 1987, *Nature* 330:769-771; Chian et al., 2005, *Nature* 436:370-372), dielectrophoresis (DEP) (Hughes, 2002, *Electrophoresis* 23:2569-2582), magnetic bead-based separators (Lee et al., 2001, *Appl Phys Lett* 79:3308-3310; Yan et al., 2004, *Phys Rev E* 70:011905), and deterministic hydrodynamics (Davis et al., 2006, *Proc Natl Acad Sci USA* 103:14779-14784). However, many existing methods have been unable to reliably achieve fast speed, high throughput and resolution, simultaneously with low costs (Dufresne et al., 1998, *Rev Sci Instrum* 69:1974-1977; Kremser et al., 2004, *Electrophoresis* 25:2282-2291; Cabrera et al., 2001, *Electrophoresis* 22:355-362). Optical tweezers offer high resolution and sensitivity for manipulating single cells, although such manipulation may cause sample heating (Liu et al., 1995, *Biophys J* 68:2137-2144), and is typically limited to a very small area (Ashkin et al., 1987, *Science* 235:1517-1520). Holographic schemes have recently extended the reach of optical tweezers to several tens of cells simultaneously (Applegate et al., 2004, *Optical Express* 12:4390-4398), although the overall throughput remains quite low.

Schemes based on electric fields, such as DEP, offer the potential to realize integrated, cost effective devices for the simultaneous manipulation of multiple cells. Nevertheless, their performance depends sensitively on the electrical properties of the specific liquid medium, the particle shape, and its effective dielectric constant (Pethig et al., 1997, *Trends Biotechnol* 15:426-432). DEP device operating regimes and the working ionic medium need to be carefully optimized for each different cell type so as to reach a workable compromise between the need to reduce heating (Menachery et al., 2005, *NanoBiotechnology* 152:145149; Muller, et al., 2003, *IEEE Eng Biol Med Mag* 22:51-61) and minimize cell polarization (Sebastian et al., 2006, *J Micromech Microeng* 16:1769-1777). Using functionalized magnetic beads to separate target molecules and cells overcomes these challenges through the use of magnetic fields instead of electric. However, the downside of this technique is the lengthy incubation times and wash cycles, and the difficulty of removing the label post priori (Gijs 2004, *Microfluidics Nanofluidics* 1:22-40). The deterministic hydrodynamics approach, as demonstrated by Davis et al. (Davis et al., 2006, *Proc Natl Acad Sci USA* 103:1477914784), is capable of achieving high resolution of separation without the use of any electromagnetic fields. However, high throughput with this device requires high-resolution lithography on a large area, keeping the cost per device high.

Most common applications of ferrofluids in biomedicine involve highly dilute colloidal suspensions of magnetic nanoparticles. Their widest commercial use is as MRI contrast agents (Kim et al., 2005, *J Magn Magn Mater* 289:328-330). When properly coated with targeting antibodies, they can also be used in hyperthermia therapy for cancer or as sensors to detect pathogens (Scherer et al., 2005, *Brazilian J Phys* 45:718-727).

While these advances in the use of ferrofluids provide many opportunities in medicine and diagnostics, there remains a need in the art for a microfluidic platform that uses biocompatible ferrofluids for the controlled manipulation and rapid separation of both microparticles and live cells.

SUMMARY

A device for separating a sample of particles suspended in a biocompatible ferrofluid is described. In some embodiments, the device includes a microfluidic channel having a sample inlet, at least one output, and a length between the sample inlet and the at least one output, wherein a sample can be added to the sample inlet and flow along the length to the at least one outlet. The device includes a plurality of electrodes, wherein the microfluidic channel length traverses the plurality of electrodes, and further includes a power source for applying a current to the plurality of electrodes to create a magnetic field pattern along the length of the microfluidic channel. In some embodiments, the spacing between electrodes is gradually increased. In some embodiments, the spacing between electrodes is gradually decreased. In some embodiments, the plurality of electrodes comprise at least one electrode layer. In some embodiments, the plurality of electrodes comprises a plurality of electrode layers. In some embodiments, the plurality of electrode layers is in a substantially orthogonal pattern. In some embodiments, the plurality of electrodes comprises a pattern of concentric circles. In some embodiments, the walls of the microfluidic channel length include a pocketed, a ridged, a grooved, a trenched or a sloped region. In some embodiments, the microfluidic channel length transverses at least a portion of the plurality of electrodes at an angle between about 0-360 (and more particularly, 0-90 degrees). In some embodiments, the particles are living cells.

Also described is a system for separating at least one target from a sample suspended in a biocompatible ferrofluid. The system includes a microfluidic channel having a sample inlet, at least one output, and a length between the sample inlet and the at least one output, wherein a sample can be added to the sample inlet and flow along the length to the at least one outlet. The system also includes a plurality of electrodes, wherein the microfluidic channel length transverses the plurality of electrodes, and further generates a magnetic field pattern along the length of the microfluidic channel when a current is applied to the electrodes. The system further includes at least one target in a sample suspended in a biocompatible ferrofluid, wherein the at least one target is separated from the remaining sample as the at least one target passes along at least a portion of the microfluidic channel length. In one embodiment, the biocompatible ferrofluid comprises a suitable amount of ionic species to control the osmotic pressure on the cells to promote cell sustainability. In some embodiments, the biocompatible ferrofluid comprises a citrate concentration of between about 5-200 mM. In some embodiments, the biocompatible ferrofluid comprises a citrate concentration of about 40 Mm. In some embodiments, the biocompatible ferrofluid has a pH of about 7.4. In some embodiments, the at least one target is separated based on target size. In some embodiments, the at least one target is separated based on target shape. In some embodiments, the at least one target is separated based on target elasticity. In some embodiments, the target is separated by being directed to a selected outlet. In some embodiments, the target is trapped based on the spacing of electrodes. In some embodiments, the at least one target is a cell. In some embodiments, the at least one target is a particle.

Also described is a method for separating at least one cell type. The method includes the steps of suspending two or more cell types in a biocompatible ferrofluid to form a sample, passing the sample through a microfluidic channel that transverses a plurality of electrodes, applying a current to the plurality of electrodes to create a magnetic field pattern along the length of the microfluidic channel, and sorting the cells into at least one output channel based on a variation of at least one of cell size, shape and elasticity. In one embodiment, the cells are separated at an efficiency of at least about 90%. In some embodiments, the size resolution in separating is less than about 10 µm. In some embodiments, the cells are separated in less than about 1 minute.

In some embodiments, the systems, devices, methods, and products described herein relate to microfluidic platforms that use biocompatible ferrofluids for the controlled manipulation and rapid separation of both microparticles and live cells. In some embodiments, the systems, devices, methods, and products described herein enable high-throughput manipulation, label-free sorting and separating of cells via a concentrated ferrofluid that is biocompatible. Bio-compatibility of the ferrofluid is based on an effective balance, or concentration, of ionic surfactant, such as citrate. Biocompatibility generally requires a neutral pH, a sufficient osmotic pressure on the cells, and a stable ferrofluid (e.g., too much ionic content may destabilizes the suspension). The platforms exploit differences in particle size, shape, elasticity, morphology, etc., to achieve rapid and efficient separation. Using microspheres, size-based separation is demonstrated with about 99% separation efficiency and sub-10-µm resolution in less than, for example, about 45 seconds. The systems, devices, methods, and products described herein also provide for the continuous manipulation and shape-based separation of live red blood cells from sickle cells and bacteria. The ferromicrofluidic systems, devices, methods, and products described herein significantly reduce incubation times and increase diagnostic sensitivity in cellular assays through rapid separation and delivery of target cells to sensor arrays.

Thus, in some embodiments, a system for separating a plurality of target species suspended in a biocompatible ferrofluid is disclosed. The system includes a microfluidic channel including at least one sample inlet and at least one outlet, the microfluidic channel having a length extending between the at least one sample inlet and the at least one outlet, the microfluidic channel configured to receive a substantially continuous flow of a sample from the at least one sample inlet, the channel configured to flow the sample along the channel length to the at least one outlet, the sample including the plurality of target species and the biocompatible ferrofluid. The system also includes a plurality of electrodes, where the microfluidic channel length passes proximate at least a portion of the plurality of electrodes, and a power source configured to controllably apply at least one current to the plurality of electrodes to controllably generate a magnetic field pattern along at least a portion of the channel length of the microfluidic channel to cause at least two of the plurality of target species in the sample to separate.

Embodiments of the system may include any of the features described in the present disclosure, including any of the following features.

The power source may be configured to additionally controllably apply the at least one current to generate a magnetic force component and a magnetic torque component.

The plurality of target species separated may be separated in a direction substantially transverse to a direction of the substantially continuous flow of the sample in the microfluidic channel.

The substantially continuous flow of the sample may be provided by at least one of, for example, a pressure pump, a syringe pump, a peristaltic pump, a vacuum device, gravity, and/or capillary forces.

The power source may be configured to apply current according to at least one of, for example, a selected amplitude, a selected frequency, and/or a selected phase. Separation of the at least two target species of the sample may be based, at least in part, on the one or more of, for example, the selected amplitude, the selected frequency, and/or the selected phase of the current.

The spacing between the plurality of electrodes gradually may increase along the length thereof.

The spacing between at least some of the plurality of electrodes may gradually decrease along the length thereof.

The plurality of electrodes may be arranged in an electrode layer.

The plurality of electrodes may be arranged in a plurality of electrode layers.

The plurality of electrode layers may be arranged in a substantially orthogonal pattern.

The plurality of electrodes may be arranged in a pattern of concentric circles.

The walls of the microfluidic channel may define, for example, a pocketed, a ridged, a grooved, a trenched and/or a sloped region.

The microfluidic channel length may pass proximate to at least a portion of the plurality of electrodes at an angle between about 0-90°.

The plurality of target species may include at least one cell-based species. The cell-based species may include one or more of, for example, white blood cells, red blood cells, tumor cells, and/or bacteria-based cells.

In some embodiments, a device for separating a plurality of target species suspended in a biocompatible ferrofluid is disclosed. The device includes a microfluidic channel including at least one sample inlet and at least one outlet, the microfluidic channel having a channel length extending between the at least one sample inlet and the at least one outlet, with the microfluidic channel configured to receive a substantially continuous flow of a sample from the at least one sample inlet, and further configured to flow the sample along the channel length to the at least one outlet. The sample includes a plurality of target species and the biocompatible ferrofluid. The device also includes a plurality of electrodes positioned proximate the microfluidic channel, the plurality of electrodes configured to generate a magnetic field pattern along at least a portion of the channel length of the microfluidic channel when a current is applied to the plurality of electrodes. The magnetic field pattern is configured to cause at least two of the plurality of target species in the flow of the sample to separate when the flow of the sample travels along at least part of the microfluidic channel.

Embodiments of the device may include any of the features described in the present disclosure, including any of the features described above in relation to the system, and the features described below.

The device may further include a power source configured to controllably apply the current to the plurality of electrodes to controllably generate the magnetic field pattern.

The plurality of electrodes may be configured to generate a controllable magnetic force component and a controllable magnetic torque component.

The plurality of electrodes may be configured to cause the at least two target species to separate in a direction substantially transverse to a direction of the substantially continuous flow of the sample in the microfluidic channel.

The device may further include a flow generation unit configured to generate the substantially continuous flow. The flow generation unit may include at least one of, for example, a pressure pump, a syringe pump, a peristaltic pump, a vacuum device, a structure enabling flow via gravity, and/or a device to generate capillary forces.

The biocompatible ferrofluid may include a suitable amount of ionic species to control the osmotic pressure on the cells to promote cell sustainability. The biocompatible ferrofluid may include a citrate concentration of between about 5-200 mM. The biocompatible ferrofluid may include a citrate concentration of about 40 mM. The biocompatible ferrofluid may include an engineered ionic strength of about 150 mM such that the biocompatible ferrofluid is isotonic and adapted to sustain live eukaryotic cells.

The biocompatible ferrofluid may have a pH of about 7.4.

The at least two target species may be separated based on target size.

The at least two target species may be separated based on target shape.

The at least two target species may be separated based on target elasticity.

The at least two target species may be separated based on target morphology.

The at least two target species may be trapped based on one or more of, for example, spacing of electrodes, frequency of current applied, and/or phase of the current applied.

In some embodiments, a method for separating a plurality of target species is disclosed. The method includes receiving in an inlet of a microfluidic channel a substantially continuous flow of a sample including a plurality of target species suspended in a biocompatible ferrofluid, passing the sample along the microfluidic channel, and applying at least one controllable current to a plurality of electrodes positioned proximate the channel. The current is configured to controllably generate a magnetic field pattern along at least a portion of a channel length of the microfluidic channel to cause at least two of the plurality of target species in the sample to be separated.

Embodiments of the method may include any of the features described in the present disclosure, including any of the features described above in relation to the system and the device, and the features described below.

The method may further include sorting the separated at least two of the plurality of target species into at least one output channel based on a variation of at least one of, for example, cell size, shape, elasticity, and/or morphology.

Applying the at least one controllable current may include controllably applying the at least one current to generate a magnetic force component and a magnetic torque component.

Controllably applying the current to the plurality of electrodes causes the at least two of the plurality of target species to separate in a direction substantially transverse to a direction of the substantially continuous flow of the sample in the microfluidic channel.

Receiving the substantially continuous flow of the sample comprises generating a pressure to provide the continuous flow of the sample from an external source using at least one of, for example, a pressure pump, a syringe pump, a peristaltic pump, a vacuum device, a structure to enable gravity-assisted pressure, and/or a device to generate capillary forces.

Controllably applying the at least one current may include applying current with one or more of for example, a selected amplitude, a selected frequency, and/or a selected phase, wherein separation of the at least two target species of the sample is based, at least in part, on the one or more of for example, the selected amplitude, the selected frequency, and/or the selected phase of the current.

In some embodiments, a device to focus at least one target species suspended in a biocompatible ferrofluid is disclosed. The device includes a microfluidic channel configured to receive a sample containing the at least one target species and the biocompatible ferrofluid, the at least one target species in the received sample being substantially concentrated in an input flow with an associated input width. The device also includes at least two of electrodes positioned proximate the microfluidic channel, the at least two electrodes configured to generate controllable magnetic forces in the sample containing the ferrofluid when controllable electrical currents are applied to the at least two electrodes. The generated controllable magnetic forces cause the at least one target species to be focused in a resultant flow having a width narrower than the input width associated with the input flow.

Embodiments of the device may include any of the features described in the present disclosure, including any of the features described above in relation to the system, the first device and the method, and the features described below.

The at least two electrodes positioned proximate the microfluidic channel may be configured to conduct controllably supplied currents and to generate the controllable magnetic forces according to, at least in part, physical attributes of the at least two electrodes. The at least two electrodes include a structure having at least one of, for example, a substantially straight shape of one or more of the at least two electrodes, a substantially wavy shape of the one or more of the at least two electrodes, a substantially parallel arrangement of the at least two electrodes, and/or a substantially tapering orientation of the at least two electrodes in which the at least two electrodes gradually approach each other.

The at least two electrodes may be configured to cause the at least one target species to flow into a space in the microfluidic channel located above and between the at least two electrodes.

The at least two electrodes may be configured to generate at least two magnetic waves of reverse traveling fields to cause the at least one target species to be focused at about a center of a boundary between the at least two generated magnetic waves.

The at least two electrodes may include a plurality of substantially parallel arranged electrodes.

The at least two electrodes may include an array of electrodes with at least some first electrodes of the array being arranged in a substantially tapering orientation relative to neighboring electrodes such that the first electrodes are configured to gradually approach neighboring electrodes, the array of electrodes being configured to generate magnetic forces to cause resultant flows of the at least one target species to form above and between pairs of neighboring electrodes.

The at least two of electrodes may be configured to generate controllable magnetic forces in the sample when the controllable electrical currents having associated phases are applied to the at least two electrodes. An associate phase of at least one of the electrical currents may be different from an associated phase of another of the electrical currents.

The at least one target species includes at least two target species. The plurality of electrodes may further be configured to cause at least two of the plurality of target species in the resultant focused flow to be separated.

The spacing between the at least two electrodes may gradually increase.

The spacing between the at least two electrodes may gradually decrease.

The at least two electrodes may be arranged in at least one electrode layer.

The at least two electrodes may be arranged in a plurality of electrode layers.

The microfluidic channel length may pass proximate to at least a portion of the at least two electrodes at an angle between about 0-90°.

The at least one target species may include a cell-based target species.

In some embodiments, a system to focus at least one target species suspended in a biocompatible ferrofluid is disclosed. The system includes a microfluidic channel configured to receive a sample containing the at least one target species and the biocompatible ferrofluid, the at least one target species in the received sample being substantially concentrated in an input flow with an associated input width. The system also includes at least two of electrodes positioned proximate the microfluidic channel, the at least two electrodes configured to generate controllable magnetic forces in the sample containing the ferrofluid when controllable electrical currents are applied to the at least two electrodes. The generated controllable magnetic forces causes the at least one target species to be focused in a resultant flow having a width narrower than the input width associated with the input flow. The system further includes a power source to controllably apply the controllable currents to the at least two electrodes.

Embodiments of the system may include any of the features described in the present disclosure, including any of the features described above in relation to the first system, the devices and the method, and the features described below.

The power source may be configured to apply currents including respective selected amplitudes, selected associated respective frequencies, and/or selected associated respective phases. Focusing of the at least one target species may be based, at least in part, on, for example, the respective selected amplitudes, the selected frequencies, and/or the selected phases of the applied currents.

The system may further include a pressure generation unit to provide the input flow, the pressure generation unit including at least one of, for example, a pressure pump, a syringe pump, a peristaltic pump, a vacuum device, a structure to enable gravity-assisted pressure, and/or a device to generate capillary forces.

The controllable magnetic forces may cause the resultant flow of the at least one target species to be pushed into a space in the microfluidic channel located above and between the at least two electrodes.

The at least two electrodes positioned proximate the microfluidic channel may be configured to generate at least two magnetic waves of reverse traveling fields causing the at least one target species to be focused at substantially a center of a boundary between the at least two generated magnetic waves.

The at least two electrodes configured to generate the associated at least two magnetic waves of reverse traveling fields may include a plurality of substantially parallel arranged electrodes.

The at least two electrodes may include an array of electrodes including a plurality of first electrodes arranged in a substantially tapering orientation relative to neighboring electrodes such that the first electrodes gradually approach neighboring electrodes, the array of electrodes configured to generate magnetic forces to cause resultant flows of the at least one target species to be formed above and between pairs of neighboring electrodes.

The at least two of electrodes may be configured to generate controllable magnetic forces in the sample containing the ferrofluid when controllable electrical currents having associated phases are applied to the at least two electrodes. An associate phase of at least one of the electrical currents may be different from an associated phase of another of the electrical currents.

In some embodiments, a method for focusing at least one target species in a microfluidic channel is disclosed. The method includes receiving a sample containing the at least one target species suspended in a biocompatible ferrofluid, the at least one target species in the received sample being substantially concentrated in an input flow with an associated input width. The method also includes controllably applying at least one current to at least two of electrodes positioned proximate the microfluidic to generate controllable magnetic forces in the sample containing the ferrofluid channel. The magnetic forces cause the at least one target species to be focused in a resultant flow having a width narrower than the input width associated with the input flow.

Embodiments of the method may include any of the features described in the present disclosure, including any of the features described above in relation to the systems, the devices and the first method, and the features described below.

Controllably applying the at least one current may include controllably selecting for the at least one current one or more of, for example, an associated respective amplitude, an associated respective frequency, and an associated respective phase. Focusing of the at least one target species may be based, at least in part, on, for example, the respective selected amplitude, the respective selected frequency, and/or the respective selected phase of the applied at least one current.

The method may further include providing the input flow using a pressure generation unit, the pressure generation unit including one or more of, for example, a pressure pump, a syringe pump, a peristaltic pump, a vacuum suction device, a structure to enable gravity-assisted pressure, and/or a device to generate capillary forces.

The at least two electrodes configured to conduct controllably supplied currents to generate the controllable magnetic forces cause the resultant flow of the at least one target species to be pushed into a space in the microfluidic channel located above and between the at least two electrodes.

In some embodiments, a device to detect at least one target species in a sample is disclosed. The device includes a microfluidic channel configured to receive the sample containing the at least one target species and a biocompatible ferrofluid in which the at least one target species is suspended, a detector to determine the at least one target species in the sample, and at least two of electrodes positioned proximate the microfluidic channel. The at least two electrodes are configured to generate controllable magnetic forces in the sample containing the ferrofluid when a controllable at least one electrical current is applied to the at least two electrodes, the generated controllable magnetic forces causing the at least one target species to be directed towards the detector.

Embodiments of the device may include any of the features described in the present disclosure, including any of the features described above in relation to the systems, the devices and the methods, and the features described below.

The at least two electrodes may include an array of electrodes with at least some of the electrodes arranged in a substantially tapering orientation relative to neighboring electrodes such that the at least some of electrodes are gradually approaching their neighboring electrodes.

The at least two of electrodes may be configured to generate controllable magnetic forces in the sample containing the ferrofluid when controllable electrical currents including associated phases are applied to the at least two electrodes. An associate phase of at least one of the electrical currents may be different from an associated phase of another of the electrical currents.

The sample may includes a plurality of target species, and the device may further include a set of electrodes configured to generate a controllable magnetic field pattern along at least a portion of length of the microfluidic channel when a controllable current is applied to the set of electrodes to cause at least two of the plurality of target species in the sample to be separated.

The microfluidic channel may configured to receive a flow of the sample from an external sample source.

The detector may include a pair of spaced electrodes to measure capacitance within the microfluidic channel, and an identification unit to determine presence of the at least one target species based on the measured capacitance.

The identification unit configured to determine the presence of the at least one target species may be configured to determine the presence of the at least one target species based on a change in measured capacitance in the microfluidic channel resulting from the presence of the at least one target species.

The detector may further include a capture region including a substance configured to interact with one of a plurality of target species, the capture region located in the microfluidic channel downstream of the pair of spaced electrodes, and another pair of spaced electrodes located downstream of the capture region to measure capacitance within the microfluidic channel. The identification unit may be configured to determine an initial number of at least one target species at the pair of spaced electrodes based on the capacitance measured at the pair of spaced electrodes, and an end number of the at least one target species based on the capacitance measured at the other pair of spaced electrodes, and to determine based, at least in part, on the difference between the initial and end numbers whether a level of the at least one target species captured by the capture region exceeds a pre-determined threshold.

The detector may include a cascade of sequentially positioned detection sets, each of the cascade of the sequentially positioned detection sets including a first pair of spaced electrodes to measure capacitance within the microfluidic channel, a capture region including a substance configured to interact with one of a plurality of target species, the capture region located downstream of the first pair of spaced electrodes, and a second pair of spaced electrodes located downstream of the capture region to measure capacitance within the microfluidic channel. The device may also include an identification unit to determine at each of the detection sets an initial number of at least one target species at the first pair of spaced electrodes based on the capacitance measured at the first pair of spaced electrodes, and an end number of the at least one target species at the second pair of spaced electrodes based on the capacitance measured at the second pair of spaced electrodes, and to determine based, at least in part, on the difference between the initial and end numbers whether a level of the at least one target species captured by the capture region exceeds a pre-determined threshold.

The detector may include a pair of spaced electrodes to measure impedance within the microfluidic channel, and an identification unit to determine presence of the at least one target species based on the measured impedance.

The identification unit configured to determine the presence of the at least one target species may be configured to determine the presence of the at least one target species based on a change in measured impedance in the microfluidic channel resulting from the presence of the at least one target species.

The detector may further include a capture region including a substance configured to interact with one of a plurality of target species, the capture region located in the microfluidic channel downstream of the pair of spaced electrodes, and another pair of spaced electrodes located downstream of the capture region to measure impedance within the microfluidic channel. The identification unit may be configured to determine an initial number of at least one target species at the pair of spaced electrodes based on the impedance measured by the pair of spaced electrodes, and an end number of the at least one target species at the other pair of spaced electrodes based on the impedance measured at the other pair of spaced electrodes, and to determine based, at least in part, on the difference between the initial and end numbers whether a level of the at least one target species captured by the capture region exceeds a pre-determined threshold.

The detector may include a cascade of sequentially positioned detection sets, each of the cascade of the sequentially positioned detection sets including a first pair of spaced electrodes to measure impedance within the microfluidic channel, a capture region including a substance configured to interact with one of a plurality of target species, the capture region located downstream of the first pair of spaced electrodes, and a second pair of spaced electrodes located downstream of the capture region to measure impedance within the microfluidic channel. The device may also include an identification unit to determine at each of the detection sets an initial number of at least one target species at the first pair of spaced electrodes based on the impedance measured at the first pair of spaced electrodes, and an end number of the at least one target species at the second pair of spaced electrodes based on the impedance measured at the second pair of spaced electrodes, and to determine based, at least in part, on the difference between the initial and end numbers whether a level of the at least one target species captured by the capture region exceeds a pre-determined threshold.

In some embodiments, a system to detect at least one target species in a sample is disclosed. The system includes a microfluidic channel configured to receive the sample containing the at least one target species and a biocompatible ferrofluid in which the at least one target species is suspended, a detector to determine the at least one target species in the sample, at least two of electrodes positioned proximate the microfluidic channel, the at least two electrodes configured to generate controllable magnetic forces in the sample containing the ferrofluid when a controllable at least one electrical current is applied to the at least two electrodes, the generated controllable magnetic forces causing the at least one target species to be directed towards the detector, and a power source to controllably apply the controllable at least one current to the at least two electrodes.

Embodiments of the system may include any of the features described in the present disclosure, including any of the features described above in relation to the systems, the devices and the methods, and the features described below.

The power source to controllably apply the controllable at least one current to the at least two electrodes may be configured to apply currents with associated respective selected amplitudes, selected frequencies, and selected phases, wherein directing the at least one target species towards the detector is based, at least in part, on the respective selected amplitudes, the selected frequencies, and the selected phases of the applied currents.

The system may further include a pressure generation unit to provide a flow of the sample, the pressure generation unit including one or more of, for example, a pressure pump, a syringe pump, a peristaltic pump, a vacuum suction device, a structure to enable gravity-assisted pressure, and/or a device to generate capillary forces.

In some embodiments, a method for detecting at least one target species in a sample is disclosed. The method includes receiving at a microfluidic channel a sample containing at least one target species suspended in a biocompatible ferrofluid, controllably applying at least one current to at least two of electrodes positioned proximate the microfluidic channel to generate controllable magnetic forces in the sample containing the ferrofluid channel to cause the at least one target species to be directed towards a detector, and determining the at least one target species in the sample based on measurements performed on the sample in the microfluidic channel by the detector.

Embodiments of the method may include any of the features described in the present disclosure, including any of the features described above in relation to the systems, the devices and the methods, and the features described below.

Controllably applying the at least one current may include controllably selecting for the at least one current one or more of, for example, a respective associated amplitude, a respective associated frequency, and/or a respective associated phase. Directing the at least one target species towards the detector is based, at least in part, on, for example, the respective selected amplitude, the selected frequency, and/or the selected phase of the applied at least one current.

The method may further include providing the sample received in the microfluidic channel using a pressure generation unit, the pressure generation unit including one or more of, for example, a pressure pump, a syringe pump, a peristaltic pump, a vacuum suction device, a structure to enable gravity-assisted pressure, and/or a device to generate capillary forces.

The detector may include a pair of spaced electrodes to measure capacitance within the microfluidic channel, and determining the at least one target species may include determining presence of the at least one target species based on the measured capacitance.

The detector may further include a capture region including a substance configured to interact with one of a plurality of target species, the capture region located in the microfluidic channel downstream of the pair of spaced electrodes, and another pair of spaced electrodes located downstream of the capture region to measure capacitance within the microfluidic channel. Determining the presence of the at least one target species in the sample may include determining an initial number of at least one target species at the pair of spaced electrodes based on the capacitance measured at the pair of spaced electrodes, and an end number of the at least one target species at the other pair of spaced electrodes based on the capacitance measured at the other pair of spaced electrodes, and determining based, at least in part, on the difference between the initial and end numbers whether a level of the at least one target species captured by the capture region exceeds a pre-determined threshold.

The detector may include a cascade of sequentially positioned detection sets, each of the cascade of the sequentially positioned detection set including a first pair of spaced electrodes to measure capacitance within the microfluidic channel, a capture region including a substance configured to interact with one of a plurality of target species, the capture region located downstream of the first pair of spaced electrodes, and a second pair of spaced electrodes located downstream of the capture region to measure capacitance within the microfluidic channel. Determining the at least one target species may include determining at each of the detection sets an initial number of at least one target species at the first pair of spaced electrodes based on the capacitance measured at the pair of spaced electrodes, and an end number of the at least one target species at the second pair of spaced electrodes based on the capacitance measured at the other pair of spaced electrodes, and determining at each of the detection sets based, at least in part, on the difference between the initial and end numbers whether a level of the at least one target species captured by the capture region exceeds a pre-determined threshold.

The detector may include a pair of spaced electrodes to measure impedance within the microfluidic channel, and determining the at least one target species may include determining presence of the at least one target species based on the measured impedance.

The detector may further include a capture region including a substance configured to interact with one of a plurality of target species, the capture region located in the microfluidic channel downstream of the pair of spaced electrodes, and another pair of spaced electrodes located downstream of the capture region to measure impedance within the microfluidic channel. Determining the presence of the at least one target species in the sample may include determining an initial number of at least one target species at the pair of spaced electrodes based on the impedance measured at the pair of spaced electrodes, and an end number of the at least one target species at the other pair of spaced electrodes based on the impedance measured at the other pair of spaced electrodes, and determining based, at least in part, on the difference between the initial and end numbers whether a level of the at least one target species captured by the capture region exceeds a pre-determined threshold.

The detector may include a cascade of sequentially positioned detection sets, each of the cascade of the sequentially positioned detection set including a first pair of spaced electrodes to measure impedance within the microfluidic channel, a capture region including a substance configured to interact with one of a plurality of target species, the capture region located downstream of the first pair of spaced electrodes, and a second pair of spaced electrodes located downstream of the capture region to measure impedance within the microfluidic channel. Determining the at least one target species may include determining at each of the detection sets an initial number of at least one target species at the first pair of spaced electrodes based on the impedance measured at the pair of spaced electrodes, and an end number of the at least one target species at the second pair of spaced electrodes based on the impedance measured at the other pair of spaced electrodes, and determining at each of the detection sets based, at least in part, on the difference between the initial and end numbers whether a level of the at least one target species captured by the capture region exceeds a pre-determined threshold.

Unless defined otherwise, all technical and scientific terms used herein have the same meaning as commonly or conventionally understood. As used herein, the articles "a" and "an" refer to one or to more than one (i.e., to at least one) of the grammatical object of the article. By way of example, "an element" means one element or more than one element. "About," as used herein when referring to a measurable value such as an amount, a temporal duration, and the like, is meant to encompass variations of ±20% or ±10%, ±5%, or ±0.1% from the specified value, as such variations are appropriate to in the context of the systems, devices, and methods described herein. Throughout this disclosure, reference to ranges is merely for convenience and brevity and should not be construed as an inflexible limitation on embodiments of the systems, devices, and methods described herein. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments therebetween.

Other and further objects, features, aspects, and advantages of the present disclosure will become better understood with the following detailed description of the accompanying drawings.

BRIEF DESCRIPTION OF THE DRAWINGS

These and other aspects will now be described in detail with reference to the following drawings.

FIG. 1A is a schematic of a device that includes a microfluidic channel and electrodes to generate a magnetic field.

FIG. 1B is a COMSOL simulation of a magnetic field (dark arrows) and magnitude of magnetic flux density across the cross-section of the ferromicrofluidic device.

FIG. 1C is a graph of computed force and torque on a microsphere along the length of a microchannel.

FIG. 1D is a graph of computed magnetic force and torque as a function of frequency.

Like reference symbols in the various drawings indicate like elements.

DETAILED DESCRIPTION

Figures 2A, 2B:
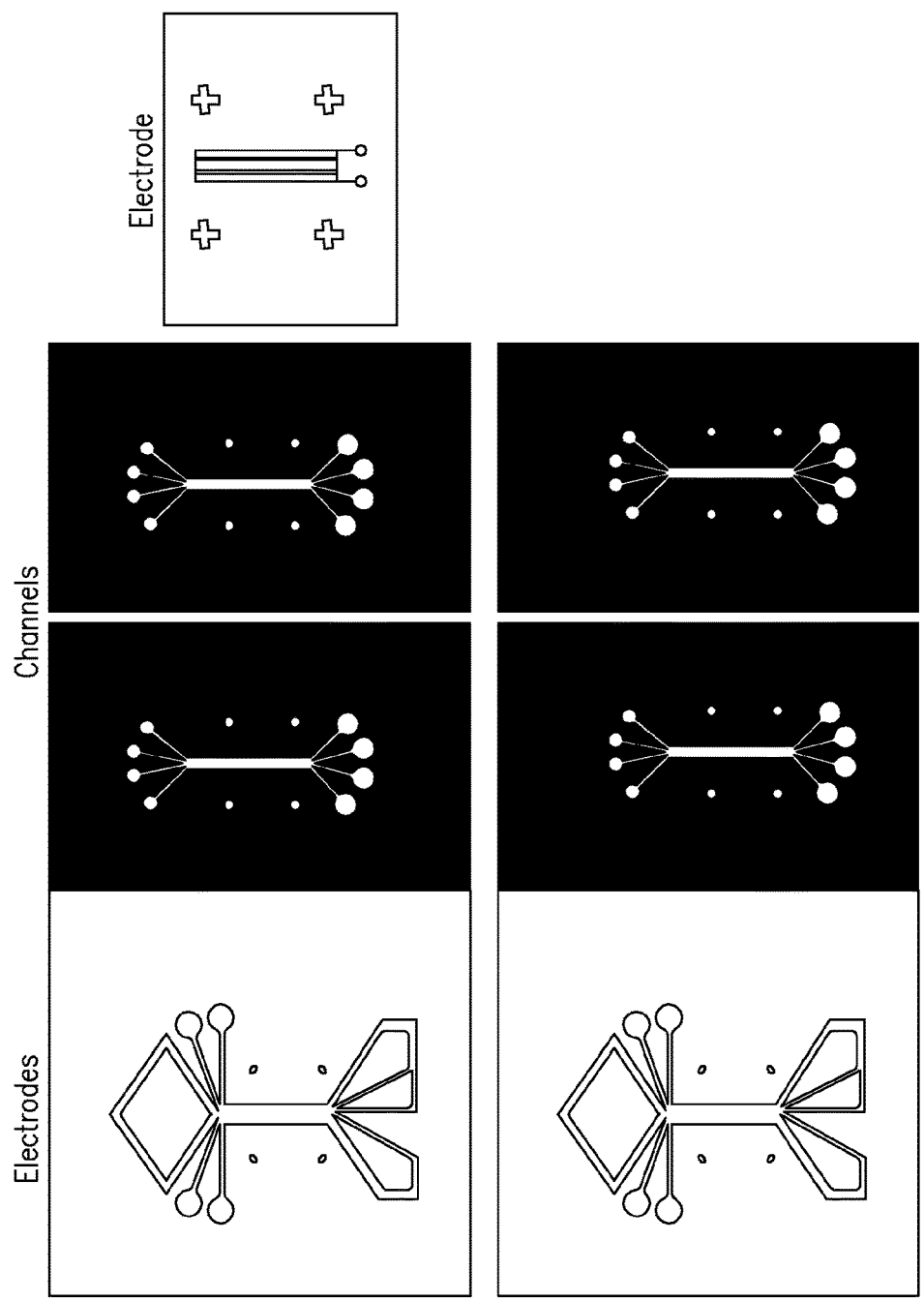
FIG. 2A are diagrams of example embodiments of alternative possible microchannel configurations that include electrode formations of 100, 150, 200 and 300 µm spacings.
FIG. 2B are diagrams of example channels with multiple inlets and outlets.

Disclosed herein are systems, methods, devices, products, and various implementations, including a device (e.g., for separating a plurality of target species suspended in a biocompatible ferrofluid) that includes a microfluidic channel including at least one sample inlet and at least one outlet, with the microfluidic channel having a channel length extending between the at least one sample inlet and the at least one outlet. The microfluidic channel is configured to receive a substantially continuous flow of a sample from the at least one sample inlet, and is also configured to flow the sample along the channel length to the at least one outlet. The sample includes a plurality of target species and the biocompatible ferrofluid. The device also includes a plurality of electrodes positioned proximate the microfluidic channel, the plurality of electrodes configured to generate a magnetic field pattern along at least a portion of the channel length of the microfluidic channel when a current is applied to the plurality of electrodes, with the magnetic field pattern configured to cause at least two of the plurality of target species in the flow of the sample to separate when the flow of the sample travels along at least part of the microfluidic channel.

Also disclosed is a device to focus at least one target species suspended in a biocompatible ferrofluid. The device includes a microfluidic channel configured to receive a sample containing the at least one target species and the biocompatible ferrofluid, with the at least one target species in the received sample being substantially concentrated in an input flow with an associated input width, and at least two of electrodes positioned proximate the microfluidic channel, the at least two electrodes configured to generate controllable magnetic forces in the sample containing the ferrofluid when controllable electrical currents are applied to the at least two electrodes. The generated controllable magnetic forces cause the at least one target species to be focused in a resultant flow having a width narrower than the input width associated with the input flow.

Further disclosed are systems, devices, methods, and implementations, including a device to detect at least one target species in a sample, the device including a microfluidic channel configured to receive the sample containing the at least one target species and a biocompatible ferrofluid in which the at least one target species is suspended, a detector to determine the at least one target species in the sample, and at least two electrodes positioned proximate the microfluidic channel. The at least two electrodes are configured to generate controllable magnetic forces in the sample containing the ferrofluid when a controllable at least one electrical current is applied to the at least two electrodes, the generated controllable magnetic forces causing the at least one target species to be directed towards the detector.

Generally, the ferrofluids used with the systems, devices, and methods described herein are colloidal mixtures of nanometer sized magnetic particles, such as cobaltferrite, covered by a surfactant, suspended in a carrier medium that is compatible with the surfactant material. For example, a sample reaction that results in magnetite particles is as follows:

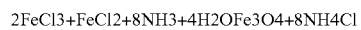

A 10% by volume suspension of magnetite has a saturation magnetization of around 560 G. The magnetization of each single-domain particle responds to a high magnetic field with a time constant on the order of 10 µs. High magnetic field gradients can be used to position the ferrofluid. "Spikes" and other interesting features may appear at the ferrofluid surface in the presence of such high fields.

In some embodiments, particle diameters can range from about 1 nm to about 100 nm, and any whole or partial increments therebetween. For example, and without limitation, the particle diameters can range between 1-10 nm, 1-20 nm, 5-50 nm, or 10-100 nm. In some embodiments, particle diameters average about 10 nm. Volume fractions may range from 0.1% to about 10%, and any whole or partial increments therebetween.

In some embodiments, the ferrofluids described herein are biocompatible and can sustain live cells for several hours without deterioration in physical properties or sustainability, enabling extended examination of the target sample. The biocompatible ferrofluid can be suitable for sustaining any living cell type and/or shape, such as any animal or plant tissue cell type, any microorganism, or any combination thereof, for example. The ferrofluid may also be suitable for suspending any type of particle, and for any sized or shaped particle, or particle clusters or clumps, whether living or non-living.

Citrate is an effective surfactant in ferrofluids, and it is mostly biocompatible in cell cultures as well. Therefore, in some embodiments, citrate is utilized both to stabilize the ferrofluid and to provide an ionic medium for the cells to survive in. In this context, determining a novel and optimum citrate concentration was desirable, because too little or too much citrate could result in particle aggregation and precipitation within the ferrofluid. Furthermore, cell survival within ferrofluids depends on having enough ionic species to control the osmotic pressure on the cells to promote sustainability. In one example embodiment, a citrate concentration within the ferrofluid resulting in a stable colloidal suspension of magnetic nanoparticles was about 40 mM. While higher citrate concentrations might begin to gradually destabilize the ferrofluid, concentrations of citrate may range anywhere between 5-200 mM, and any whole or partial increments therebetween, depending on the characteristics and type of ferrofluid used. In the example embodiment (depicted in FIG. 8C), it was also determined that the minimum concentration of citrate, stabilized with citric acid to result in a pH of about 7.4, that first resulted in substantial cell survival over the course of several hours was about 40 mM. At this ionic concentration, the cells were viable and the ferrofluid was stable. Thus, in some embodiments, a citrate concentration of about 40 mM can be used as an effective biocompatible ferrofluid. As contemplated herein, and depending on the type of ferrofluid used, the ferrofluids described herein may also be stabilized at pH ranges from between about 2-11, and any whole or partial increments therebetween. In some embodiments, the ferrofluid is biocompatible, such that cells can survive within the ferrofluid for at least about 1 hour, about 2 hours, about 3 hours, about 5 hours, about 10 hours, up to about 24 hours, or even longer. In some embodiments, the biocompatible ferrofluids used include an engineered biocompatible ferrofluid with an ionic strength of about 150 mM, with such a biocompatible ferrofluid configured to be isotonic and adapted to sustain live eukaryotic cells such as human cells, human cells, etc.

1. Separation Systems and Devices

As described herein, a microfluidic system, based on ferrohydrodynamics for label-free manipulation and separation of target species (e.g., cells and microorganisms) within biocompatible ferrofluids is provided. In some embodiments, the system includes a water-based ferrofluid used as a uniform magnetic environment that surrounds the cells or other particles within a microfluidic channel. Cells and other nonmagnetic particles within the ferrofluid act as "magnetic voids" (Kashevsky, 1997, *Phys Fluids* 9:1811-1818), in a manner analogous to electronic holes in a semiconductor. An externally applied magnetic field gradient can attract magnetic nanoparticles, which causes nonmagnetic microparticles or cells to be effectively pushed away (Rosensweig R E (1997) *Ferrohydrodynamics* (Dover, N.Y.); Odenbach S (2002) *Ferrofluids: Magnetically Controllable Fluids and Their Applications* (Springer, N.Y.)). Recently, this principle has been applied to capture nonmagnetic microbeads between magnetic film islands in a microchannel filled with ferrofluid (Yellen et al., 2005, *Proc Natl Acad Sci USA* 102:8860-8864). In contrast to this, the systems, devices, and methods of the present disclosure include microfluidic devices with electrodes (which may optionally be integrated electrodes, such as integrated copper electrodes) that carry currents to generate programmable/configurable magnetic field gradients locally. A mathematical description and analysis of the behavior and interactive relationships occurring as a result of application of a magnetic field on the microfluidic channel through which a sample including target species to be processed flows is provides below in Appendices A and B.

FIGS. 1A-1D illustrate example embodiments of a ferromicrofluidic device and particle manipulation platform. FIG. 1A is a schematic of a device 100 that includes a microfluidic channel 110 and underlying electrodes 120 (not drawn to scale). Two output channels from an amplifier provide, in some embodiments, sinusoidal currents (e.g., $I_1$ and $I_2$) that, in some implementations, are phase-locked 90° with respect to each other. The neighboring electrodes on the substrate are arranged/connected in a manner to carry the currents in quadrature and support a traveling wave magnetic fields within the microfluidic channel. The magnetic field gradient generated pushes the nonmagnetic microspheres or cells within the ferromicrofluidic channel up and into the gap between electrodes. The traveling field also causes the cells to rotate and roll along the channel ceiling, resulting in continuous translation along the length of the channel at frequencies above a threshold. The resulting microparticle motion may be observed with an upright microscope 130 from above and be captured, for example, with a CCD camera at 18 frames per second for further analysis. Further description of the ferromicrofluidic device and particle manipulation platform is provided, for example, in PCT application No. PCT/US10/59270, entitled "Label-Free Cellular Manipulation and Sorting Via Biocompatible Ferrofluids," and filed Dec. 7, 2010, as well as in U.S. provisional application Ser. Nos. 61/267,163, filed Dec. 7, 2009, and 61/407,738, filed Oct. 28, 2010, the contents of all of which are hereby incorporated by reference in their entireties.

Figure 3A:
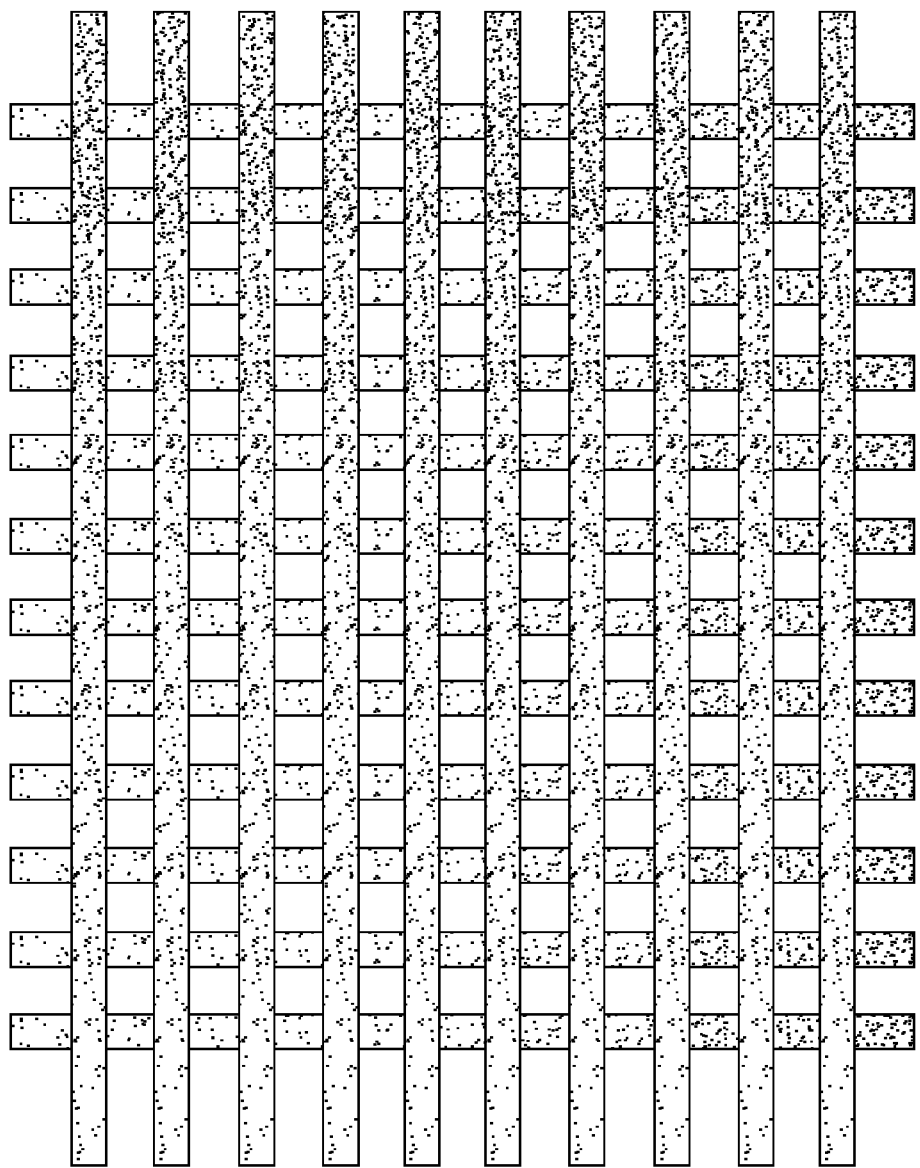
FIG. 3A is a schematic diagram of an example multi-dimensional electrode configuration that includes orthogonal electrode layers.

With continued reference to FIG. 1A, the electrodes 120, which may be arranged in an electrode layer, and positioned proximate the microfluidic channel 110, may sit atop a substrate such as a standard, insulated metal substrate 150. For example, an aluminum substrate coated with an insulating polymer may be used, which enables efficient heat sinking, and further enables the conductions of AC currents of up to, for example, 10 A at low voltages through the electrodes. In one example embodiment, a single electrode layer may be used, as depicted in FIG. 1A. In some embodiments, multiple electrode layers are used to provide multi-dimensional control (to thus enable multi-dimensional control of the magnetic fields that may be generated and applied to the sample in the microfluidic channel to manipulate and separate the target species in the sample). For example, FIG. 3A depicts an example of a multi-dimensional electrode configuration that includes orthogonal electrode layers.

Figure 3B:
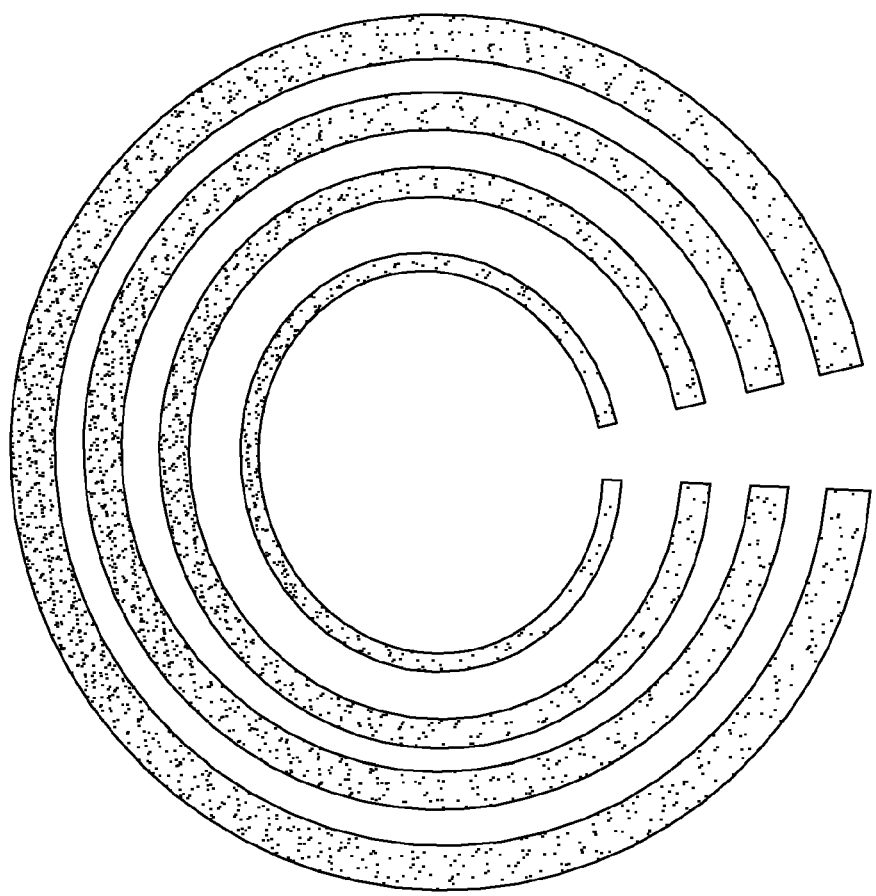
FIG. 3B is a diagram of electrodes in a pattern of concentric circles.

Within a given electrode layer, the electrodes may be about 30 μm high, about 300 μm wide and about 2 cm in length. In alternative embodiments, the electrodes within a given layer may range anywhere from about 5-100 μm high, about 0.01-1 mm wide, and about 0.1-10 cm in length, and any whole or partial increments therebetween. Thus, it should be appreciated that the size of electrodes utilized is not limited, and can vary across multiple electrode layers. Further, the electrodes may include any shape, curvature or pattern, and may include variable gap sizes between electrodes. For example, FIG. 2A depicts electrode formations of 100, 150, 200 and 300 spacing in the channel region. As noted, in some implementations, a multi-layer, orthogonal pattern may be used, as depicted, for example, in FIG. 3A. In yet other example embodiments, a concentric circle electrode pattern may be used, as depicted in FIG. 3B, to enable traveling waves to more effectively move the particles or cells into areas associated with the circles, out of areas associated with the circles, or trap them in various portions of areas associated with the circles. In some embodiments, the electrodes may have a "wiggly" (meandering), or generally curved shape so as to introduce disturbance forces and torques on nearby particles or cells. These wiggly regions may be uniform, non-uniform, random and/or periodic in nature, and may be distributed throughout the electrodes. It should be noted that the shape, spacing and pattern of electrodes may vary within a given electrode layer, and may further vary across multiple layers, such that any combination of shape, size, spacing and patterning may occur with an electrode layer and across multiple layers to create a desired magnetic field with desired attributes (with such attributes being further controllable, or configurable, through control of, for example, the currents applied to the electrodes).

In some embodiments, the electrodes may be composed of any suitable conductive material, such as copper. In some implementations, the electrodes can be fabricated by wet etching the copper layer of a thermal-clad printed circuit board (on an insulated metal substrate) through a photoresist mask. It should be noted that any type of etching or other suitable fabrication method may be used in creation of the electrodes.

The channel (such as the microfluidic channel 110 shown in FIG. 1A) may include at least one inlet and at least one outlet, and may be configured such that the channel's length passes proximate at least a portion of the electrodes, and may thus traverse at least the portion of the electrodes. For example, in some embodiments, the microfluidic channel can be rotated by about 90 degrees so that the electrodes of the device are substantially parallel to its length. In some other embodiments, the channel traverses the electrodes at an angle of between about 0-90 degrees, and any whole or partial increments therebetween. In further example embodiments, the channel traverses the electrodes in a substantially straight line. In still other example embodiments, the channel traverses the electrodes in a curved, bent or generally irregular pattern In some implementations, the microfluidic channel can range from 20-100 µm high, 1-3 mm wide and 2-3 cm in length, and any whole or partial increments therebetween. Other dimension values for the channel may be used. In some embodiments, the channel may include any number and size of pockets, ridges, grooves, trenches, and/or slopes within the channel walls, such that the particles or cells traveling within the channel can be locally concentrated or dispersed, based on the conformational effects of the contours of the channel walls. Additional example channels, with multiple inlets and outlets, are depicted in FIG. 2B. The channels may be composed of any suitable material. For example, in some embodiments, the channel may be prepared from polydimethylsiloxane (PDMS) stamps through soft lithography, and bonded to an insulating layer of thin PDMS covering the electrodes (Mao et al., 2006, *Nanotechnology* 17:34-47). In some embodiments, the channel height may be selected to be below the optimum for localized ferrohydrodynamic flow, in order to minimize its potential effects on particle migration.

While not required, the channel can be washed with a 1% triton-X solution for about 10 minutes before introducing the ferrofluid/microsphere mixture into the microfluidic device, to minimize particle attachment to the PDMS walls. It should be appreciated that the substrate, insulating layer and channel can each alternatively be composed of materials having similar features and/or properties. Thus, the devices and system described herein can be constructed, for example, on an inexpensive printed circuit board featuring an insulated copper layer etched via a single, low-resolution transparency mask to define the electrodes. As noted, the microfluidic channel can be constructed via soft lithography using a low-resolution mold. In some embodiments, device fabrication does not necessitate a clean room, and hence, can be fabricated rapidly and inexpensively.

To manipulate the sample to perform the desired processing on the sample (e.g., separate at least two of a plurality of target species, focus the target species, etc.), a travelling magnetic field is generated within the channel by applying a controllable at least one current (and, in some embodiments, at least two currents) delivered from a power source to the electrodes (such as the electrodes 120 depicted in FIG. 1A) to create a magnetic field pattern along at least a portion of the length of the microfluidic channel. Alternating currents of up to about 7 A peak-to-peak in amplitude and with frequencies from about 10 Hz to 100 kHz, which correspond to a maximum magnetic field strength of about 90 Oe within the ferrofluid, can be applied to the electrodes. In some variations, the generated magnetic field strength may range between 1-200 Oe, and any whole or partial increments therebetween. In one example, a magnetic field is generated by applying alternating currents in quadrature to a single layer of electrodes, to create a periodic magnetic field pattern that travels along the length of the microchannel. With this configuration, the device is able to create both magnetic field gradients, resulting in a time-average force on the cells or particles, and local rotation of ferrofluid magnetization, which eventually results in torque on the nonmagnetic particles, as illustrated in FIG. 1B. FIG. 1B depicts a COMSOL simulation of a magnetic field (dark arrows) and magnitude of magnetic flux density across the cross-section of the ferromicrofluidic device at a given instant in time. Fainter arrows depict the field at every 30° within one period. The simulation results illustrated were performed for a 12-A peak-to-peak current input at a frequency of 1670 Hz.

When the controllable at least one current is applied to the electrodes, two or more target species (cells or particles) are pushed away from the electrodes to the top of the channel, due at least in part to magnetic force, where they start to rotate and roll along its length, due at least in part to magnetic torque. The device behavior can thus mimic the frequency-dependent susceptibility of the particular ferrofluid used. For a given particle size, its speed may depend on the local force and torque values along the channel length, as illustrated, for example, in FIG. 1C (showing a graph of computed force and torque on a 6-µm diameter microsphere along the length of the microchannel with 7-A peak-to-peak input excitation at 4.6 kHz).

At low frequencies, the magnetic force component generally dominates, pushing nonmagnetic microparticles up to the channel ceiling (i.e., the surface opposite the surface that is closest to the electrodes and into the space between the electrodes. At high frequencies, the rolling microparticles can overcome the diminishing repulsion caused by magnetic force and move continuously along the channel, as illustrated in FIG. 1D. FIG. 1D is a graph of computed magnetic force and torque as a function of frequency for the same particle located between electrodes on the channel ceiling (the input current amplitude used to perform the simulation was 7 A peak-to-peak, with the assumed slip factor for all simulations being 1).

By way of example, a typical magnetic force that can be applied on a particle that is several micrometers in diameter can be on the order of tens of piconewtons, which is significantly larger than what is typical with optical tweezers on µm-size particles. In some embodiments, the actuation force can be increased by applying larger excitation currents. For example, a simple heat sink can maintain the channel contents at room temperature up to 10-A peak-to-peak input current (Mao L, Koser H (2006) Toward ferrofluidics for µ-TAS and lab on-a-chip applications. *Nanotechnology* 17:34-47).

Thus, the attributes (strength, frequency, phase, etc.) of the magnetic field generated by applying the at least one current to the electrodes (such as the electrodes 120) may be based on, for example, the particular characteristics of the current(s) applied through the electrodes (e.g., the amplitude(s), frequency(ies), phase(s) of the current applied). In some implementations, the attributes of the at least one current applied to the electrodes may be controlled using a controller, such as a processor-based controller, such as a controller 160 depicted in FIG. 1A (or some other computing device) that can determine the required current attributes needed to generate and maintain some required magnetic field. For example, in some embodiments, the controller may enable dynamic adjustment of the current attributes based on conditions detected within the device (e.g., varying the magnetic field if it is determined that the non-magnetic target species, such as particles, cells, etc., within the sample are not being processed as required or as expected, e.g., they are not properly separating).

Additionally and/or alternatively, in some implementations, the attributes of the magnetic field generated may also be based on the configuration of the microfluidic channel (e.g., its structure, materials used to implement the channel), the configuration of the electrode(s) (e.g., their arrangement, spatial relationship of the electrodes to the microfluidic channel, materials used to implement the electrodes, etc.), as well as other factors. Thus, to control the magnetic field generated in order to control and regulate, for example, the separation functionality of the device 100, one or more of the elements constituting the device may be controlled or manipulated. For example, as noted, in some implementations, the magnetic field applied to the sample to enable separation of at least two of a plurality of target species in the sample may be controlled by controllably applying at least one current (supplied by a power source that may be connected to the separation device, such as the device 100) to the electrodes (such as the electrodes 120 of FIG. 1A). Controllably applying the at least one current to the electrode(s) of the device 100 may include, in some embodiments, controlling/setting the power source so that the power source applies at least one current having a respective selected amplitude, a selected frequency, and/or a selected phase. Under those circumstances, separation of at least two target species in the sample may be based, at least in part, on one or more of the respective selected amplitude, the selected frequencies, and selected phases for the current(s) applied.

As noted, in some embodiments, attributes of the magnetic field generated and applied to the sample may be determined, for example, based on the configuration of the microfluidic channel and/or the configuration of the electrodes that are positioned proximate to the microfluidic channel. For example, with reference again to FIG. 2A, schematic diagrams of example embodiments of alternative possible microchannel configurations that include electrode formations of 100, 150, 200 and 300 μm spacing in the channel are shown. FIG. 2B depicts channel formations of between about 0.17-0.19 cm, and having four inlets and four outlets. In another example, and with reference again to FIGS. 3A and 3B, schematic diagrams depicting alternative embodiments of electrode patterns are shown. Specifically, FIG. 3A depicts a multi-layer electrode pattern that is substantially orthogonal, and FIG. 3B depicts electrodes in a pattern of concentric circles. The various configurations depicted in FIGS. 2 and 3 thus provide another way/mechanism to control the attributes magnetic field that can be generated to, for example, separate, focus, direct, and/or otherwise manipulate and actuate target species in a sample flowing in the microfluidic channel (such as the channel 110 of FIG. 1A).

Figure 4A:
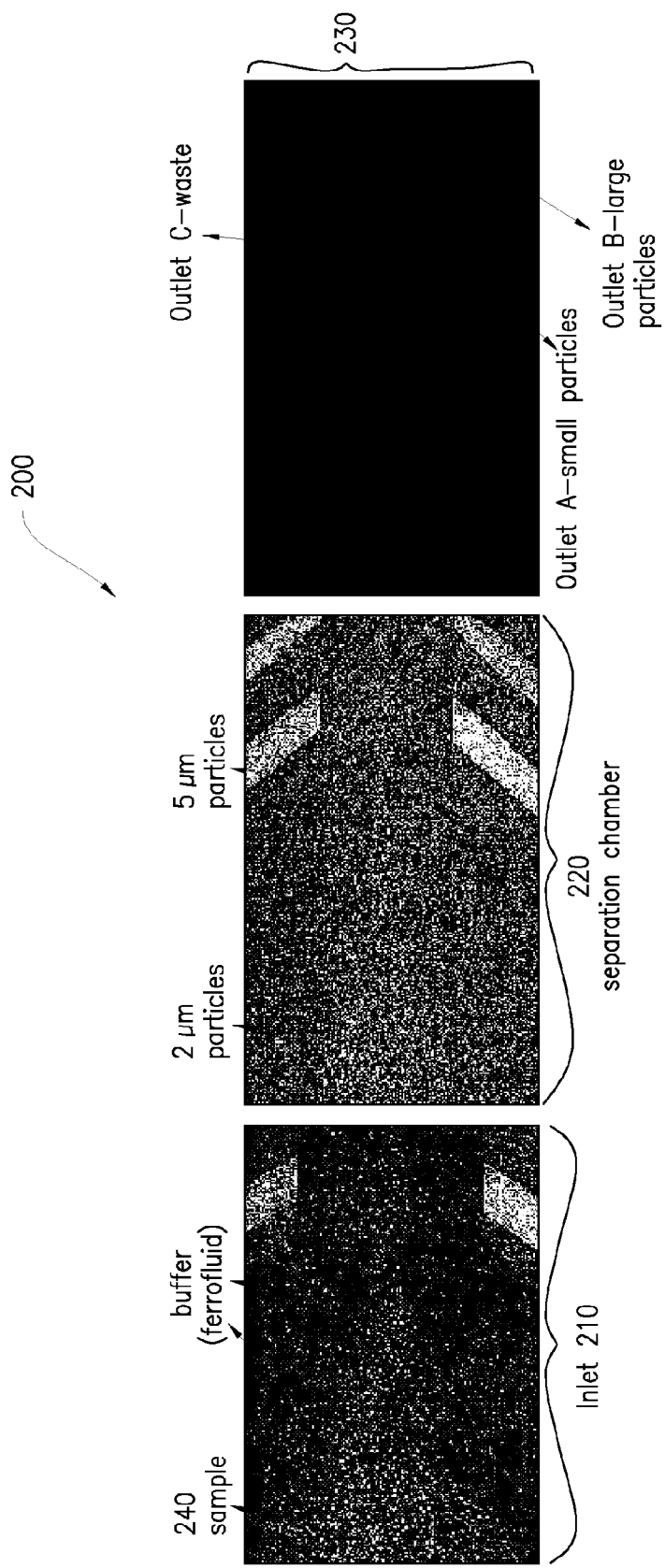
FIG. 4A is a diagram of a device implemented for continuous flow operation through a microfluidic channel.
Figure 4B:
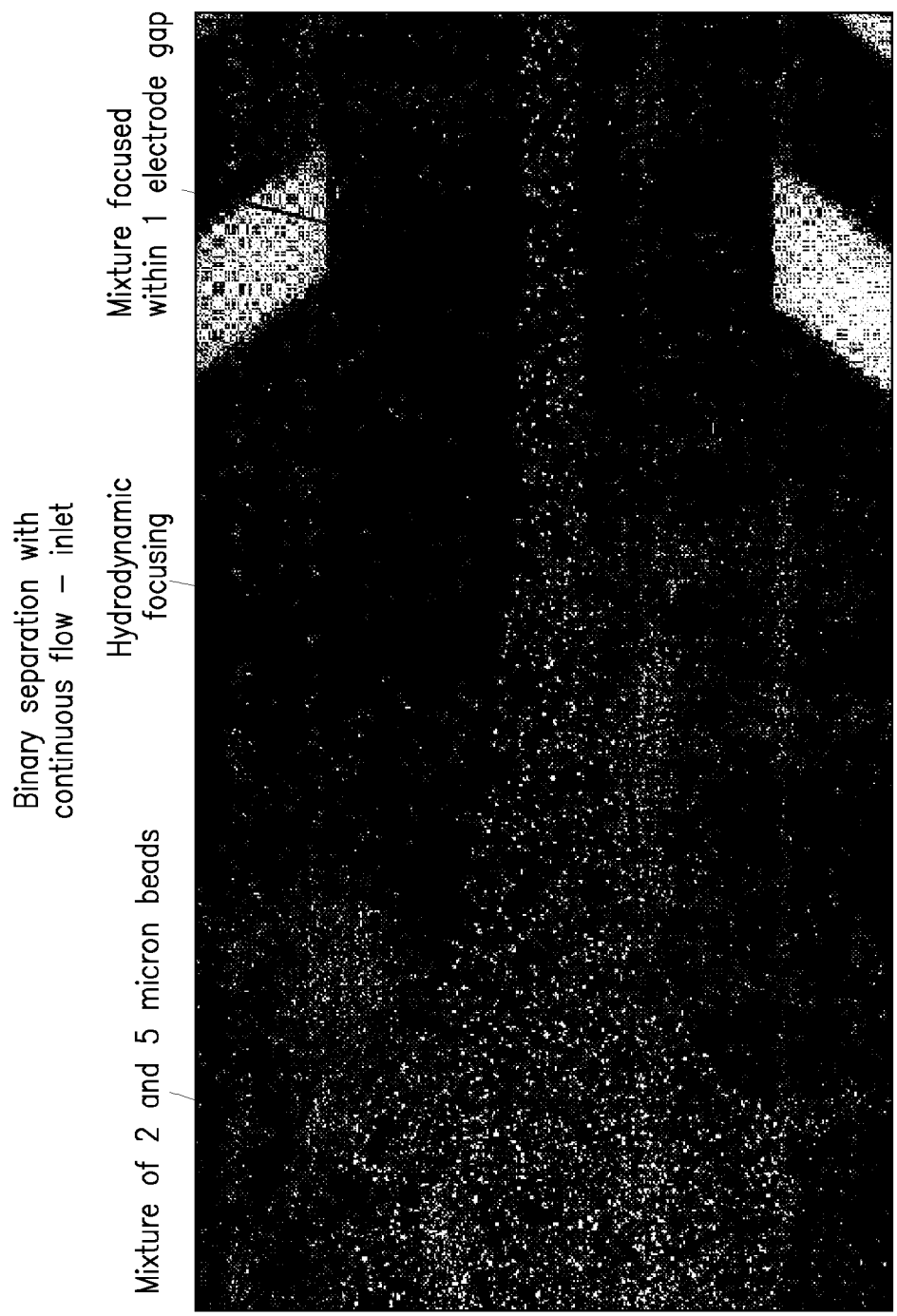
FIGS. 4B-D are magnified views of various sections of the device shown in FIG. 4A.
Figure 4C:

In some implementations, a separation device, such as the device 100 of FIG. 1A may be configured to enable separation of target species within a sample delivered as a continuous flow to the microfluidic channel of the device. With reference now to FIG. 4A, a diagram showing parts of a continuous flow separation device 200, implemented using a microfluidic channel configured to enable flow of target species in a sample on which a magnetic field generated by electrodes is applied, is shown. The device 200 may be similar to the device 100 depicted in FIG. 1A, or it may be based on a different implementation with, for example, a different electrode configuration and/or a different microfluidic channel configuration. FIG. 4A depicts a continuous flow device allowing a sample 240 suspended within a ferrofluid 250 to enter the device inlet and pass through the separation chamber, and exit via multiple outlets configured for capturing particles of a particular size. Specifically, the device 200 includes an inlet (also referred to as inlet stage) 210, a separation chamber 220, and an outlet (also referred to as an outlet stage) 230. In the example of FIG. 4A, a continuous flow sample containing two different target species, namely 2 μm particles and 5 μm particles, is introduced via the inlet 210. For example, in some embodiments, the sample may be introduced using at least one of a pressure pump, a syringe pump, a peristaltic pump, a vacuum device, and/or any other device coupled to the inlet 210 that causes the sample 240 to enter the inlet and to flow towards the separation chamber 220 and the outlet 230 of the device 200. Additionally and/or alternatively, in some embodiments, the continuous flow may be effected through gravity (e.g., height difference between the inlet and the outlet reservoirs) or by capillary forces. A magnified view of sample including the two target species is shown in FIG. 4B.

Figure 4D:

Through application of a controllable current through the particular electrode configuration of the device 200, a magnetic field with associated attributes (that are based at least in part on the controllable current(s) applied through the electrodes) is generated and causes the target particles to be separated. Generally, separation of the particles is performed as the sample (including the target species) flows through the separation chamber 220. As shown in FIG. 4A and in FIG. 4C (showing a magnified view of the separation chamber) the magnetic field generated causes the 2 μm particles to be separated from the 5 μm particles that are trapped, in the example depicted in FIGS. 4A and 4C, in the center gap stream. Subsequently, and as illustrated in FIGS. 4A and 4D, the 2 μm flow to outlet A in the outlet stage 230, while the 5 μm particles flow to outlet B of the outlet stage 230. The remaining sample flows to a waste outlet C. The device 200 depicted in FIGS. 4A-D is thus suitable for separating and sorting two or more particle types based on one or a combination of size, shape, elasticity, morphology, etc.

Figure 5:
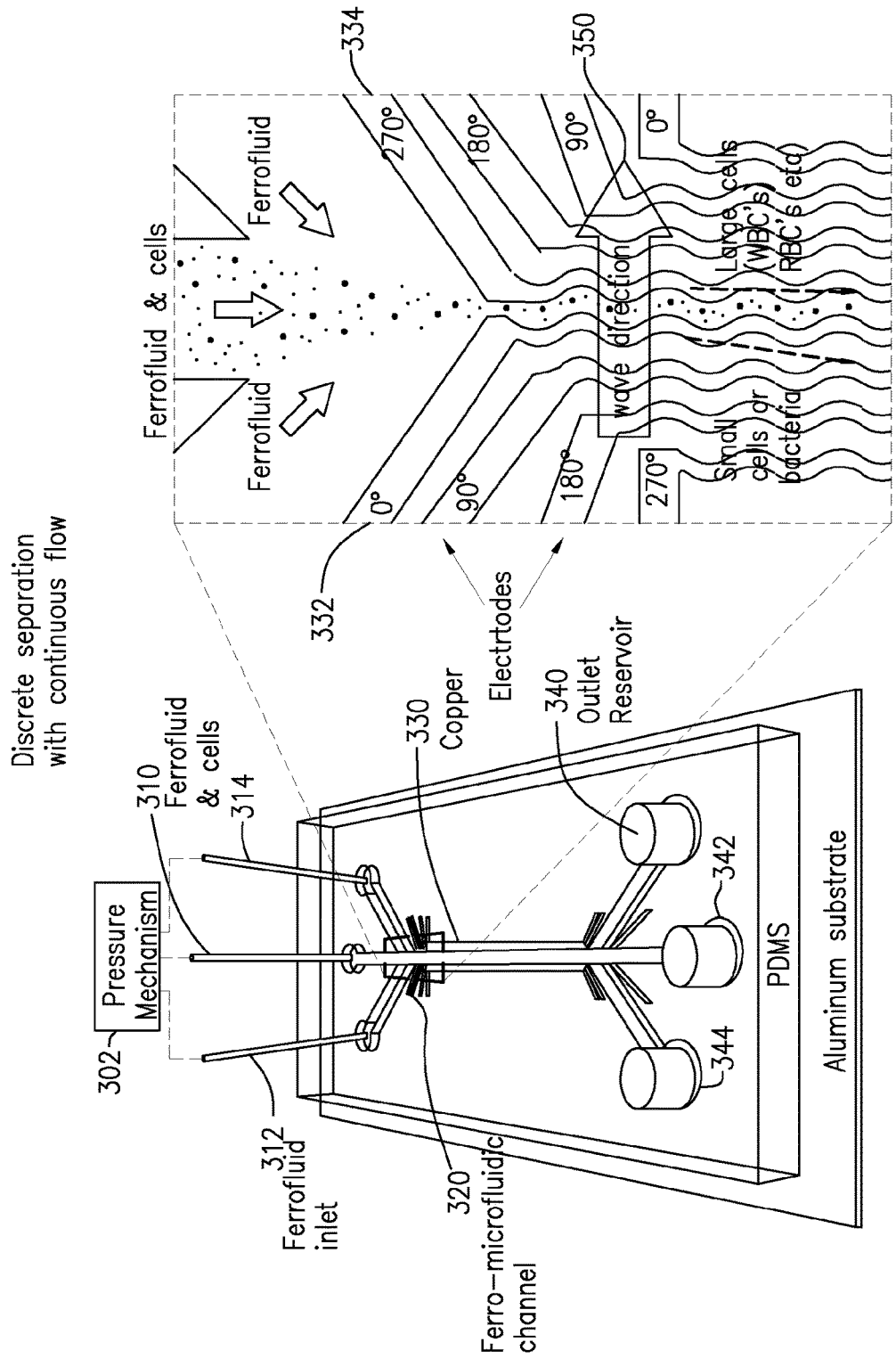
FIG. 5 is a schematic diagram of another example embodiment of a device implementing discrete separation with continuous flow.

With reference to FIG. 5, a schematic diagram of another example embodiment of a device 300 implementing discrete separation with continuous flow is shown. The device 300 includes one or more inlets, for example, an inlet 310 to receive a sample of ferrofluid and cells, and two inlets 312 and 314 that receive ferrofluid. In some embodiments, any number of inlets may be used, each of which may be configured to receive a mixture of ferrofluid and/or target species that are to be processed by the device through, for example, controlled application of a magnetic field directed at the microfluidic channel of the device. The materials received through the inlets may be received, in the implementations of FIG. 5, as a continuous flow that is provided by one or more pressure mechanisms, such as pressure mechanism 302, causing such a continuous flow. As explained herein, mechanisms to provided a continuous flow may include one or more, for example, a pressure pump, a syringe pump, a peristaltic pump, a vacuum device, gravity-based mechanisms, and/or capillary forces. In some implementation, the inlet stage may include a focusing mechanism to focus the target species into a single stream that is then processed by the magnetic field applied to the microfluidic channel of the device 300. The focusing mechanism may be based on hydrodynamic focusing and/or may be based on magnetic-based focusing (e.g., using permanent magnets and/or another set of electrodes to generate a field applied to the sample in the vicinity of the inlet stage).

As further shown in FIG. 5, the device 300 also includes a microfluidic channel 320 that may be similar to the channel 110 of FIG. 1A, and as such may be of various shapes and configurations, and may be constructed out of one of a plurality of different materials. The microfluidic channel 320 passes proximate at least a portion of a plurality of electrodes 330 (e.g., copper electrodes, or other types of electrodes). The plurality of electrodes 330 may be configured to have dimensions and other physical properties to facilitate generating a controllable magnetic field (when controllable current passes through the electrodes) with controllable attributes that is used to perform processing on the sample flowing in the microfluidic channel 320. For example, in the implementations of FIG. 5, the generated magnetic field enables performing separation of two or more target species suspended in the ferrofluid, with the separated materials being directed, as a result of the magnetic field separating the plurality of target species to at least one outlet reservoir. As depicted in FIG. 5, the plurality of electrodes includes 8 "wiggly" electrodes that are arranged (e.g., at various angles relative to the microfluidic channel 320) such that when controllable current is applied to the plurality of electrodes 330, a magnetic field with a direction shown by the arrow 350 is generated. Other attributes of the magnetic field generated may be controlled by controlling the at least one current applied to the plurality of electrodes. Controlling the current(s) applied may be performed, in some embodiments, using a controller such as the controller 160 of FIG. 1A. Also, by using a different configuration of the electrodes, the attributes of the magnetic field may further be adjusted/controlled, e.g., to generate a magnetic field with a different direction. The magnetic field generated using the device 300 causes the non-magnetic target species suspended in the ferrofluid to be directed to an area defined substantially between the electrodes 332 and 334. In some implementations, a permanent magnet(s) may be used in addition to, or in place of, the plurality of electrodes to generate the magnetic field applied to the sample flowing in the microfluidic channel. For example, a permanent magnet may be used to apply a magnetic field gradient perpendicular to the flow to push target species to facilitate separation of target species.

The traveling magnetic field generated (by, for example, application of at least one current, e.g., application of two currents having different phases) results in a generated magnetic force and torque that is applied to the plurality of target species (e.g., cells, bacteria, other particles). This causes the plurality of target species to simultaneously be pushed (e.g., onto the ceiling and towards the space above the gaps between electrodes using magnetic force) and to be rolled across the width of the channel along the ceiling (e.g., the surface opposite the surface closest to the electrodes) using magnetic torque. At high frequencies and small electrode gaps, magnetic torque dominates (leading to cells traveling across the tracks of gaps); at low frequencies and/or large gaps, magnetic force dominates (leading to cells staying focused within each track). The applied magnetic field can thus be used to implement discrete separation of the target species because in a device with increasing gap spacing, the cells will eventually be confined to individual tracks. The magnetic field causes separation of the target species based on one or more of for example, their respective sizes, their respective shapes, their respective elasticity, their respective morphology, as well as other characteristics of the target species.

As the sample on which the magnetic field operates travels the length of the microfluidic channel and approaches the outlet stage, the plurality of target species are separated (e.g., according to their sizes, shapes, morphology, elasticity, etc.), and are directed to respective separate outlet reservoirs. For example, in the embodiments depicted in FIG. 5, small target species (e.g., small cells or bacteria) drift towards the left side of the device 300, in the direction, for example, of outlet reservoir 344. Larger target species (e.g., WBC's, RBC's, etc.) drift in a different direction, e.g., towards the outlet reservoir 342. Other materials of the sample (e.g., waste) may be directed to the outlet reservoir 340. In some embodiments, only one outlet may be used.

The device 300, which delivers a continuous sample flow, achieves continuous, high-throughput separation, manipulation and sorting of microparticles and cells. Target species processing/manipulation takes place, in some implementations, transverse to externally imposed flow. In this fashion, the mechanisms of transport and separation of the plurality of target species can be decoupled. The flow rate can be optimized for high throughput, and cellular separation region dimensions can then be chosen accordingly. Through either hydrodynamic shear sheath flow from the sides or by magnetic forces, the target species (e.g., cell) mixture may be focused into a single gap over and between neighboring electrodes. The traveling magnetic fields generated by the currents in the electrodes will continue to separate and sort cells across the width of the separation chamber as they are dragged downstream with the flow.

Figure 6A:
FIGS. 6A-C are diagrams illustrating a device performing triple separation operations with a continuous flow.
Figure 6B:
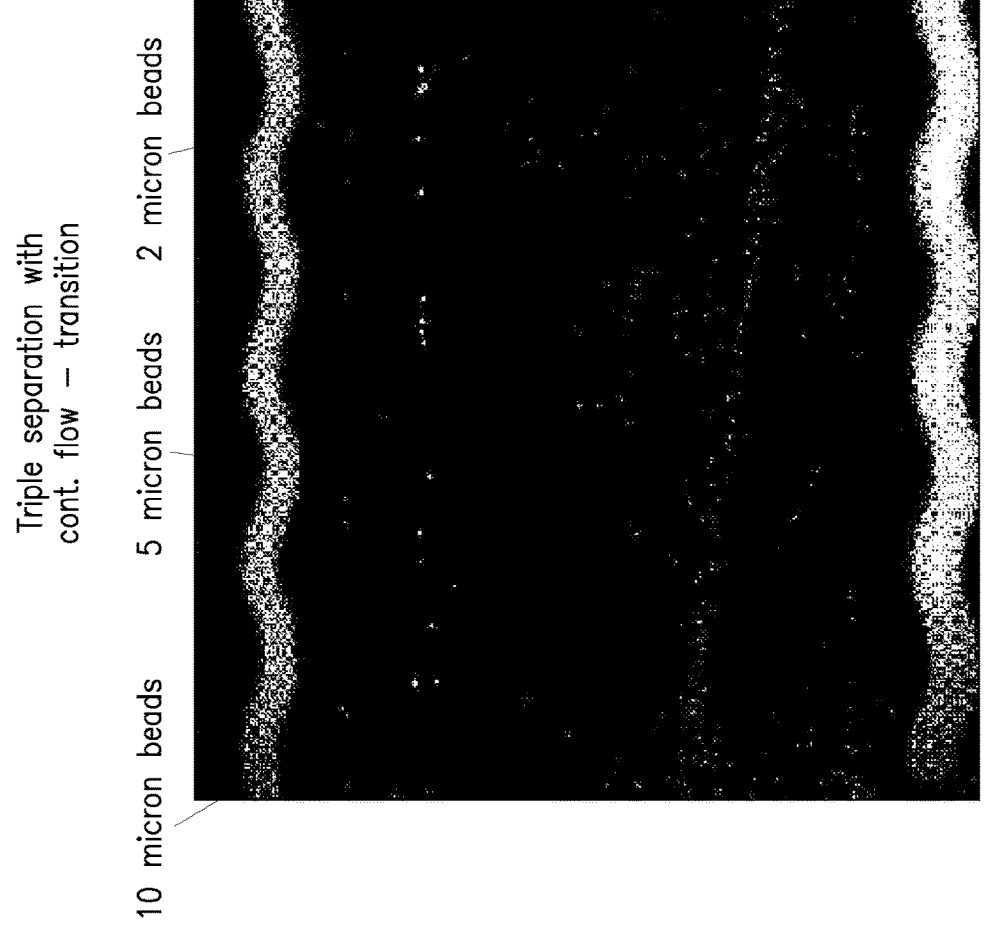
Figure 6C:
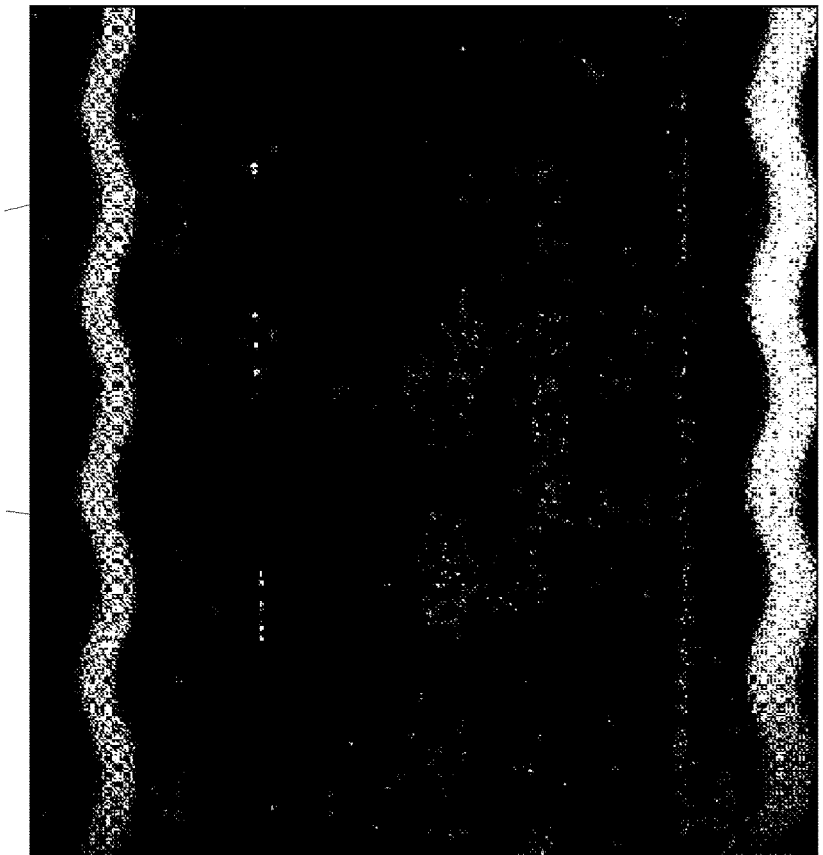

In some embodiments, by controlling the excitation frequency(ies), control over which target species will be trapped in the original electrode gap and which target species will be separated out can be achieved. Additional control in separation parameters may also be achieved by progressively changing the gap width between neighboring electrodes. Larger gaps make it easier to trap and focus ever smaller microparticles/cells. For instance, a gradient of neighboring gap sizes (e.g., 100 μm, 200 μm and 300 μm) can separate and then focus 10 μm, 5 μm and 2 microspheres, respectively, as illustrated, for example, in FIGS. 6A-C, showing operation of a device, such as the device 300, performing triple separation with continuous flow. In some embodiments, a similar approach may be used to create individual streams of white blood cells, red blood cells and platelets from blood. This would make it possible to get blood count results quickly and accurately within minutes. Other target cells (such as circulating tumor cells) may be separated from the rest of the blood cells by tagging them with microspheres (magnetic or non-magnetic) so that their total hydrodynamic volume is substantially different from the blood cells for reliable separation. Unlike conventional separation devices, such as flow cytometers, which typically cost on the order of ~$100K, occupy whole bench top, and require many components including multiple lasers, pumps, plumbing, reagents, fluorescent dyes and skilled technicians, the discrete microfluidic channel separation devices and systems described herein complete sample processing within minutes (instead of hours) and in a package that is cheap enough that it can be disposed of at the end of the processing.

Figure 7:
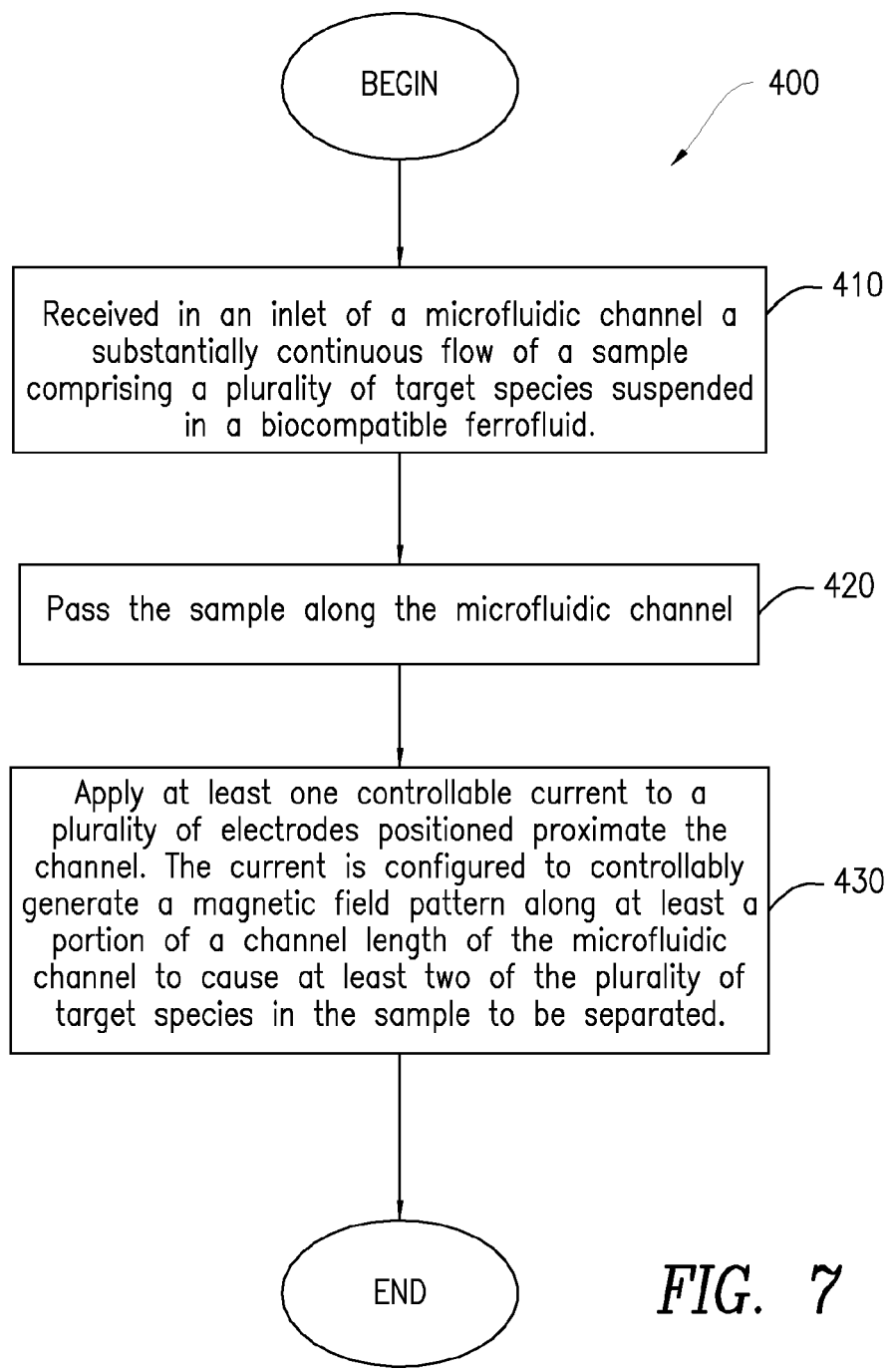
FIG. 7 is a flowchart of an example procedure to perform discrete separation of a plurality of target species suspended in ferrofluids.

With reference to FIG. 7, a flowchart of an example procedure 400 to perform discrete separation of a plurality of target species suspended in ferrofluids is shown. The procedure 400 includes receiving 410 in an inlet of a microfluidic channel, such as the microfluid channels depicted in FIGS. 1A, 4, and 5, a substantially continuous flow of a sample including the plurality of target species suspended in a biocompatible ferrofluid. The biocompatible ferrofluid may be any of the ferrofluids described herein, that are configured to sustain biological specimen (e.g., human or animal cells) for relatively prolonged periods of time (e.g., several minutes to several hours). To enable continuous flow of a sample that includes the plurality of target fluids, pressure to provide the continuous flow of the sample from an external source is generated using at lease one of, for example, a pressure pump, a syringe pump, a peristaltic pump, a vacuum device, a structure/device to enable gravity-assisted pressure, and/or a device to generate capillary forces. Other types of devices may also be used.

Having received the sample at the inlet(s) of the microfluidic channel-based device, the sample is passed 420 along the microfluidic channel. While the sample is flowing through the microfluidic channel of the device, at least one controllable current is applied 430 to a plurality of electrodes positioned proximate the channel (e.g., electrodes such as the electrodes 330 depicted in FIG. 5). The controllable at least one current is configured to controllably generate a magnetic field pattern along at least a portion of a channel length of the microfluidic channel to cause at least two of the plurality of target species in the sample to be separated. Particularly, as described herein, the controllable at least one current (as well as the chosen configuration of the electrodes and/or the of the microfluidic channel) enable controlling the attributes of the magnetic field generated so that the magnetic field is programmable or configurable. The magnetic field generated generally includes a magnetic force and torque component that causes the nonmagnetic materials (including the target species) to be pushed within the ferromicrofluidic channel up and into the gap(s) between electrodes. The traveling field also causes the cells to rotate and roll along the channel ceiling, resulting in continuous translation along the length of the channel at frequencies above a threshold. The magnetic field generated results in different target species having different spatial behavior and motion within the microfluidic channel that depends, at least in part, on the size, shape, morphology, elasticity, and other characteristics of the target species. Consequently, the various target species are separated, sorted, or otherwise distinguished from each other, enabling identification of the different target species present in the continuously flowing sample.

Thus, as described herein, a flow-based assay system, incorporating biocompatible ferrofluids, may be implemented. In some embodiments, a much higher throughput can be achieved by conducting bioferrofluidic separation while fluid flow continuously introduces fresh target species (e.g., cells) into the inlet of the channel. At the outlet, the incoming beads, cells, particles, are sorted into different output channels. From there, the cells can be collected for inspection or directed towards an external or internal (i.e., integrated) sensor. For example, the flow device allows a sample suspended within the ferrofluid to enter the device inlet and pass through the separation chamber, and exit via multiple outlets adapted for capturing particles of a particular size. For example, as depicted in FIG. 4A, 2 µm particles can flow to outlet A, 5 µm particles can flow to outlet B, etc., and the remaining sample may flow to outlet C. In some embodiments, flow is not needed to direct cells. Instead, magnetic excitation can be used to direct them. Further, the sensor may be directly integrated into a side pocket along the flow channel, for example.

Manipulation is not only dependent on cell size, but also on the shape and elasticity of the cells. For example, the variable size, shape and elasticity of bacteria and sickle cells allow them to be separated from healthy blood cells. In some embodiments, particle separation may be dependent on size and frequency. In some embodiments, critical frequency may also depend on the electrode gap. For example, larger microspheres can be trapped first in smaller gaps. By utilizing this phenomenon, sorting can be performed based on particle or target size. Further, the system may alternate between the manipulation excitation at the chosen frequency and another frequency that helps break possible nanoparticle chains that may form due to the magnetic excitation. In some variations, "wiggly" electrodes can be used to prevent beads or cells from clustering into large chunks as they flow down the channel. The "wiggly" electrodes introduce disturbance forces and torques on the beads or cells to break clusters apart, allowing for larger individual beads or cells to line up like pearls on a necklace. By periodically breaking the nanoparticle chains, the ferrofluid physical properties are kept constant over time. Further, target cells can be concentrated, trapped, localized, or simply directed toward sensor surfaces efficiently, rapidly, and in a label-free fashion. For example, the method of separation can direct a cell or particle type based on size, shape, elasticity, morphology, etc., into an outlet, or by trapping a cell or particle type based on size, shape, morphology, elasticity, and/or some other characteristic, via increasing or decreasing the spacing between electrodes.

Thus, procedures implemented to separate at least one target cell (a cell type) from a sample include suspending cells in a biocompatible ferrofluid to form a sample, passing the sample through a microfluidic channel that traverses a plurality of electrodes (such electrodes may be arranged at angles of 0-360° relative to the microfluidic channel, e.g., when arranged at an angle of 90° relative to the longitudinal axis of the microfluidic channel, the plurality of electrodes is substantially parallel to the length of the microfluidic channel. The procedures described herein may further include applying a current to the plurality of electrodes to create a magnetic field pattern along the length of the microfluidic channel, and sorting the cells into at least one output outlet based on a variation of at least one of cell size, shape and elasticity. Separation can occur via concentrating, trapping, localizing, or simply directing toward sensor surfaces efficiently, rapidly, and in a label-free fashion.

For example, in some embodiments, the procedures described herein also enable separating target species (e.g., cells and/or particles) based on size. This size-based separation can be demonstrated with, for example, about 50% efficiency, about 60% efficiency, about 70% efficiency, about 80% efficiency, about 90% efficiency, about 92% efficiency, about 94% efficiency, about 96% efficiency, about 97% efficiency, about 98% efficiency, and about 99% separation efficiency. Size resolution in the separation process can be, for example, less than about 10 µm, less than about 9 µm, less than about 8 µm, less than about 7 µm, less than about 6 µm, less than about 5 µm, less than about 4 µm, less than about 3 µm, less than about 2 µm, less than about 1 µm, less than about 0.5 µm, less than about 0.1 µm, and less than about 10 nm. Such separation can be accomplished in less than about 2 m, less than about 1 m, less than about 45 seconds, less than about 30 seconds, less than about 20 seconds, and less than about 10 seconds.

As further described herein, continuous manipulation and shape-based separation of target species (e.g., separation of cells, such as live red blood cells, from sickle cells and/or bacteria) may also be implemented. These demonstrations highlight the ability of ferro-microfluidics to significantly reduce incubation times and increase diagnostic sensitivity in cellular assays through rapid separation and delivery of target cells to sensor arrays.

The microfluidic systems and devices described herein have a number of unique advantages, in that they provide a laminar flow platform for use with tiny sample sizes. The systems/devices further provide fast diffusion and fast results, can be portable, and can be integrated with other existing sensors (as will be described in further details below). For example, the systems, devices, and methods described herein can be used for the sterilization of adult stem cells obtained from blood samples, for use in the context of wound healing and organ regeneration for soldiers and marines in combat. The systems, devices and methods described herein can also be used for the rapid detection (e.g., <1 min) of low-level bacterial contamination in donated blood. This can be particularly useful in battlefield trauma emergency situations. The systems, devices, methods described herein can also be utilized for "needle-in-a-haystack" applications that require the detection of ultra-low concentrations of cells in blood, such as searching for circulating tumor cells in blood.

EXPERIMENTAL EXAMPLES

To further illustrate the implementation and operation of the systems, devices, and methods described herein, the following examples are provided. These examples are not to be construed as being limiting the systems, devices, and methods described herein, but rather should be construed to encompass any and all variations which become evident as a result of the disclosure provided herein.

In implementing the experimental examples below, a co-precipitation procedure was used to synthesize cobalt-ferrite nanoparticles that were eventually incorporated into a water-based ferrofluid with a 20% solid content (Khalafalla S E, Reimers G W (1973) U.S. Pat. No. 3,764,540). Cobalt-ferrite nanoparticles were precipitated out of a boiling solution of 1 M sodium hydroxide by adding a mixture of cobalt (II)-chloride hexahydrate and iron (III)-chloride. The magnetic precipitate was washed twice using DI water. 2 M nitric acid and a 0.35 M solution of iron (III)-nitrate were added to the precipitate (Massart, 1981, *IEEE Trans Magn* 17:1247-1248; Fischer et al., 2008, *IEEE Int Conlon Nano/Micro Eng and Molecular Syst* China, 907-910). This mixture was then stirred at 80° C. for 20 minutes. The nitric acid solution was then decanted while the precipitate was held in place with a magnet. Cobalt-ferrite particles within the precipitate were later dispersed in DI water, and the resulting ferrofluid was dialyzed for one week against a 40 mM sodium citrate and citric acid solution at a pH level of 7.4. The solution was refreshed on a daily basis during dialysis. The resulting ferrofluid had a viscosity of 1.5 cP at 20° C.

In implementing the experimental examples below, transmission electron microscopy (TEM) images were taken using a Tecnai 12 electron microscope from Philips (120 keV). A copper/rhodium grid (from Electron Microscopy Sciences) was covered with a thin carbon film and dipped into a ferrofluid sample diluted with ethanol. After TEM images were obtained, particle sizes in the images were characterized using ImageJ software. The distribution of magnetic nanoparticle core sizes, as obtained from the TEM images (around 200 particles counted), was fitted with a lognormal probability density function as $$F(D) = \frac{1}{\sqrt{2\pi}\, D\sigma} \exp\left(-\frac{(\ln D - \ln D_0)^2}{2\sigma^2}\right) \qquad \text{(Equation 1)}$$

where D is the random variable depicting core diameter, while $D_0$ and $\sigma$ are the mean and standard deviation of ln(D), respectively.

The frequency-dependent AC susceptibility of the ferrofluid can be obtained by measuring the changes in the mutual inductance of an electromagnetic coil pair, with and without the presence of a ferrofluid (Maiorov, 1979, *Magnetohydrodynamics* 15:135-139). In this regard, a pick-up coil (of 200 turns, with an average diameter of 9.76 mm) was centered within a solenoidal excitation coil (of 340 turns with an average diameter of 13.34 mm), and the mutual inductance of the two coils was characterized via an LCR meter from Agilent (E4980A). The ferrofluid sample was introduced within the two sets of coils in a 1 cc plastic syringe. The symmetry in the setup ensured parallel field lines at the location of the pick-up coil and enabled an analytical calculation of mutual inductance, and eventually, AC susceptibility, from measured data.

The magnetization relaxation equation, assuming no fluid motion or convection (Rosensweig R E (1997) *Ferrohydrodynamics* (Dover: N.Y.)), is $$\frac{d\vec{M}}{dt} - \vec{\omega} \times \vec{M} = \frac{-1}{\tau}\left(\vec{M} - \chi_0 \vec{H}\right) \qquad \text{(Equation 2)}$$

where $\omega$ is the local vorticity within the ferrofluid, $\chi_0$ is the DC susceptibility value of the ferrofluid, and $\tau$ is the magnetic relaxation time constant associated with the magnetic nanoparticles. The uniform magnetic field within the cylindrical setup leads to a symmetry that makes vorticity (and hence, the second term in the above equation) negligible within the measurement volume. The magnetic relaxation time constant represents a combination of two physical relaxation processes. If the magnetic cores of the particles are small enough, their magnetic moment will simply rotate inside the nanoparticles (Néel relaxation) (Rosensweig R E (1997) *Ferrohydrodynamics* (Dover: N.Y.)) with a characteristic time constant given by $$\tau_N = \frac{1}{f_0} e^{(K_a V/k_B T)} \qquad \text{(Equation 3)}$$

where $f_0$ is a precession frequency (typically in the range $10^8$-$10^{12}$ Hz), $K_a$ is the magnetic anisotropy energy density, $V_{core}$, is the magnetic core volume of the nanoparticle, and $k_B T$ is the thermal energy. Particles with larger cores will have higher magnetic anisotropy energies, leading to fixed magnetic moments within the cores, and the particles themselves will rotate in solution to orient with the applied field (Brownian relaxation), with a characteristic time constant given by $$\tau_B = \frac{\pi D_{hyd}^3}{2 k_B T} \eta \qquad \text{(Equation 4)}$$

Here, $\eta$ is the dynamic viscosity of the fluid, $k_B$ is the Boltzmann's constant, T is the absolute temperature (in Kelvins), and $D_{hyd}$ is the hydrodynamic diameter of the particle, including its surfactant layer. The faster of the two mechanisms dominates the relaxation process. Cobalt-ferrite possesses a high magnetic anisotropy energy density (between $1.8\times10^5$ and $3.0\times10^5$ J/m$^3$ for bulk material and up to $3.15\times10^6$ J/m$^3$ for nanoparticles (Tung et al., 2003, *J Appl Phys* 93:7486-7488)), and ferrofluids based on this material relax primarily by particle rotation (Brownian mechanism) above a critical nanoparticle size of about 5 nm in diameter. Since most of the nanoparticles observed in the TEM pictures were larger than this critical size, only the Brownian time constant was considered in interpreting our AC susceptibility measurements.

The sinusoidal steady-state solution to Equation 2 in the absence of vorticity yields the concept of an effective susceptibility that describes the magnitude and phase relationship between ferrofluid magnetization and the applied field as a function of frequency f:

$$\chi(f) = \frac{\chi_0}{(1+i2\pi f \tau)} = \frac{\chi_0}{(1+(2\pi f \tau)^2)} - i\frac{2\pi f \tau \chi_0}{(1+(2\pi f \tau)^2)} \quad \text{(Equation 5)}$$

(Debye P J W (1929) *Polar Molecules*. (Dover: N.Y.)). Here, $\chi_0$ is the DC susceptibility value of the ferrofluid and $\tau$ is the Brownian relaxation time constant associated with the magnetic nanoparticles.

Ferrofluids consist of particles with a size distribution (typically lognormal), which leads to a distribution of the relaxation times as well. To take this into account, the overall AC susceptibility is described as a linear combination of all susceptibility spectra that would result from the particle sizes present in the ferrofluid, weighed by the lognormal probability density function $F(D_{hyd})$ associated with a given particle size:

$$\chi(f) = \frac{1}{A} \int_0^\infty \frac{\chi_0}{(1+i(2\pi f \tau_B))} V_{core}^2 F(D_{hyd}) dD_{hyd} \quad \text{(Equation 6)}$$

The magnitude of the total magnetization within a nanoparticle is proportional to its core volume; so is its individual contribution to the susceptibility spectrum. Hence, the probability density function in Equation 1 is scaled by $V_{core}^2$. The normalization factor A is given by $$A = \int_0^\infty F(D_{hyd}) V_{core}^2 dD_{hyd} \quad \text{(Equation 7)}$$

Figure 8A:
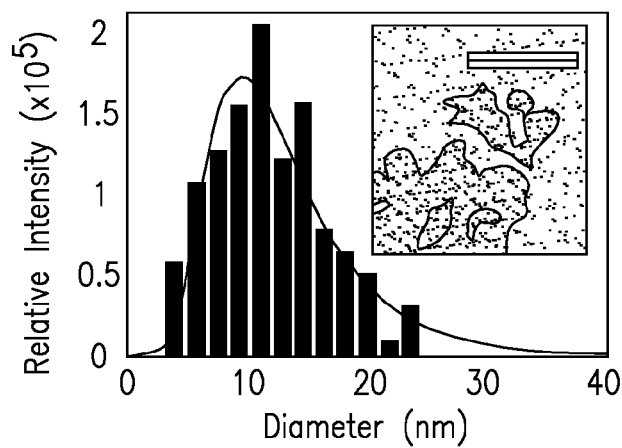
FIG. 8A is a graph depicting the distribution of cobalt-ferrite nanoparticle sizes within a ferrofluid.
Figure 8B:
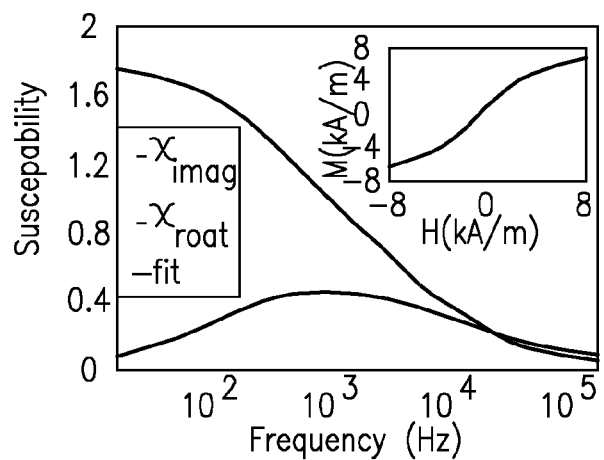
FIG. 8B is a graph depicting AC susceptibility and a de-magnetization curve of a ferrofluid.

The AC susceptibility data (an example of which is shown in FIG. 8B) can be fitted with the sinusoidal steady-state solution to the magnetic relaxation equation assuming a log-normal distribution of hydrodynamic diameters (Equations 4 through 7). Simultaneously, the relative shape of the DC magnetization data (as depicted in FIG. 8B-inset) can be fitted with the Langevin equation, once again assuming the same log-normal distribution of hydrodynamic diameters (and particle concentration as a free parameter). The simultaneous fits explain the experimental results very well, yielding an average hydrodynamic diameter of 72.5 nm. This value is much larger than the average core diameter of the nanoparticles as obtained with TEM. A reasonable explanation for this discrepancy is that, in equilibrium, the nanoparticles have formed moderate-sized aggregates that respond as single units to the magnetic fields that were applied during measurements. Dynamic light scattering experiments were also conducted on diluted samples of the same ferrofluid. Those results confirmed that the hydrodynamic diameters were much larger than the core diameters, supporting the explanation presented herein.

Typically, the surfactant concentration used was high enough to prevent continuous degradation in colloidal stability (at least over several months). Therefore, it is likely that the particle aggregates may have formed during one of the brief precipitation stages of the ferrofluid synthesis protocol, which often involves the use of a permanent magnet to speed the process. The surfactant is added later, and cannot break aggregates that have already formed.

In further implementing the experimental examples below, the dynamic light scattering experiments were conducted using a ZetaPALS instrument from Brookhaven Instruments Group. For these measurements, the ferrofluid was diluted with DI water to avoid multiple scattering. The hydrodynamic particle diameter was found to be 64.9 nm.

In additionally implementing the experimental examples below, the particle manipulation device (for example, the device 100 depicted in FIG. 1A) used in the experiments included two parts: the microfluidic channel and the underlying copper electrodes. The electrodes (30 µm high, 300 µm wide and 2 cm in length) were fabricated by wet etching the copper layer of a thermal-clad printed circuit board (on an insulated metal substrate) through a photoresist mask. A travelling magnetic field was generated in the channel by applying alternating currents in quadrature to a single layer of electrodes. The microfluidic channel (20 µm to 100 µm high, 1 mm to 3 mm wide and 2 cm to 3 cm long) was prepared from polydimethylsiloxane (PDMS) stamps through soft lithography and was bonded to an insulating layer of very thin PDMS covering the electrodes (Mao et al., 2006, *Nanotechnology* 17:34-47). The channel height was chosen to be well below the optimum for localized ferrohydrodynamic flow in order to minimize its potential effects on particle migration. In separate experiments with sub-micron tracer particles, no discernible hydrodynamic flow was observed. The insulated metal substrate allows efficient heat sinking, enabling AC currents up to 10 A at low voltages through the electrodes. Before introducing the ferrofluid/microsphere mixture into the microfluidic device, the channel was washed with a 1% triton-X solution for about 10 minutes in order to minimize particle attachment to the PDMS walls.

In also implementing the experimental examples below, different sizes (1.2 µm, 1.9 µm, 2.2 µm, 3.1 µm, 5.0 µm, 6.0 µm, 9.9 µm in diameter) of green fluorescent polystyrene microspheres were obtained from Duke Scientific (Fremont, Calif., USA). The coefficient of variation on the microsphere diameters was about 1%. These custom produced microspheres had a very low porosity and carried a minimal amount of charged groups on their surfaces. Microspheres were suspended in deionized (DI) water and kept at 4° C. until they were used in ferrofluid experiments.

Additionally, to make the cells visible within the ferrofluid, blood cells were stained with green fluorescent membrane dye PKH67 (obtained from Sigma-Aldrich). This dye has an excitation peak at 490 nm and emission at 502 nm (Horan et al., 1989, *Nature* 340:167-168). Cell staining was performed by following the manufacturer's protocol with some modifications.

The general preparation protocol used in performing the experimental examples below was as follows. Blood was drawn from donors prior to the experiments and kept at 4° C. prior to staining. Approximately 10 million cells were centrifuged and the plasma was subsequently removed. The cells were then suspended in 500 µl RPMI 1640 culture medium without serum (obtained from Invitrogen, Carlsbad, Calif., USA) and mixed well to remove any adherent and bound cells. The resulting suspension of cells was centrifuged again for 5 minutes at 1000 rpm.

The supernatant was carefully aspirated and the pellet was suspended in 500 µl Diluent C (supplied with the staining kit). Immediately after this, 4 micromolar PKH67 dye in Diluent C was prepared. Equal volumes of dye and cell solutions were mixed. The resulting cell suspension was incubated for 4 minutes, avoiding exposure to light. The staining reaction was stopped by adding an equal volume of fetal bovine serum (FBS) and the cell suspension was further incubated for 1 minute. The cells were then centrifuged for 5 minutes at 1200 rpm to remove the staining solution. They were washed three times in cell culture containing 10% FBS to remove any remaining dye in the solution. After washing was complete, the cells were suspended in culture medium. The brightness of labelled cells was tested with fluorescence microscopy. Before mixing with ferrofluid, the stained cells were washed with Dulbecco's phosphate buffered saline (PBS) buffer containing 10% FBS.

Additionally, because citrate is an effective surfactant in ferrofluids, and is mostly biocompatible in cell cultures, citrate was therefore utilized both to stabilize the ferrofluid and to provide an ionic medium for the cells to survive in. In this context, determining proper concentration was important because too little or too much citrate would result in particle aggregation and precipitation within the ferrofluid. Furthermore, cell survival within the ferrofluid depends on having enough ionic species to control the osmotic pressure on the cells to promote sustainability. The highest citrate concentration within the ferrofluid that still resulted in a stable colloidal suspension of magnetic nanoparticles was determined to be about 40 mM. Higher citrate concentrations would begin to gradually destabilize the ferrofluid.

Figure 8C:
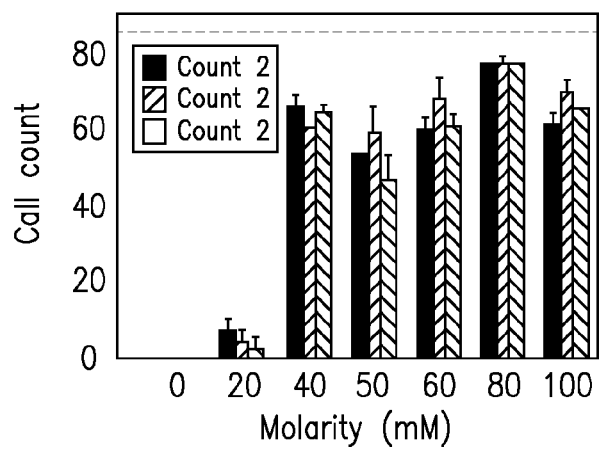
FIG. 8C is a chart depicting live cell count vs. citrate concentration.

Cell viability was monitored using the Trypan Blue (obtained from Invitrogen) staining technique. Trypan Blue is a dye that selectively stains dead cells blue, allowing live and dead cells to be distinguished (The Sigma-Aldrich Handbook of Stains, Dyes & Indicators, Green, F. J., ed., Aldrich Chemical Co. (Milwaukee, Wis.: 1990), 721-722). Following the manufacturer's protocol, 90 µl of 0.4% Trypan Blue Stain was added to 10 µl of the cell suspension with a concentration of $5 \times 10^5$ cells per 1 ml of culture medium. After incubation for 5 minutes at room temperature, a small sample from the mixture was placed onto a hemocytometer to count live cells. It was determined that the minimum concentration of citrate (stabilized with citric acid to result in a pH of 7.4) that first resulted in substantial cell survival over the course of several hours was 40 mM (as shown in FIG. 8C). At this ionic concentration, the cells were viable and the ferrofluid was stable. Hence, in all experiments involving cells suspended within our ferrofluid, a citrate concentration of 40 mM was used.

Example 1: Ferrofluid Properties and Device Characterization

Using highly concentrated ferrofluids with live cells has traditionally proven to be a challenge, because it requires a carefully engineered colloidal system. The ferrofluid parameters that are most relevant to sustaining live cells include pH, ionic strength, and nanoparticle-surfactant combination, together with their overall and relative concentrations.

Finding the right nanoparticle-surfactant combination is crucial in this regard: the ferrofluid needs to be stable at a pH of 7.4, and colloidal stability has to be maintained up to an ionic strength that can sustain live cells. Attention should also be given to the size distribution of the nanoparticles within the ferrofluid. If there are nanoparticles that are only a few nanometers in diameter, they could pass through the cell membrane and cause direct cytotoxicity (Scherer et al., 2005, Brazilian J Phys 45:718-727). For this reason, the systems, devices, and methods described herein include a magnetic precipitation step in the synthesis of the biocompatible ferrofluids to specifically leave the smallest nanoparticles behind.

Traditional approaches for improving ferrofluid biocompatibility typically involve covering the magnetic nanoparticles permanently with a thick polymer layer, such as dextran (Bautista, et al., 2004, Aranotechnology 15:S154-S159), because the surfactant molecules reduce toxicity by impeding direct contact with the surface of the inorganic nanoparticles. However, such an approach leads to a significant reduction in the volume content of the magnetic nanoparticles within the ferrofluid, and a corresponding decline in its susceptibility. Higher ferrofluid susceptibility typically translates to faster particle manipulation, so the ferrofluid of the present disclosure has been optimized by using a short surfactant molecule.

In some embodiment, the ferrofluid used included cobaltferrite nanoparticles suspended in water and stabilized with citrate. Mean nanoparticle core diameter within the ferrofluid, as determined with transmission electron microscopy (TEM), was found to be about 11.3±4.4 nm (as illustrated in FIG. 8A, showing a graph depicting the distribution of cobaltferrite nanoparticle sizes within the ferrofluid, as obtained by TEM, with the scale bar being 50 nm). From simultaneous fits to AC susceptibility and DC magnetization data, the average hydrodynamic diameter was determined to be about 72.5 nm. Particularly, as illustrated in FIG. 8B, showing a graph depicting AC susceptibility and de-magnetization curve of the ferrofluid, a fit to the ac susceptibility data assuming a log-normal size distribution indicates moderate particle aggregation with a mean hydrodynamic diameter of 72.5 nm. The discrepancy between the average hydrodynamic diameter and the individual core sizes observed in TEM images points to a certain degree of particle aggregation within the colloidal suspension of the ferrofluid. This finding was also confirmed through dynamic light scattering measurements, which yielded an average hydrodynamic diameter of about 64.9 nm on highly diluted samples of ferrofluid. Nevertheless, compared with the µm-sized microspheres and cells, the magnetic nanoparticles were still small enough to approximate the ferrofluid as a continuous magnetic medium.

During synthesis, it was determined that the optimum ionic concentration within the ferrofluid to provide a good compromise between cell viability (as determined by the trypan blue test) and ferrofluid stability was about 40 mM. Particularly, with reference to FIG. 8C, a chart depicting live cell count vs. citrate concentration is provided. As shown in the chart, 40 mM citrate concentration (stabilized with citric acid to yield a pH of 7.4) was found to be optimum for cell viability and ferrofluid stability combined. The dashed line shows the cell count in the original blood sample. Count 3 corresponds to cells spending ≈1 h in the citrate solution. During the course of a given experiment, cells retained their viability. It was observed that 75% of cells remained viable, even after being suspended in the ferrofluid for several hours, enabling extended tests involving live cell manipulation and separation.

Before the cell manipulation experiments, the ferromicrofluidic devices used fluorescent polystyrene microspheres (Duke Scientific; monodisperse sets with diameters ranging from 1.2 to 9.9 µm). To understand the influence of excitation frequency and current amplitude on the behavior of nonmagnetic microparticles dispersed in ferrofluid, a series of experiments were performed using different sizes of microspheres at various excitation frequencies and current amplitudes. Microspheres of a given size were mixed with the ferrofluid in small quantities (up to $1.1 \times 10^6$ microspheres per mL for the smallest microparticle diameter) and subsequently added to the microfluidic channel. The channel inlet and outlet were clamped at both ends to prevent transient fluid motion. Microspheres near the roof of the microchannel were imaged from above with an upright fluorescent microscope (Zeiss AxioImager A1) and a high-sensitivity video camera (Retiga 2000R) using StreamPix software. Image analysis was performed offline in MATLAB (MathWorks) via an optical flow procedure. The procedure could automatically track the trajectory and determine the size of thousands of individual microspheres within the field of view in less than one (1) minute.

Figure 9A:
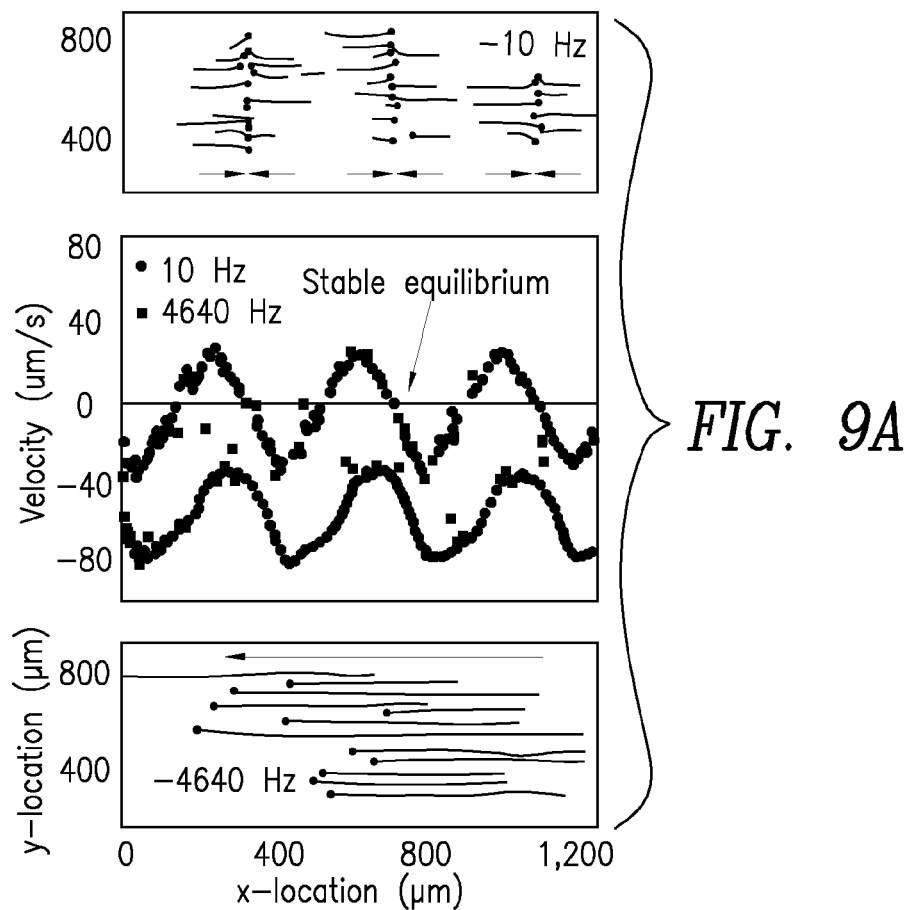
FIGS. 9A-B include graphs showing the behavior of particles in a ferrofluid in the presence of a magnetic field.
Figure 9B:
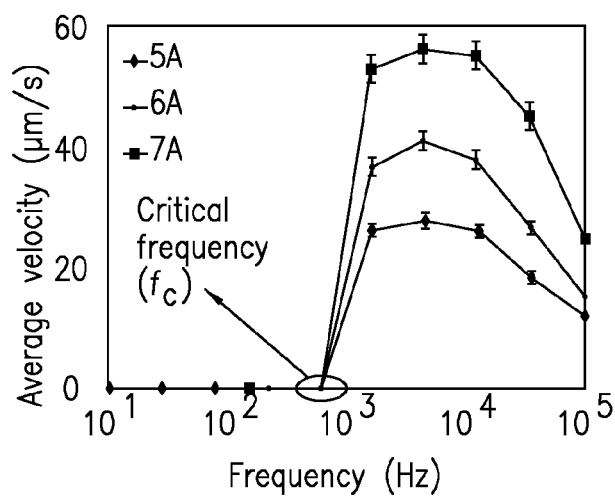

During these experiments, two types of particle dynamics were observed. At low frequencies, the microspheres localized between the electrodes, where repulsive forces caused by magnetic field gradients form local minima. With reference to FIG. 9A, frequencies above a critical value $f_c$, led to continuous translation of the microspheres along the length of the channel roof. This critical frequency depended on particle size and electrode spacing, but not necessarily on input current amplitude (FIG. 9B). The average velocity of microspheres of a given size depended on the excitation frequency, current amplitude, and their location with respect to the underlying electrodes.

Particularly, FIGS. 9A and 9B demonstrate particle velocity as a function of input frequency and current amplitude. In FIG. 9A, the middle graph shows a spatial distribution of instantaneous average x-velocities for 6-pm-diameter particles at 7-A input current amplitude (peak to peak) at two different frequencies. Because of repulsive forces from magnetic field gradients, microparticles either slow down or completely stop in between electrodes. Zero crossings with negative slope correspond to stable equilibrium points (i.e., particle trapping). The top graph of FIG. 9A shows, at 10 Hz, particle trajectories terminating in between electrodes, resulting in trapping. The bottom graph of FIG. 9A shows, at 4,640 Hz, particles moving continuously throughout the length of the channel. This is the regime where magnetic torque from the locally rotating component of the traveling wave dominates over the repulsive forces. The black dots at the end of each trajectory indicate where particles eventually stop. FIG. 9B shows that above a critical frequency ($f_c$), the 6-μm microspheres roll continuously along the top channel surface without getting trapped.

Figure 10B:
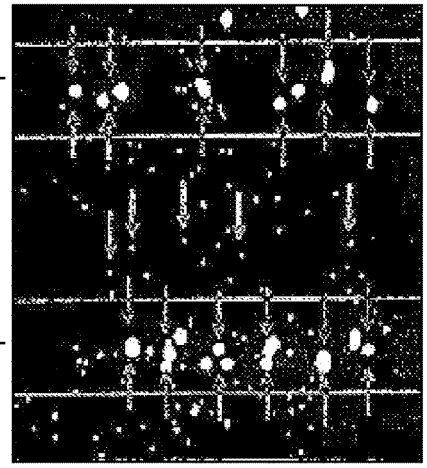
FIGS. 10A-D include graphs and diagrams showing the behavior of particles in a ferrofluid in the presence of a magnetic field.
Figure 10D:
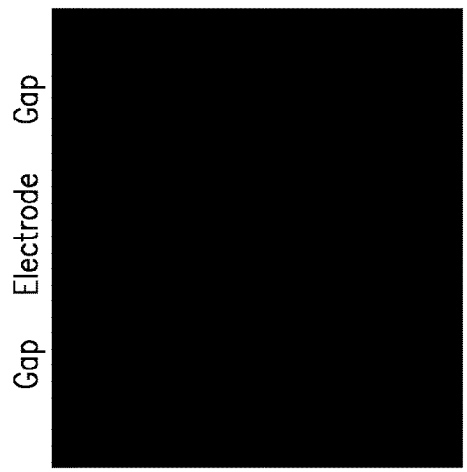
Figure 10A:
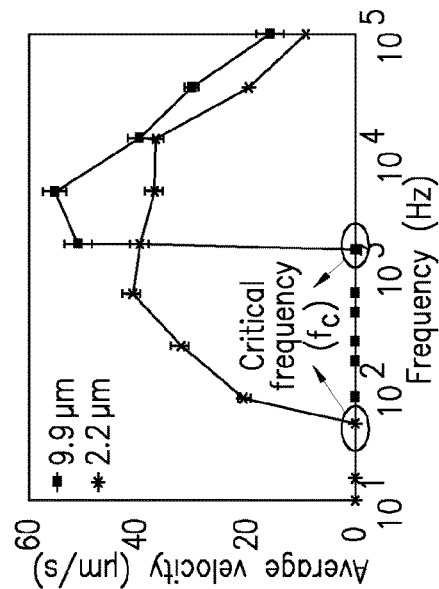

FIGS. 10A-10D illustrate frequency-dependent particle separation. In experiments with various microsphere diameters, a monotonic increase was found in critical frequency with increasing particle size, demonstrating the potential for size-based particle separation through excitation frequency control. FIG. 10A depicts the particle size dependence of critical frequency ($f_c$). Discrete $f_c$ values for different diameters of particles enable size-based separation by tuning to the right frequency. This phenomenon may be explained through a simple hydrodynamic reasoning. Both magnetic force and torque scale with particle volume ($R^3$); the hydrodynamic drag that resists linear particle motion scales with R against force and $R^2$ against torque that rolls the particle. Hence, linear particle velocity caused by magnetic force alone depends on $R^2$, whereas that caused by torque scales with R. This observation indicates that torque effects on smaller particles are relatively more significant and explains why smaller microparticles can overcome the repulsion of magnetic force traps and propagate continuously within the channel at lower frequencies. The solid curve depicted in FIG. 10A represents simulation results for critical frequency and explains the data very well for an average microsphere-wall gap of nm (1 nm) and no-slip conditions applied to the rotation of the microspheres.

Figure 10C:
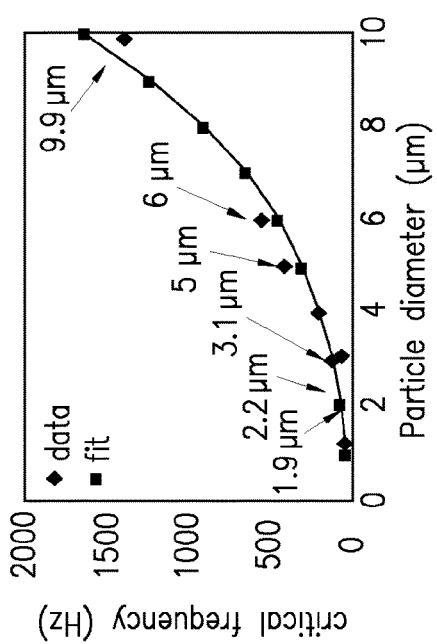

FIG. 10B shows the average velocity (also referred to as manipulation speed) of 2.2- and 9.9-μm microspheres (mixed in an 8:1 ratio within the same ferrofluid) under excitation frequencies ranging from 10 Hz to 100 kHz. As depicted in FIG. 10B, the 2.2- and 9.9-μm particles can be separated at 400 Hz. For a wide frequency range, the smaller particles translated continuously, whereas the larger particles were trapped between the electrodes. In this particular experiment and others, a mixture of particles/cells was eventually separated into two groups, e.g., those trapped vs. those cleared from channel. Assuming that the target particles/cells are those that are intended for trapping, the trapping efficiency can be defined as the ratio of the number of target moieties within the trapped group to their corresponding number in the initial mixture. Similarly, separation efficiency is defined as the ratio of the number of non-target moieties within the cleared group to their corresponding number in the initial mixture. However, particle/cell purity is simply the ratio of the number of target cells within the trapped group to the total number of cells in that group. At an excitation frequency of 400 Hz, 96.5% of the 9.9-μm microspheres (167 of 173) were trapped within 10 s, whereas the 2.2-μm particles (1,285 of 1,294) continued to translate along the channel and were cleared out of the observation window (45 s) without being trapped (as illustrated in FIGS. 10C and 10D) with a 99.3% separation efficiency. The particle purity in the trapped group was 94.9% (167 targets of 176 total trapped particles). Most of the small microspheres that failed to clear the channel were stuck on the polydimethylsiloxane (PDMS) wall in random locations, instead of being trapped between the electrodes. With better channel preparation, the separation efficiency and particle purity can be even higher.

FIG. 10C is a fluorescent microscopy image from a section of the microfluidic channel containing 2.2- and 9.9-μm microspheres randomly dispersed within the channel right before the excitation. Vertical lines indicate electrode borders. FIG. 10D is a snapshot of the channel from the same location as in FIG. 10C, 45 seconds after the excitation (6 A peak to peak, 400 Hz) is turned on. The 9.9-μm particles quickly localize within the nearest spacing between electrodes, whereas 97% of the 2.2-μm microspheres continuously travel from right to left without being trapped. Almost all of the smaller microspheres within the field of view in FIG. 10D have entered from the right as a fresh batch.

Figure 11B:
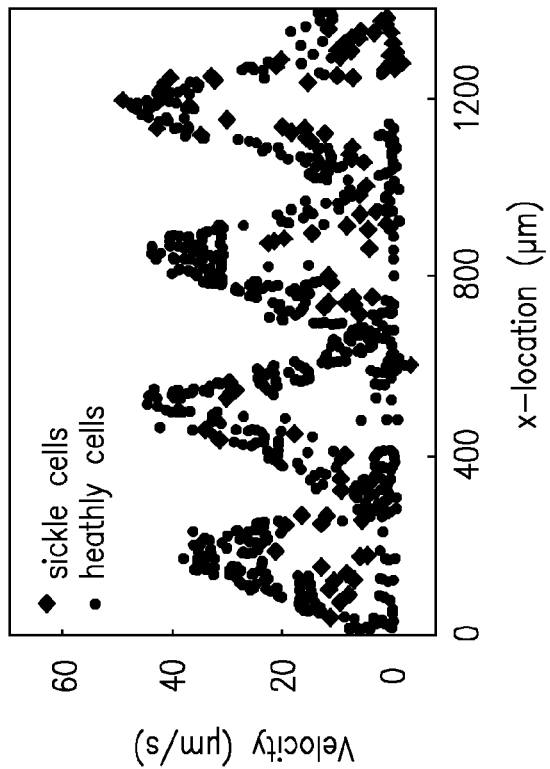
FIGS. 11A and 11B are graphs depicting cellular separation for various target species.
Figure 11A:
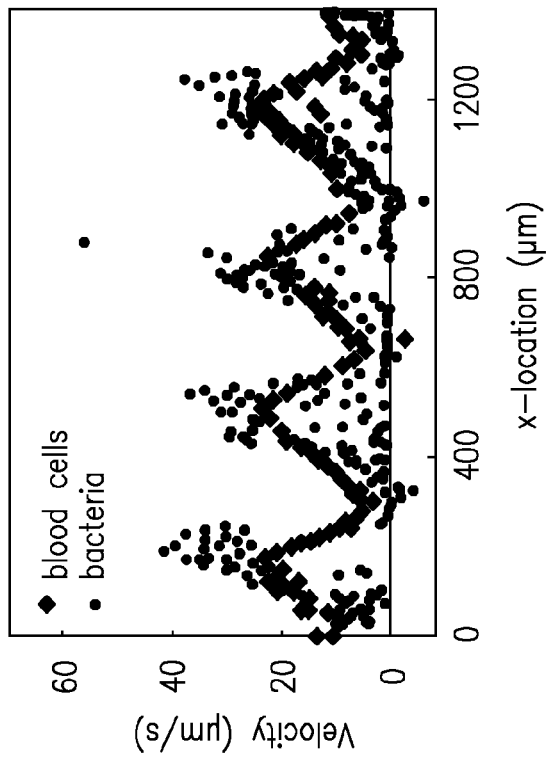

FIGS. 11A and 11B depict cellular separation with bacteria and blood cells. FIG. 11A depicts the spatial distribution of x-velocities at 200 Hz in a sample containing *E. coli* bacteria and red blood cells. At this frequency, most red blood cells are trapped between the electrodes (indicated by their zero local speeds), whereas *E. coli* can slowly but continuously move through that region. Fluctuations in the red blood cell data are statistical in nature, as explained herein. FIG. 11B depicts sickle cell separation. Sickle cells, which have an elongated shape and altered elasticity compared with normal red blood cells, are trapped and concentrated between the electrodes, whereas the healthy cells are still able to circulate within the microfluidic channel at 300 Hz. Electrode spacing of the device in FIG. 11A is different from that in FIG. 11B, resulting in different $f_c$'s for red blood cells within each channel.

Figure 12A:
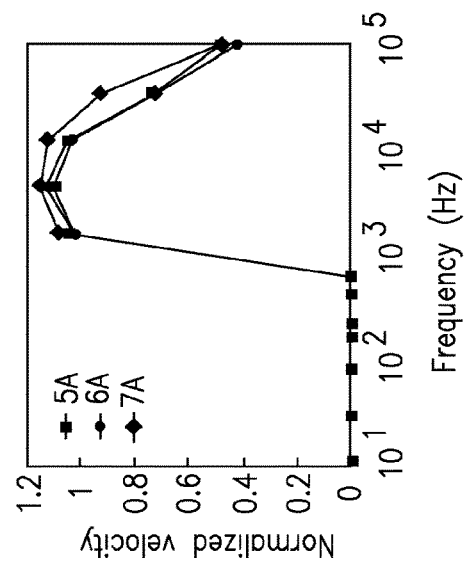
FIGS. 12A-C include graphs and diagrams showing the behavior of particles in a ferrofluid in the presence of a magnetic field.
Figure 12B:
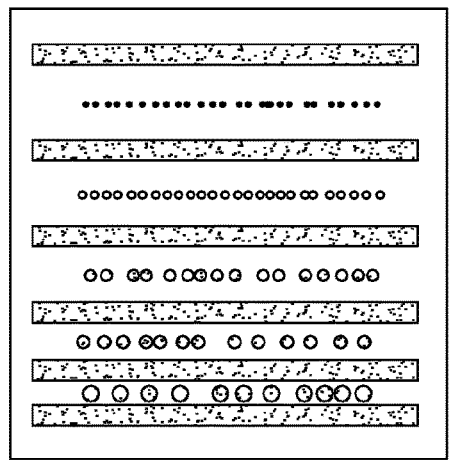
Figure 12C:
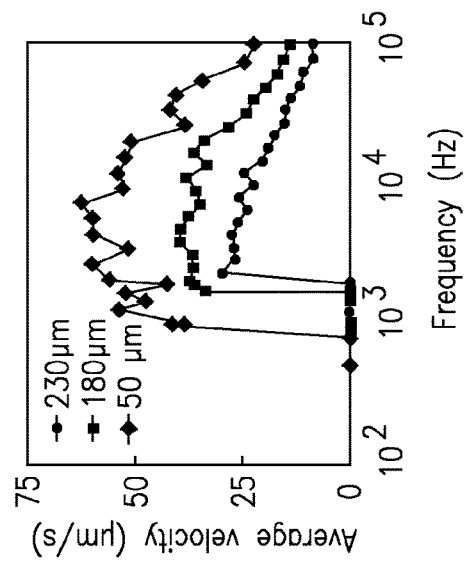

FIG. 12A depicts microparticle average speed, normalized by the square of the current amplitude (peak-to-peak) and to the maximum value at 12 A, depicted as a function of excitation frequency. Particle velocities are proportional to the square of current until about 7 A. FIG. 12B depicts the average velocity vs. frequency at 6 A peak-to-peak for 9.9 pm microspheres travelling over electrodes with different spacing. A smaller spacing leads to higher particle velocity and a smaller critical frequency. FIG. 12C depicts a conceptual sketch of a microparticle sorter based on the effect observed in FIG. 12C. At a given excitation frequency, smaller spacings trap larger particles, while letting smaller ones pass through. Eventually, even the smallest particles can be trapped in the larger gaps. Here, it is assumed that particles move from left to right, and the channel over the electrodes depicted is initially cell-free.

Thus, particle motion was determined to depend on electrode spacing, with a smaller spacing leading to faster microsphere travel and a reduction in critical frequency (see FIG. 12B). This phenomenon may be used in a device featuring regions of electrodes with different gaps to use the same excitation frequency to separate particle mixtures with more than two distinct sizes. An electrode pattern may also be created with a gradually increasing gap to sort particles based on size (as illustrated, for example, in FIG. 12C). In this context, it was observed that small nonuniformities in actual electrode spacing (caused by fabrication) partly determined the resolution of separation, defined as the minimum size difference in particles that can still be separated with high efficiency (e.g., >90%). Given a range of particle sizes, this resolution of separation is directly related to the difference in the corresponding critical frequencies. Under ideal conditions (i.e., perfectly controlled electrode gaps and a very diluted cell concentration), the resolution of separation could be arbitrarily small. However, critical frequencies tend to show slight local variations around each nonuniform electrode gap. As depicted in FIG. 10A, the optimal critical frequency depends nonlinearly on the particle radius. Thus, a 1-μm difference in diameter between 9- and 10-μm microspheres is easier to resolve (with slight random variations in electrode spacing) than one between I- and 2-μm particles. Ultimately, the resolution of separation that was achieved in the experiments described herein was ≈1 μm for particles 2 μm or larger.

Example 2: Effects of Current Amplitude on Microparticle Speed

In additional experiments, the dependence of microparticle manipulation speed as a function of input current amplitude was investigated and determined. According to computations outlined in herein, and assuming the ferrofluid remains magnetically linear, the particle speed scales with the square of the input current. As illustrated in FIG. 12A, this assumption begins to break above 7 A peak-to-peak input current amplitude.

Electrode spacing was also varied (with electrode width fixed at 210 μm) to determine its effect on particle manipulation. A smaller electrode spacing resulted in faster average particle speeds and lower critical frequencies (as illustrated in FIG. 12B). This observation could be explained by noting that electrodes spaced closer reduce the local magnetic field gradient that produces the magnetic force on the microparticles. Closer electrodes also pack more energy into the fundamental of the travelling wave that produces the magnetic torque on these microparticles. A lower magnetic force and a higher torque result in faster microparticle rotation and overall travel speed. They also result in the critical frequency being lowered (Tung L D, et al. (2003) Magnetic properties of ultrafine cobalt ferrite particles. *J Appl Phys* 93:7486-7488). This observation further supports the idea of using a microparticle sorting device in which the spacing between the electrodes could be gradually increased to trap increasingly smaller particles or cells (as illustrated in FIG. 12C).

Example 3: Separation of Live Cells

Based on the physical behavior of the ferromicrofluidic platform, manipulation and separation experiments were conducted with live human red blood cells and bacteria to demonstrate the utility and practicality of the ferromicrofluidic systems and devices described herein for biomedical applications. Red blood cells and *Escherichia tali* bacteria [K12 strain (Blattner et al., 1997, *Science* 277:1453-1474)] were stained with a green fluorescent marker and mixed before suspension in ferrofluid. The average velocity for cells and bacteria within the channel was measured with 6 A of peak-to-peak current amplitude for frequencies from 10 Hz to 100 kHz. The critical frequencies for cells and bacteria were found to be 215 and 77 Hz, respectively. These $f_c$ values are somewhat lower than those found for comparably sized polystyrene microspheres, likely due to a combination of compliant shapes and nonspherical geometries that lead to increased difficulty of rolling along the channel roof. Moreover, bacteria and cells, with their complex surface chemistries, interacted with the PDMS channel more strongly (resulting in more prevalent cellular attachment) than the bare microspheres, indicating potentially higher effective kinetic friction coefficients between the cells and the PDMS surface. With reference again to FIG. 11A, the spatially averaged linear velocity of cells and bacteria along the channel for an excitation frequency of 200 Hz is illustrated. The smaller *E. coli* moved continuously along the channel (velocity points in FIG. 11A do not cross zero) and eventually left the observation window, whereas blood cells were localized between electrodes (velocity points reach zero). It is to be noted that the larger variation observable in the red blood cell data of FIG. 11A stems from a statistical fluctuation: there are only a few red blood cells that passed through a given x-location during the observation window, and their nonspherical shapes mean that each cell would be at a random angular orientation (and slightly different instantaneous velocity) as it rolled down the channel at that location. Bacteria, although varying in length and nonspherical, had enough numbers (several hundred through a given x-location) to result in good average statistics. In the end, ≈6,750 of the 7,050 *E. coli* bacteria initially present within the field of view of the sample were cleared (95.7% separation efficiency) within 45 s. Of the 1,018 red blood cells initially present, 954 were trapped, corresponding to a trapping efficiency of 93.7% and cell purity of 76.1%.

In a different experiment, healthy red blood cells were separated from those afflicted with sickle cell anemia by exploiting the shape and elasticity differences between them (as illustrated in FIG. 11B). A blood sample containing approximately a 4:1 ratio of healthy-to-sickle red blood cells was added to the ferrofluid and introduced into the microchannel. At 300 Hz, sickle cells were trapped, whereas the healthy blood cells were cleared continuously from the channel (fluctuations in each dataset depicted in FIG. 11B are statistical in nature). In a sample initially containing 501 healthy red blood cells and 145 sickle cells, 300 healthy cells were cleared, whereas 109 sickle cells were trapped. Assuming that the goal is to clear the sample from sickle cells, these numbers correspond to a separation efficiency of 75.2% (109 of 145 sickle cells were separated from healthy ones) and a healthy cell purity of 89.3% (300 healthy cells and 36 sickle cells were cleared).

These examples demonstrate the use of ferro-microfluidies in significantly reducing incubation times and increasing diagnostic sensitivity in cellular assays through rapid separation and selective delivery of target cells to sensor arrays. While manipulation and separation of microparticles and live cells within microfluidic devices is also possible through established techniques (such as DEP and magnetic label-based methods), the ferromicrofluidic approach described herein offers numerous advantages over existing methods. For example, target cells can be concentrated, trapped, localized, or simply directed toward sensor surfaces efficiently, rapidly, and in a label-free fashion. The biocompatible ferrofluid of the present disclosure can sustain live blood cells for several hours without deterioration in physical properties, allowing extended examination of the target sample.

When combined with a simple photodiode, ferromicrofluidic separation of cells can provide a rapid, automated, and disposable blood assay that can count and estimate the concentration of any target cell type (such as bacteria or sickle cells) within, for example 1 minute, without the need for a microscope, pumps, or lengthy sample preparation steps. The systems, devices, and methods described herein can also be used to selectively concentrate rare cells, such as circulating tumor cells in blood samples, by exploiting the differences in Young's modulus of the subject cell types (Lekka et al., 1999, *Eur Biophys J* 28:312-316). Applied in this manner, the systems, devices, and methods described herein can increase detection sensitivity of existing cellular assays.

The systems, devices, and methods described herein thus include a cellular manipulation and separation platform using biocompatible ferrofluids within low-cost microfluidic devices. It was demonstrated that highly efficient particle separation is achievable in less than one (1) minute. As an example, bacteria can be separated from live blood cells, and sickle cells can be separated from healthy red blood cells. In the case of a flow-based device, separation can be achieved with particle manipulation perpendicular to the flow direction. By varying electrode geometry and input excitation frequency, the systems, devices, and methods described herein can be tailored for different size ranges of particles and cells. Together with control of microchannel surface chemistry, the systems, devices, and methods described herein can be integrated within lab-on-a-chip sensors and diagnostic systems to direct target cells toward active regions. In this manner, the systems, devices, and methods described herein can significantly reduce incubation times and increase the practical detection sensitivities achieved in existing sensors and diagnostic platforms.

2. Target Species Focusing

As noted, also described herein are systems, devices, methods, and other implementations, including a device to focus at least one target species suspended in a biocompatible ferrofluid that includes a microfluidic channel configured to receive a sample containing the at least one target species and the biocompatible ferrofluid, with the at least one target species in the received sample being substantially concentrated in an input flow with an associated input width. The device further includes at least two of electrodes positioned proximate the microfluidic channel, the at least two electrodes configured to generate controllable magnetic forces in the sample containing the ferrofluid when controllable electrical currents are applied to the at least two electrodes, the generated controllable magnetic forces causing the at least one target species to be focused in a resultant flow having a width narrower than the input width associated with the input flow. In some embodiments, the generated magnetic forces may be controlled through controlled application of at least current to the electrodes (i.e., in a manner similar to that described in relation to controlling the magnetic field used to enable discrete separation of a plurality of target species).

As described herein, an advantage of the microfluidic channel and electrode technology is its ability to focus and concentrate cells into a single-file formation at the channel ceiling. Thus, high precision can be achieved with this capability, because of the underlying micro-patterned electrodes. Some degree of focusing can also be achieved using magnetic fields from an external permanent magnet. Pushing the cells towards the channel ceiling while focusing them makes it easy to detect, count and capture them.

As will be described in greater details below, there are at least three ways in which cellular focusing can be achieved in ferro-microfluidic devices using different electrode geometries: (i) at least two parallel electrodes carrying DC or AC currents (in various relative phases) along the length of the channel will push the cells into the space above the gap between them; (ii) at least two sets of electrodes carrying traveling magnetic fields in opposite directions can roll the cells into the border between each set; (iii) An array of electrodes carrying DC or AC currents (in various relative phases, including those that result in traveling fields) with gradually decreasing gaps between neighbors will push and keep the cells within those gaps, until the gaps become small enough for magnetic torque effects to become prominent. The first two approaches can be used to focus a stream of target cells in the vicinity of a detector/counter, whereas the third approach is ideal for realizing massively parallel focusing and subsequent separation of the input sample. Specifically in the third approach, the target species (e.g., cells) would first be focused into alternating capture gaps, and the target cells would then be separated into the neighboring gaps.

Advantages of cellular focusing implemented using the electrodes and microfluidic channel configurations are as follows:

Because very efficient focusing can be achieved without hydrodynamic sheath flow, the entire volume of the device can be dedicated to the input stream of cells. Thus, a higher throughput can be achieved with the implementations described herein as compared to existing approaches that use hydrodynamic focusing.

By focusing the input cell stream into every other electrode gap, target species (e.g., cells or pathogens) can be separated into the adjacent gaps. This ability enables achieving a dramatic parallelism in the separation and sorting functionalities, because the device can feature dozens of such electrode patterns arrayed across the width of the flow channel.

When the cells are lined up in single file in the vicinity of the channel ceiling, they can be easily detected (through a variety of ways, including, for example, optical, magnetic, electrical impedance and capacitance measurements) and counted. In this fashion, the implemented systems/devices can serve as "nanocytometers", able to separate and count up to millions of cells in a few minutes. The systems/devices can be used as a pathogen detector, or can be used help characterize the concentrations of other non-target cells (such as CD4's, red blood cells, platelets, etc.).

Figure 13:
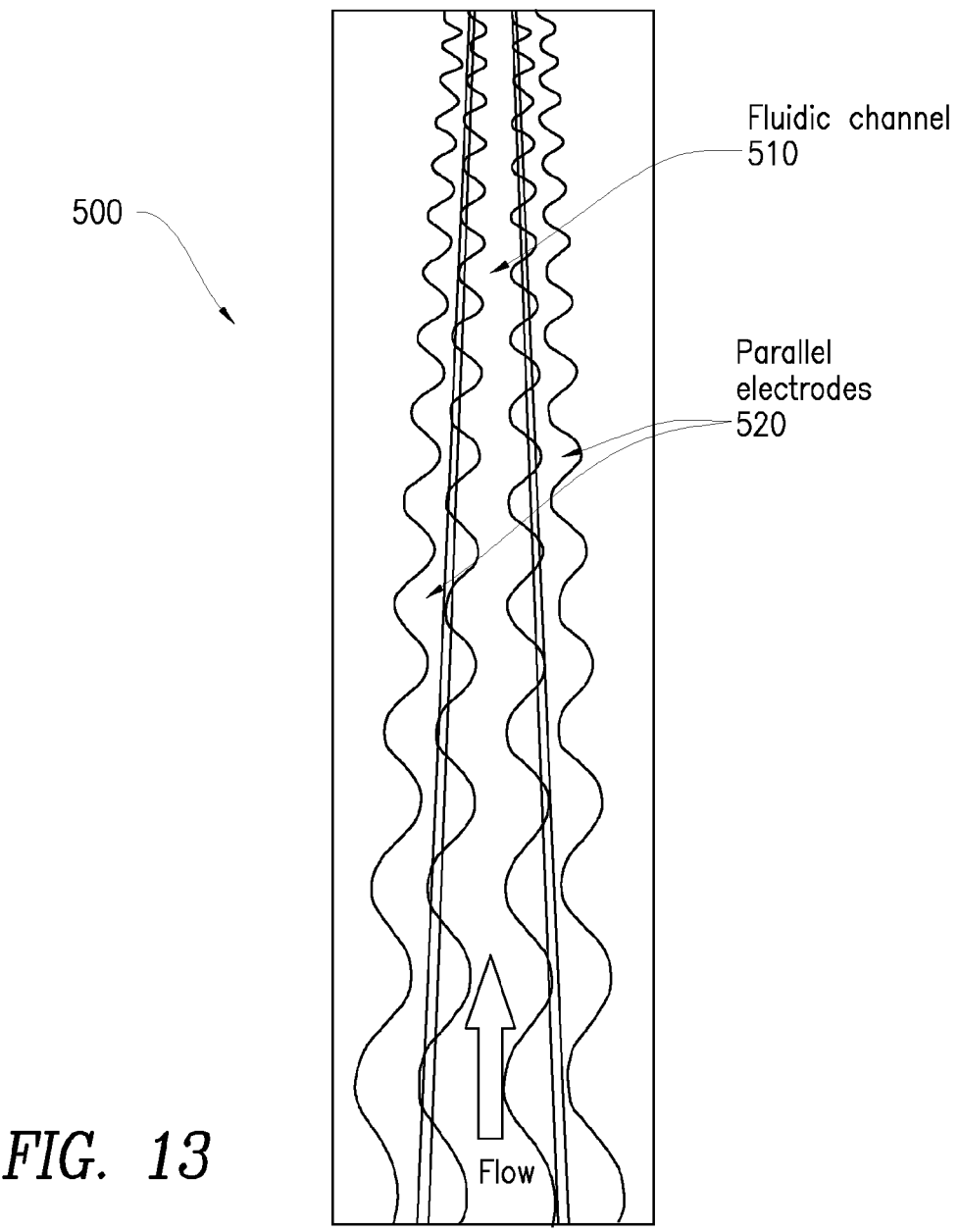
FIG. 13 is a schematic diagram of a microfluidic device that includes an electrode set configured to generate a magnetic field to focus target species of a sample onto a substantially single file stream.

With reference to FIG. 13, a schematic diagram of a microfluidic device 500 that includes an electrode set configured to generate a magnetic field to focus target species of a sample onto a substantially single file stream is shown. The device 500 includes a microfluidic channel device 510 and a set of electrodes 520. The microfluidic channel 510 may be similar to the microfluidic channels described in relation to FIGS. 1A, 4 and 5. The set of electrodes 520 includes, in the example embodiment of FIG. 13 includes two "wiggly" electrodes that are generally substantially parallel to each other. Upon application of a controllable at least one current to the set of electrodes, a magnetic field is generated that causes the target species suspended within the ferrofluid to be pushes and focuses within the microfluidic channel. The controllable at least one current applied to the electrode(s) may be controlled/regulated using a controller such as the controller 160 of FIG. 1A (which may be a processor-based controller).

In some implementations, the at least two electrodes (such as the electrodes 520) may include a structure having at least one of, for example, a substantially straight shape of one or more of the at least two electrodes, a substantially wavy shape of the one or more of the at least two electrodes, a substantially parallel arrangement of the at least two electrodes, and/or a substantially tapering orientation of the at least two electrodes in which the at least two electrodes gradually approach each other.

In some embodiments, the set of electrodes are configured to generate a magnetic field, upon application of the at least one current thereon, that is applied to the target species substantially at the inlet area of the microfluidic device. In such embodiments, multiple electrodes sets may be used with the microfluidic device, with one set acting to focus a sample including at least one target species into a single file formation that flows through the microfluidic channel, and another electrode set whose main purpose is to implement discrete separation (e.g., for continuous flow of a ferrofluid-based) sample to enable separating two or more different target species in the manner described in relation to, for example, FIGS. 1-7.

In some implementations, magnetic force focusing at the inlet of a microfluidic device can lead to rapid sorting of cells into capture gaps defined in the microfluidic device (e.g., in the channel of the device). Such focusing functionality can therefore be used to first focus target species (e.g., target cells) into alternating capture, and the target cells can then be separated into neighboring gaps.

Figure 14:
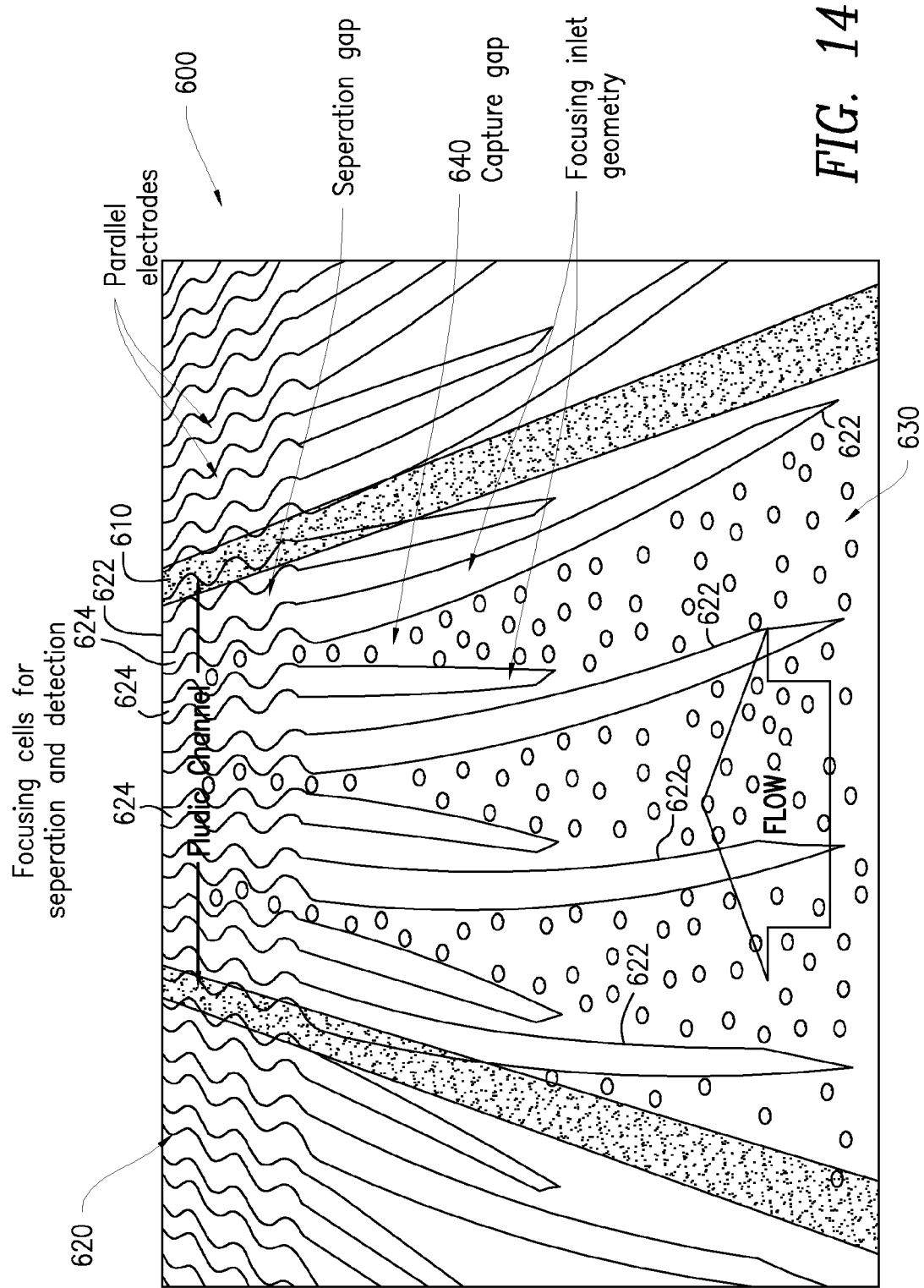
FIG. 14 is a schematic diagram of a part of another example microfluidic device configured to enable focusing of target species into alternating gaps.

Thus, with reference to FIG. 14, a schematic diagram of a part of another example microfluidic device 600 configured to enable focusing of target species into alternating gaps is shown. The device 600 includes a fluidic channel 610 which may be similar to the microfluidic channels described in relation to FIGS. 1A, 4, 5 and 13. The device 600 further includes a set of electrodes with multiple electrodes 620 that includes at least two types of electrode geometries. In the example of FIG. 14, one of every two adjacent electrodes (defining a pair of electrodes) has a length that extends substantially into an inlet region 630 of the device to thus define focusing electrodes 622. Adjacent to each such focusing electrode 622 are shorter electrodes 624. In some embodiments, a pair of electrodes that includes a focusing electrode 622 and a shorter electrode 624 with those electrodes being arranged in a substantially tapering orientation relative to each other such that they approach each other may be used. The plurality of electrodes 620 (including the focusing electrodes and the shorter electrodes) have a wiggly shape from a point in the microfluidic channel that is past the inlet stage, and extending towards the outlet region of the device. From the spatial position where the plurality of electrodes 620 assumes a generally wiggly shape, the electrodes generally extend, in some embodiments, in a substantially parallel direction to each other.

With the example geometry of the electrodes depicted in FIG. 14, upon application of at least one current to the plurality of electrodes 620, the geometry of the electrodes at around the inlet region causes a magnetic field is generated that causes the target species to be directed to multiple single file streams focused in alternating capture gaps (that include the capture gap 640 depicted in FIG. 14) defined by pairs of electrodes. Once flow streams (each of which may include similar mixtures of the target species received at the inlet of the device) are formed, a magnetic field acting on the now focused multiple sample streams causes separation of different target species into the neighboring gaps (i.e., the gaps that did not receive any of the target species as a result of the focusing operation). The magnetic field formed at the area of the fluidic channel where the electrodes 620 are substantially parallel, and which operates to perform the discrete separation operation, may have different (or similar) attributes than the magnetic field at around the inlet region. The discrete separation operation performed by the magnetic field present where the electrodes 620 are substantially parallel is similar to the operations performed by the systems, devices, and methods described in relation to FIGS. 1-12.

Thus, in some implementations, a device may include an array of electrodes with at least some first electrodes of the array being arranged in a substantially tapering orientation relative to neighboring electrodes such that the first electrodes are configured to gradually approach neighboring electrodes. The array of electrodes is configured to generate magnetic forces to cause resultant flows of the at least one target species to form above and between pairs of neighboring electrodes. Every gap between pairs of electrodes is therefore generally empty after the focusing operation, but upon performing the separation operation on the flow streams, the empty gaps receive at least one of the target species being separated from the mixtures flowing in the neighboring gaps into which the mixtures have been focused.

Other electrode geometries, different from those depicted in FIGS. 13 and 14, may be used to enable focusing functionality.

Figure 15:
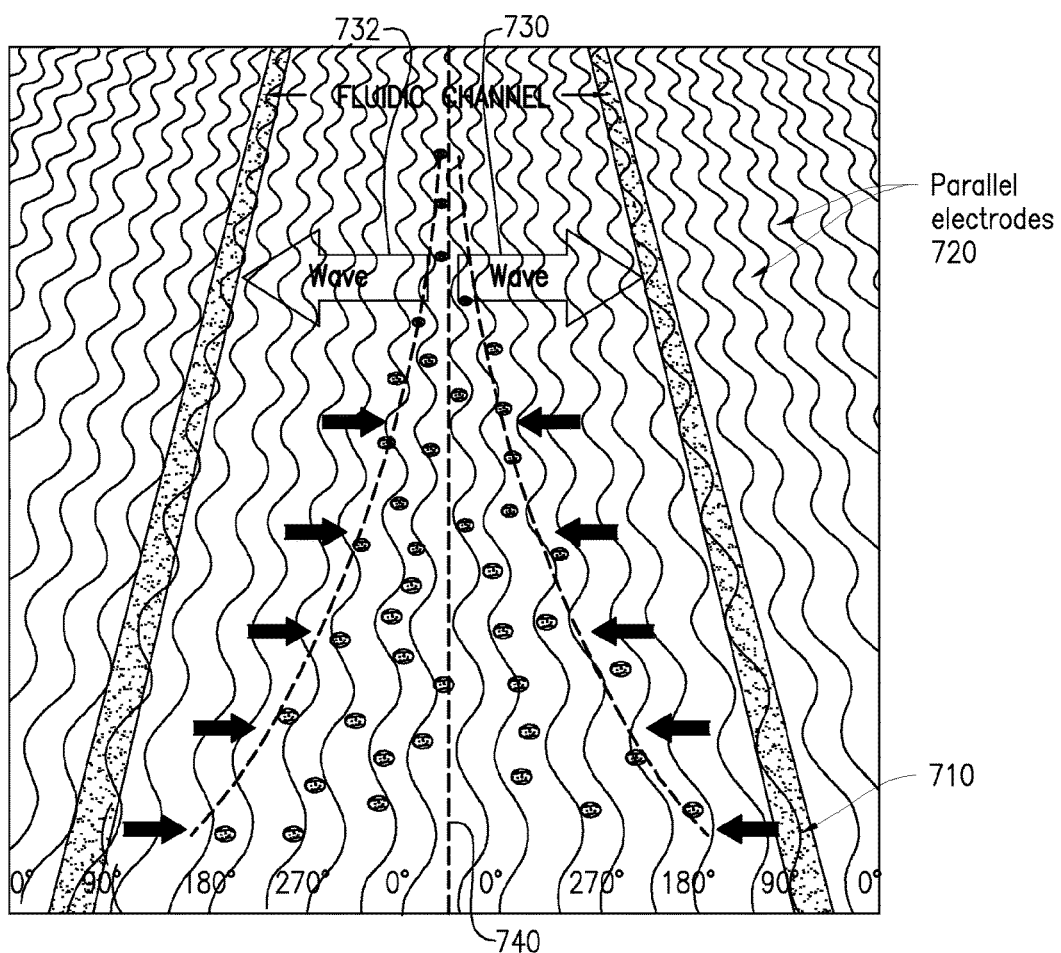
FIG. 15 is a schematic diagram of part of another example embodiment of a microfluidic device.

In some embodiments, the electrodes used to perform the focusing operation are configured to generate at least two magnetic waves of reverse traveling fields to cause the at least one target species to be focused at about a center of a boundary between the at least two generated magnetic waves. With reference to FIG. 15, a schematic diagram of part of another example embodiment of a microfluidic device 700 is shown. The device 700 includes a fluidic channel 710 which may be similar to the microfluidic channels described in relation to FIGS. 1A, 4, 5, 13, and/or 14. The device 700 further includes a set of electrodes with multiple electrodes 720 that, in the embodiments of FIG. 15, have generally wiggly shapes, and have a substantially parallel orientation relative to each other. The electrodes 720 are positioned proximate to the microfluidic channel 710. For example, the electrodes 720 may be arranged in an electrode layer positioned outside the microfluidic channel.

Upon application of a controllable at least one current to the electrodes of FIG. 15, two magnetic waves of reverse traveling fields (marked as wave 730, and 732) are generated. The two magnetic waves of reverse traveling fields cause the target species in the sample flow to be focused at about a boundary 740 (depicted as a dashed line) between the two generated magnetic waves.

Other electrode configurations may be used to generate magnetic fields (and thus magnetic forces) used to focus target species in a sample. In some embodiments, at least two electrodes configured to generate a magnetic field used to perform the focusing functionality may conduct controllable AC current(s) with controllable attributes determined to implement a desired focusing function. In some embodiments, at least two such electrodes may conduct DC current. In some embodiments, a single electrode may be wrapped around itself to form two (or more) parallel legs that define multiple electrode portions used to generate a focusing magnetic field. In some embodiments, a set of one or more permanent magnets may be used in addition to, or instead of, the electrodes set to facilitate implementing the focusing functionality.

Figure 16:
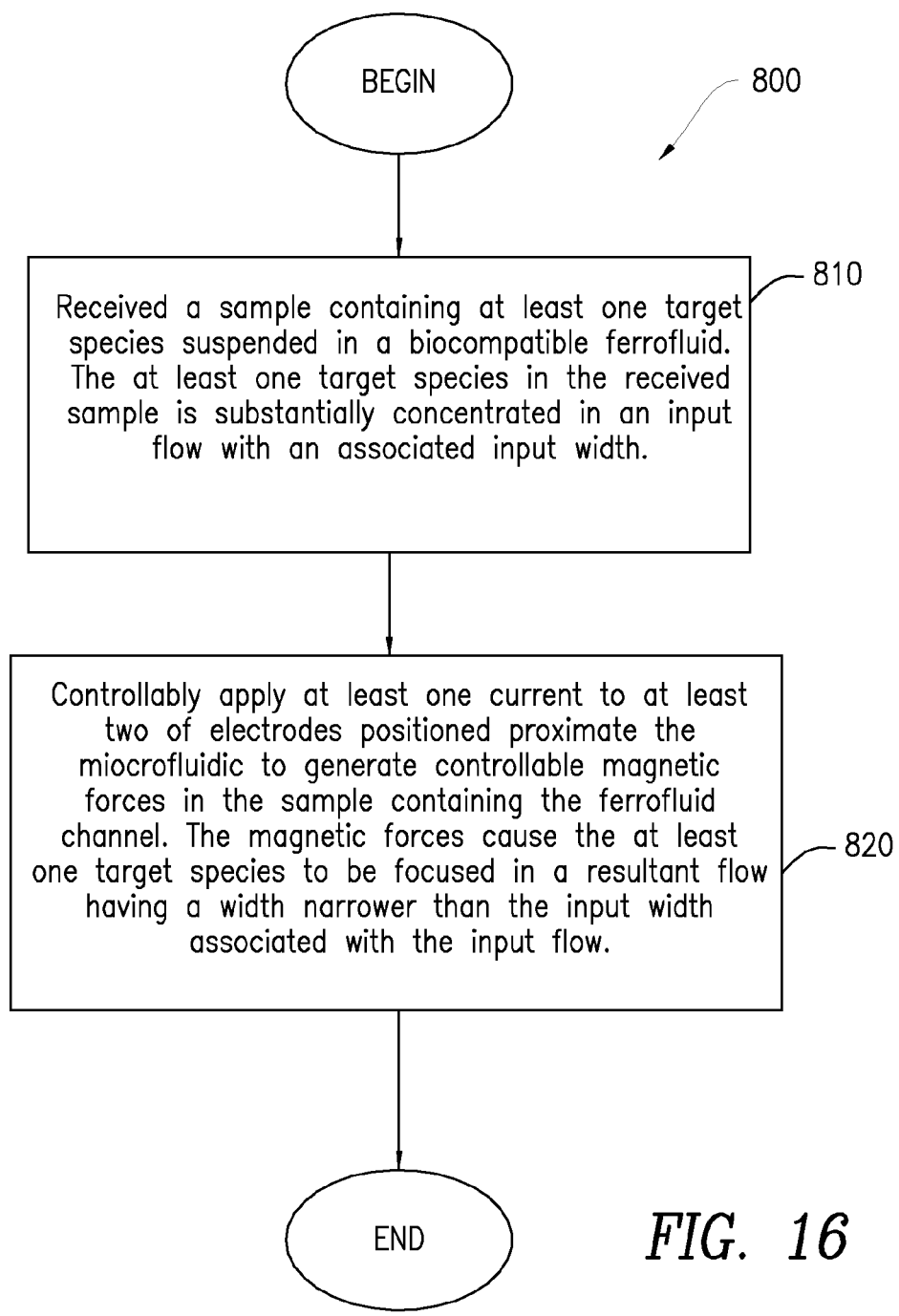
FIG. 16 is a flowchart of an example procedure to focus target species in a microfluidic channel.

With reference to FIG. 16, a flowchart of an example procedure 800 to focus target species in a microfluidic channel is shown. The procedure 800 includes receiving 810 a sample containing the at least one target species suspended in a biocompatible ferrofluid, with the at least one target species in the received sample being substantially concentrated in an input flow with an associated input width.

Having received the sample, at least one current (e.g., AC currents with controllable frequencies, phases, and/or amplitudes, DC currents, etc.) is controllably applied 820 to at least two electrodes positioned proximate the microfluidic to generate controllable magnetic forces in the sample containing the ferrofluid channel. The magnetic forces cause the at least one target species to be focused in a resultant flow having a width narrower than the input width associated with the input flow. In some embodiments, the at least two electrodes are configured to conduct the controllably supplied currents and to generate the controllable magnetic forces according to, for example, attributes of the applied current(s), attributes of the microfluidic channel, and/or attributes of the at least two electrodes (such as their structure or shape).

3. Magnetic Forces to Direct Target Species to a Detector

As previously noted, also described herein are devices, systems, methods, and implementations, including a device to detect at least one target species in a sample, with the device including a microfluidic channel configured to receive the sample containing the at least one target species and a biocompatible ferrofluid in which the at least one target species is suspended, a detector to determine the at least one target species in the sample, and at least two electrodes positioned proximate the microfluidic channel, the at least two electrodes configured to generate controllable magnetic forces in the sample containing the ferrofluid when a controllable electrical at least one current is applied to the at least two electrodes. The generated controllable magnetic forces cause the at least one target species to be directed towards the detector. Because the efficacy and quality of detecting target species depends, at least in part, on the vertical distance of the target species to the electrodes, if the vertical distance cannot be controlled, the different types of target species may not reliably be distinguished. Accordingly, by pushing target species to the ceiling (near where the detection mechanism may be positioned), challenges hindering successful detection of target species as a result of the vertical distance of the target species to the detectors can be controlled and, to an extent, overcome.

The detection scheme described herein involves, in some embodiments, direct electrical impedance measurements through a pair of parallel planar electrodes, and/or capacitance measurements. With respect to impedance measuring detectors, the range of cell sizes that needs to be counted and detected determines the spacing between these electrodes. Typically, this spacing should be comparable to or somewhat larger than the cell diameter. For blood cells, the spacing could be 10-20 microns. For bacteria detection the spacing could be 5-10 microns.

Various techniques/methodologies to count and detect the presence of a target species in a sample include measuring electrical conductivity of a buffer solution flowing within the microfluidic channel by passing a small amount of current between the two electrodes. Any rapid spikes in this current (AC or DC) would indicate a fleeting change in the local conductivity of the medium—most likely brought about by the passing of a cell whose electrical conductivity properties are different from the medium. When the gap between the sense electrodes is comparable to the cell size, the disturbance to the electric field pattern between the electrodes is maximized, and the electrical signal to background ratio is optimized.

In some embodiments, detecting and counting cells present in a ferrofluidic solution may be performed by measuring capacitance. The electrode layout and cellular detection mechanism for capacitative sensors is the same as the impedance approach: a pair of electrodes with a gap whose width is comparable to the diameter of the cells of interest. The capacitance measured is typically small and its measurement is generally performed with high frequency AC excitation (>1 MHz, typically) in order to get a capacitance signal. Where the target species to be detected are bacteria, the relative permittivity of such bacteria target species is on the order of 100 and that of ferrofluid will be on the order of 80, so their presence within the ferrofluid can be detected if the cells can be localized close to the sensing electrodes.

Thus, by using a magnetic field generated, for example, using electrode configurations similar to those described in relation to FIGS. 1-16, the target species can be pushed towards the channel ceiling where the sensing electrodes may be located. In some embodiments, the detectors used in conjunction with microfluidic devices and systems include an antibody "carpet" that specifically captures target cells, and a pair of detection capacitors—one upstream and another downstream of the capture carpet. In such a configuration, the sensing capacitors can count the number of cells entering (N_in) and those leaving (N_out) the capture region and determine from the compute difference (i.e., N_in−N_out) how many were captured by the carpet. Alternatively, pairs of electrodes to measure impedance, or some other device to measure some other property representative of the number/amount of individual target species, may be used. The microfluidic systems and devices described herein are implemented to yield over the surface of the antibody carpet a shear flow that is strong enough to prevent non-specific attachment of other cells, but not too strong so as to lead to loss of target cells. In this operational mode, different capture regions may be serially placed downstream of each other and provide quantitative and specific detection capability for multiple target species, e.g., pathogens or other target cells such as CD4+ white blood cells, specific cancer cells that express the epithelial cell adhesion molecule (EpCAM), etc.

The antibody carpet can be realized by a variety of surface functionalization chemistries. The sensing electrodes may be printed, pattern-transferred, or microfabricated (evaporation or sputtering of the metal on a lithographically patterned surface).

Some advantages of the microfluidic channel based detectors include:

Simplifying the manufacturing process by separating the surface functionalization from the actual cell sensor (detector).

Many conventional existing bio-sensors with integrated electronics functionalize the sensor surface directly. With micro- or nano-scale sensors (that purportedly give much higher sensitivities), the total surface area that is functionalized is miniscule. Sometimes, there is space for no more than just a few cells on the sensor surface. Thus, if the target cell concentration is relatively high, a rapid saturation of the sensor signal may ensue. To solve this problem, some conventional devices arrange their sensors in vast arrays (up to thousands), that leads to dramatic increase in system complexity and manufacturability challenges. In the microfluidic-based systems and devices described herein, the detectors used with such systems and devices are capable of detecting as few as a single cell passing through the detection region; the maximum number of cells that can be detected before signal saturation is given by the relative extent of the capture carpet. Increasing the dynamic range of sensors used with the disclosed microfluidic systems and devices may be as simple as increasing the extent of the capture region, without the need to increase the number of sensors.

The detection approach described herein is label-free (i.e., no fluorescent markers or other tags are attached to the cells to enable detection).

The use of current-carrying electrodes below the channel that focus and push the cell stream towards the detection region (or the use of some other magnetic field generation mechanism, for example, one based on permanent magnets) enables using input pressure to provide the flow of the sample of, in some embodiments, less than 1 psi (pounds per square inch) while maintaining a good throughput. In contrast, in conventional cellular manipulation, channels with heights and widths that are comparable to cell diameters (typically 50 microns or less) have to be used, and therefore either the throughput of those devices is low, or very large pressure sources have to be used to push a fast flow through such tiny channels.

Figure 17:
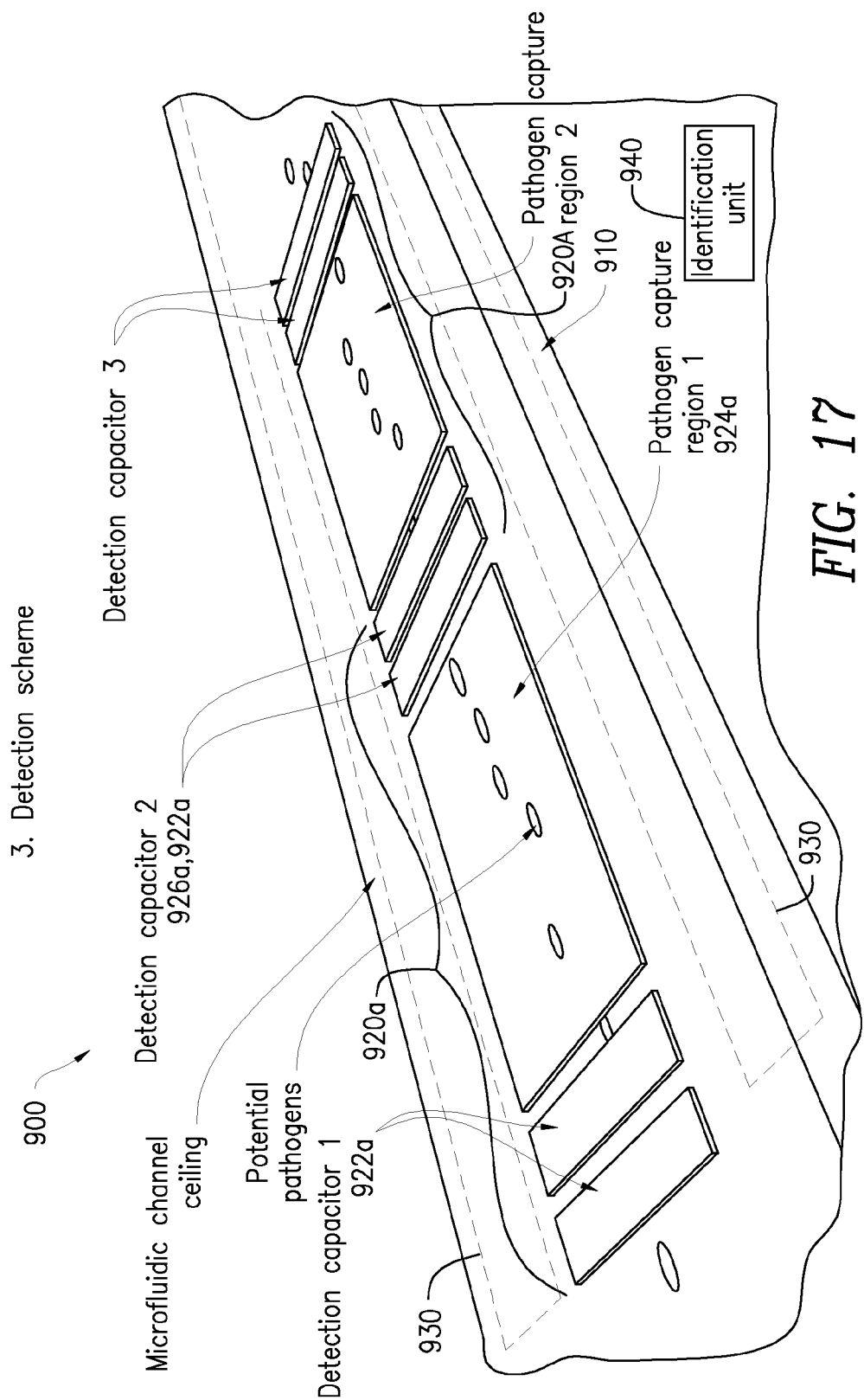
FIG. 17 is a schematic diagram of part of another example embodiment of a microfluidic device.

Thus, with reference to FIG. 17, a schematic diagram of part of an example embodiment of a microfluidic device 900 is shown. The device 900 includes a microfluidic channel 910 which may be similar to the microfluidic channels described in relation to, for example, FIGS. 1A, 4, 5, 13, and/or 14. The device 900 further includes one or more detectors 920a-n, positioned proximate to one side of the channel 910 (in the embodiments depicted, the detectors are positioned on the outside wall of the channel 910 defining the channel's ceiling) that are configured to detect and determine the presence and number of target species in the sample flowing through the microfluidic channel 910, and to also determine the type or identity of the target species so detected. The device 900 also includes a magnetic field generating mechanism to generate a magnetic field that pushes target species in the ferrofluid sample towards the ceiling of the microfluidic channel 910, and thus towards the detectors 920a-n. In some embodiments, the magnetic field generating mechanism may be implemented using a set of electrodes, such as the electrodes 930 (depicted as dashed lines), that may be similar such as those depicted and described in relation to FIGS. 1-17. Such electrodes may have a pre-determined configuration such that when at least one controllable current passes through those electrodes, a controllable magnetic field is generated that pushes the non-magnetic target species (cells, bacteria, etc.) towards the surface of the microfluidic channel opposite the surface that is close to the electrodes.

For example, the electrodes may include at least two electrodes positioned proximate the microfluidic channel that are configured to conduct controllably supplied at least one current and to generate controllable magnetic forces according to, at least in part, physical attributes of the electrode(s), physical attributes of the microfluidic channel, and/or attributes of the current(s) applied. Such physical attributes may include structure of the at least two electrodes, where the structure of the at least two electrodes may include one or more of, for example, a substantially straight shape of one or more of the at least two electrodes, a substantially wiggly shape of the one or more of the at least two electrodes, a substantially parallel arrangement of the at least two electrodes, and/or a substantially tapering orientation of the at least two electrodes in which the at least two electrodes are gradually approaching each other. The electrodes are configured to generate controllable magnetic forces in the sample containing the ferrofluid when at least one controllable electrical current (which may be controlled using a controller such as the controller 160 of FIG. 1A) including associated attributes (e.g., phases, frequency, amplitude, etc.) is applied to the at least two electrodes.

In some implementations, permanent magnets may be used in addition to or instead of the electrodes to facilitate generating the magnetic field to push the target species towards the channel surface closest to the detectors 920a-n.

As noted, and as shown in FIG. 17, in some embodiments capacitance-based detectors, impedance-based detectors, etc., may be used. For example, the detector 920a includes an upstream detection capacitor 922a, comprising two sensing electrode plates, a capture region (also referred to as a carpet area) 924a, and a downstream detection capacitor 926a positioned downstream of the capacitor 922a and the carpet 924 (the downstream detection capacitor 926a also serves as the upstream detection capacitor, marked as 922n) for the next sequential detector used in conjunction with the microfluidic device 900 of FIG. 17.

Figure 18:
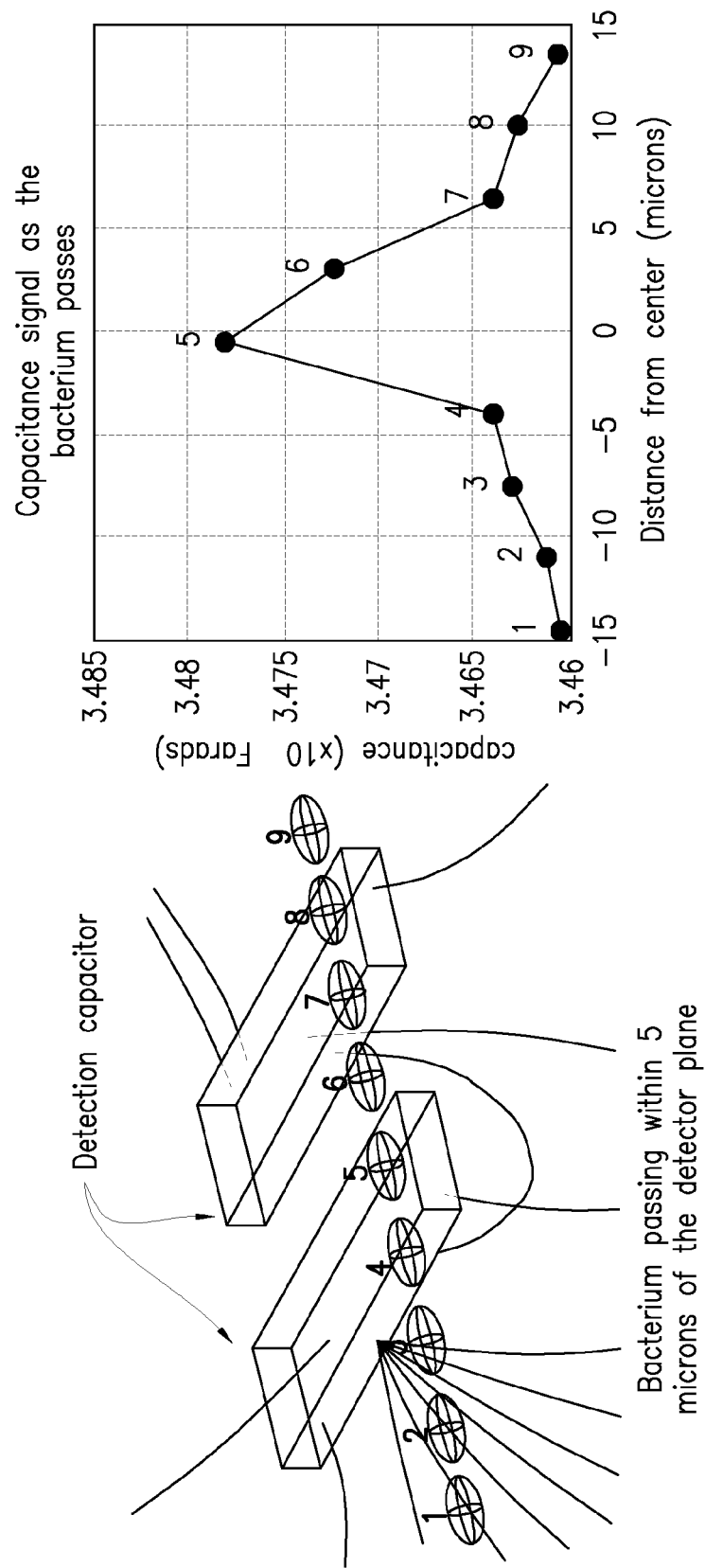
FIG. 18 includes a schematic diagram of a detection capacitor and a graph depicting the change in capacitance as a result of bacteria passing near the detector plane.

The upstream detection capacitor 922a is configured to determine the capacitance resulting from the number (or approximate number) of the target species (such as cells, bacteria, etc.) present in the sample. Based on the capacitance (or impedance) detected, an identification unit 940 (which may be a processor-based computing device) may be used to determine the number (or approximate number) N_in entering the detector. With reference to FIG. 18, a schematic diagram of a detection capacitor and a graph depicting the change in capacitance as a result of bacteria passing near the detector plane is shown. As illustrated in the graph of FIG. 18, the larger the number of passing bacteria (or some other target species), the higher the detected capacitance is.

After determining the number of target species passing by the upstream detection capacitor 922a, the target species flow near the antibody carpet 924a that is functionalize to capture, and thus detect, a particular type of target species (be it a cell or some pathogen). The carpet 924 facilitates obtaining specificity in detection of target species that may have similar size and structure (which makes visual identification, for example with a microscope, more difficult and uncertain). For instance, both *E. coli* and *Salmonella* are rod shaped, with similar size distributions, but these target species can be distinguished using antibodies that are used to functionalize one or more antibody carpets.

As noted, the use of a magnetic field generating mechanism (electrodes or permanent magnet) enables pushing the target species close enough to the carpet 924a so that more efficient capturing capabilities can be realized. Subsequently, the non-capture target species continue to flow and pass by the downstream detection capacitor 926a, which measures the capacitance (or, alternatively, the impedance) resulting from the remaining, non-captured target species, whereupon based on the determined capacitance at the downstream detection capacitor 926a the number of remaining target species (N_out) can be determined (e.g., by the identification unit 940). The different of N_in and N_out can thus yield the number of target species captured by the carpet 924a. In some embodiments, a determination that the individual members of a target species captured indicate the presence of that target species in the sample is made if the difference between N_in and N_out exceeds a pre-determined threshold. Other types of detection mechanisms (e.g., one based on impedance) may be used to similarly determine the number and identity of various target species in the flowing sample.

In some embodiments, a cascade of the target cell detectors of similar (or even different) configurations can be used. For example, in the embodiments depicted in FIG. 17, the first detector 920a is followed by a sequential detector 920b whose carpet region (i.e., capture region) may be configured (by appropriate functionalization) to capture, and thus detect, a different type of target species.

Accordingly, in some embodiments, the detectors used with the microfluidic devices and systems described herein may each include a pair of spaced electrodes to measure capacitance (or impedance) within the microfluidic channel, and an identification unit to determine presence of the at least one target species based on the measured capacitance. The identification unit may be configured to determine the presence of the at least one target based on a change in measured capacitance in the microfluidic channel resulting from the presence of the at least one target species. In some embodiments the detector may be configured to measure other properties that are affected by the presence of target cells, such as impedance, etc. Each detector may further include a capture region including a substance configured to interact with one of a plurality of target species, with the capture region being located in the microfluidic channel downstream of the pair of spaced electrodes, and another pair of spaced electrodes located downstream of the capture region to measure capacitance (or impedance) within the microfluidic channel.

As noted, in some implementations, the identification unit is configured to determine an initial number of at least one target species at the pair of spaced electrodes and an end number of the at least one target species at the other pair of spaced electrodes, and to determine based, at least in part, on the difference between the initial and end numbers whether a level of the at least one target species captured by the capture region exceeds a pre-determined threshold.

As further described, in some embodiments, the detector comprises a cascade of sequentially positioned detection sets, with each of the cascade of the sequentially positioned detection sets including a first pair of spaced electrodes to measure capacitance (or impedance) within the microfluidic channel, a capture region including a substance configured to interact with one of a plurality of target species, with the capture region located downstream of the first pair of spaced electrodes. The each of the cascade of the sequentially positioned detection sets also includes a second pair of spaced electrodes located downstream of the capture region to measure capacitance (or impedance) within the microfluidic channel, and an identification unit to determine at each of the detection sets an initial number of at least one target species at the first pair of spaced electrodes and an end number of the at least one target species at the second pair of spaced electrodes, and to determine based, at least in part, on the difference between the initial and end numbers whether a level of the at least one target species captured by the capture region exceeds a pre-determined threshold.

Figure 19:
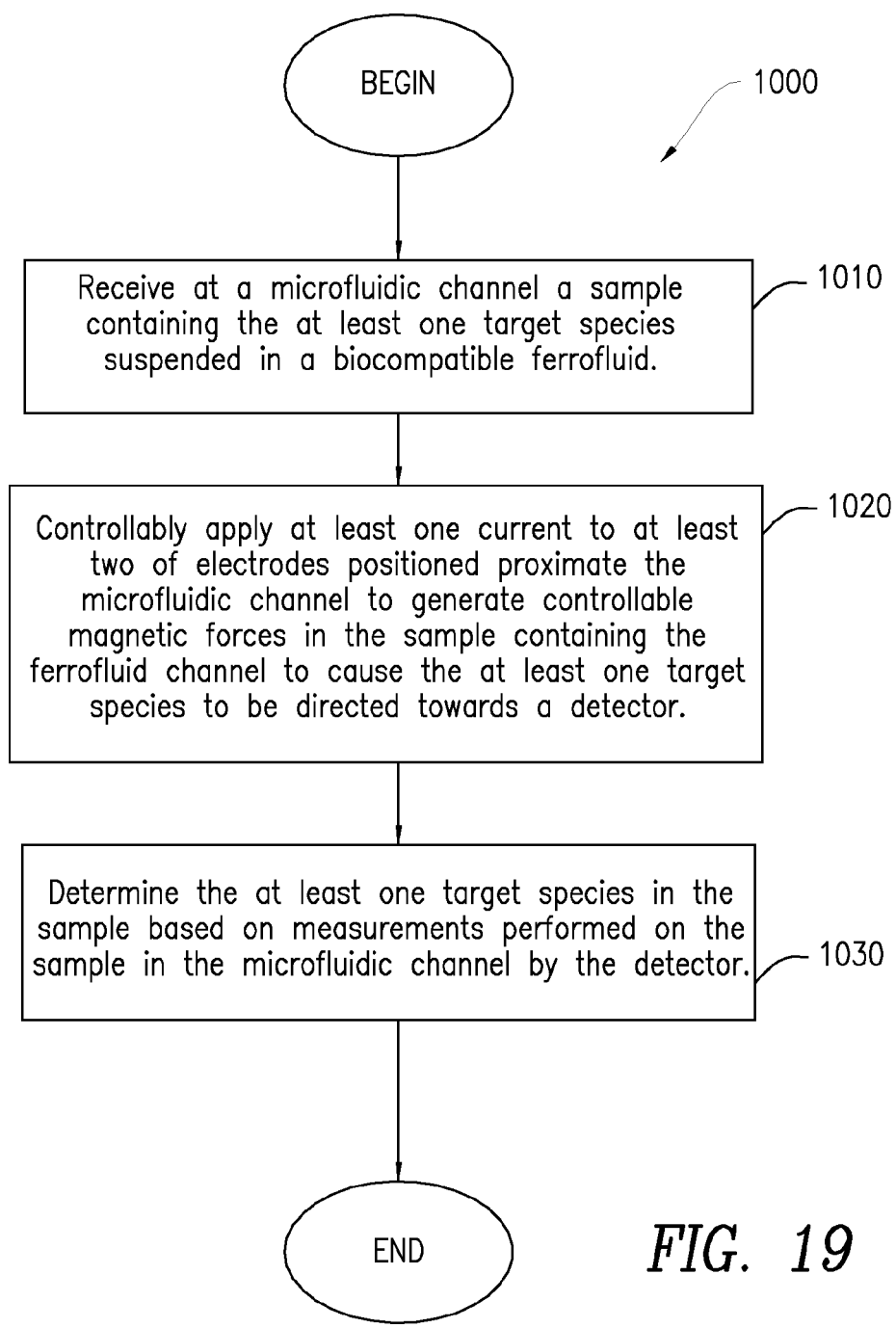
FIG. 19 is a flowchart of an example procedure to detect at least one target species in a sample.

With reference now to FIG. 19, a flowchart of an example procedure 1000 to detect at least one target species in a sample is shown. The method includes receiving 1010 at a microfluidic channel (such as the one depicted in FIGS. 1A, 4, 5, 13, 14, and 17) a sample containing the at least one target species (e.g., cells, bacteria, non-organism species, etc.) suspended in a biocompatible ferrofluid such as those described herein.

Having received the sample, at least one current is controllably applied 1020 (e.g., using a controller, such as a processor-based controller, manually controlling, etc.) to at least two of electrodes (or even to just a single electrode) positioned proximate the microfluidic channel to generate controllable magnetic forces in the sample containing the ferrofluid channel to cause the at least one target species to be directed towards a detector. The electrodes may be any of the electrode configurations described herein in relation to, for example, FIGS. 1-18. In some embodiments, the detector may be a detector based on capacitance measurements, or one based on measuring other properties (e.g., impedance) of the sample containing the target species. Such a detector may enable determining the number (or amount) of target species at an input and output stages to a capture region (e.g., a carpet functionalized with a particular antibody configured to interact with a particular target species that may be present in the sample). The difference between the number of target species measure at the input and output stages may be indicative of the number of target species members (e.g., individual organisms) captured by the capture region that was configured (e.g., functionalized) to capture that particular target species type. Thus, based on measurements performed on the sample in the microfluidic channel by the detector, the at least one target species in the sample is determined 1030.

Figure 20:
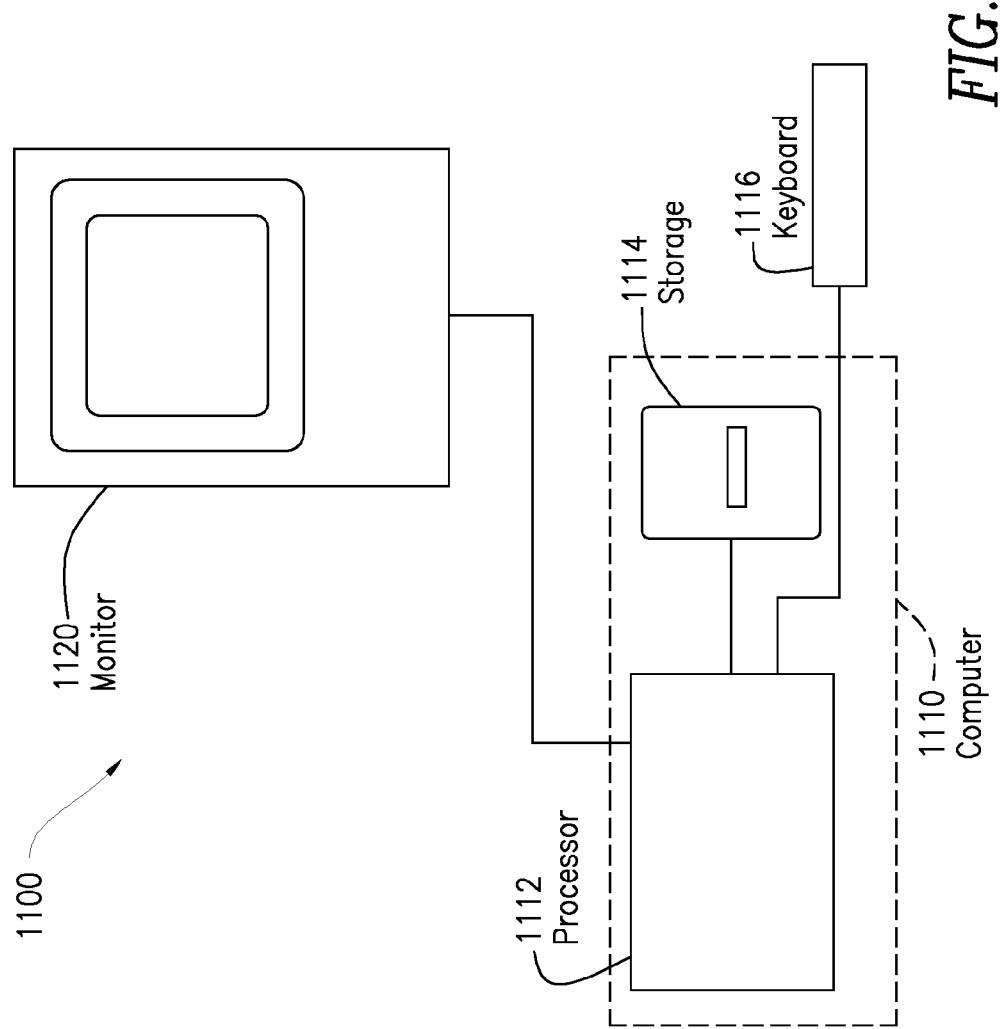
FIG. 20 is a schematic diagram of a generic computing system.

With reference now to FIG. 20, a schematic diagram of a generic computing system 1100 that may be used to implement any of the processor-based systems/device that may be used in conjunction with the systems and devices described herein, including the controller 160 of FIG. 1A, the identification unit 940 of FIG. 17, etc., is shown. The computing system 1100 includes a processor-based device 1110 such as a personal computer, a specialized computing device, and so forth, that typically includes a central processor unit 1112. In addition to the CPU 1112, the system includes main memory, cache memory and bus interface circuits (not shown). The processor-based device 1110 includes a mass storage element 1114, such as a hard drive associated with the computer system. The computing system 1100 may further include a keyboard, or keypad, 1116, and a monitor 1120, e.g., a CRT (cathode ray tube) or LCD (liquid crystal display) monitor.

The processor-based device 1110 is configured to facilitate, for example, the control and processing operations described herein, e.g., determining and/or controlling at least one controllable current applied to electrode(s) to generate controllable magnetic field, determining the number/amount of target species based on properties detected (e.g., capacitance, impedance), etc. The storage device 1114 may thus also include a computer program product that when executed on the processor-based device 1110 causes the processor-based device to perform operations to facilitate the implementation of the controlling and/or processing operations described herein. The processor-based device may further include peripheral devices to enable input/output functionality. Such peripheral devices may include, for example, a CD-ROM drive and/or flash drive, or a network connection, for downloading related content to the connected system. Such peripheral devices may also be used for downloading software containing computer instructions to enable general operation of the respective system/device. Alternatively and/or additionally, in some embodiments, special purpose logic circuitry, e.g., an FPGA (field programmable gate array) or an ASIC (application-specific integrated circuit) may be used in the implementation of the system 1100. Other modules that may be included with the processor-based device 1110 are speakers, a sound card, a pointing device, e.g., a mouse or a trackball, by which the user can provide input to the computing system 1100. The processor-based device 1110 may include an operating system, e.g., Windows XP® Microsoft Corporation operating system. Alternatively, other operating systems could be used.

Moreover, the various illustrative logical blocks, modules, and methods described in connection with the embodiments disclosed herein can be implemented or performed with a general purpose processor, a digital signal processor ("DSP"), or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

Computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a non-transitory machine-readable medium that receives machine instructions as a machine-readable signal.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

Some or all of the subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an embodiment of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server generally arises by virtue of computer programs running on the respective computers and having a client-server relationship to each other.

The various illustrative logical blocks, modules, circuits, and methods described in connection with the above described figures and the embodiments disclosed herein can often be implemented as electronic hardware, computer software, or combinations of both.

Additionally, the methods/procedures described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such that the processor can read information from, and write information to, the storage medium. In the alternative, the storage medium can be integral to the processor. The processor and the storage medium can also reside in an ASIC.

A number of implementations of the invention have been described. Nevertheless, it will be understood that various modifications may be made without departing from the spirit and scope of the invention. Accordingly, other embodiments are within the scope of the following claims.

APPENDIX A—CALCULATION FOR PARTICLE MANIPULATION

Provided herein is an analytical approach that enables the estimation of particle velocities and critical frequencies observed in the ferromicrofluidic systems, devices and methods described herein. To simplify the calculations, a perfectly spherical, incompressible microparticle, a magnetically linear ferrofluid, and a slip factor (see below) that is independent of field magnitude and frequency are assumed. Further assumed is that the spherical particle radius (R) is small compared to the wavelength of the travelling magnetic field ($\vec{H}$) as determined by electrode dimensions and spacing, so that $R|\nabla \vec{H}| \ll |\vec{H}|$ holds true. Under these assumptions, the ferrofluid magnetization in the immediate vicinity of the microparticle—and, the virtual magnetization $M_{eff}$ within the particle's volume $V_p$—can be approximated as uniform. It is also approximated that any field value (but not its gradient) is constant within the interior extent of the microparticle.

The total instantaneous force on that dipole is then given by $$\vec{F}_{ins} = \int_{V_p} \nabla\left(\vec{M}_{eff} \cdot \vec{B}_{in}\right) dV \quad \text{(Equation A)}$$

where $B_{in}$ is the magnetic flux density within the spherical microparticle and the integration is over the internal volume of the particle (Zahn et al., 1995, *J of Magnetism and Magnetic Materials* 149:165-173). Under these assumptions, the surface terms in Equation A due to discontinuities in M and B create pressure terms that integrate out to 0, and a simple vector expansion of the integrand reveals that this term is the same as the Kelvin force density. Thus, the instantaneous force expression can be simplified to $$\vec{F}_{ins} = V_p \nabla(\vec{M}_{eff} \cdot \vec{B}_{in}) \quad \text{(Equation B)}$$

To obtain an eventual analytical expression for the magnetic force, it is helpful to express $M_{eff}$ and $B_{in}$ in terms of the external magnetic field ($H_{ext}$) in the absence of the microparticle, since this field value can be easily obtained from simple simulations. The net magnetization of the particle with a magnetic permeability $\mu_p$ (essentially $\mu_0$) within the ferrofluid (with a complex, frequency-dependent permeability $\mu_f = \mu_0(1+\chi_f)$ depends on $H_{ext}$ as follows $$\vec{M}_{eff} = 3\left(\frac{\mu_p - \mu_f}{\mu_p + 2\mu_f}\right)\vec{H}_{ext} \Rightarrow \vec{M}_{eff} = \frac{-3\chi_f}{3 + 2\chi_f}\vec{H}_{ext} \quad \text{(Equation C)}$$

Determining the magnetic flux density and field within the particle requires consideration of the demagnetization field inside it. The overall field inside the particle is $\vec{H}_{in} = \vec{H}_{ext} - \vec{H}_{dmag}$, with $\vec{H}_{dmag} = \vec{M}_{eff}/3$, for a sphere. Hence, in the linear regime where particle magnetization can be written $\vec{M}_{eff} = \chi_{eff}\vec{H}_{in}$, one finds $$\frac{\vec{M}_{eff}}{\chi_{eff}} = \vec{H}_{ext} - \frac{\vec{M}_{eff}}{3} \Rightarrow \vec{M}_{eff} = \left(\frac{3\chi_{eff}}{3 + \chi_{eff}}\right)\vec{H}_{ext} \quad \text{(Equation D)}$$

Comparing Equations C and D reveals the effective susceptibility of the particle in terms of the ferrofluid susceptibility:

$$\chi_{eff} = \frac{-\chi_f}{1 + \chi_f} \quad \text{(Equation E)}$$

It is to be noted that the effective magnetic susceptibility depends on that of the ferrofluid, since the microparticle responds to magnetic forces only because it displaces ferrofluid and creates a "magnetic hole." In that regard, the magnetic medium in which the hole resides determines the strength of the interactions between that magnetic hole and applied fields. The negative sign in Equation E indicates that the effective magnetization of the microparticle is in the opposite direction of the local ferrofluid magnetization under static conditions. While for $\chi_{eff} \approx \chi_f$ for $\chi_f \ll 1$, the effective susceptibility of the magnetic hole approaches −1 in a strongly magnetisable medium. In effect, using too strong a ferrofluid for microparticle manipulation could be counter-productive.

The instantaneous magnetic force on the particle can be expressed as $$\vec{F}_{ins} = V_p \nabla\left(\vec{M}_{eff} \cdot \vec{B}_{in}\right) = V_p \mu_0 \vec{\nabla}\left(\vec{M}_{eff} \cdot (\vec{H}_{in} + \vec{M}_{eff})\right) = \quad \text{(Equation F)}$$

$$V_p \mu_0 \vec{\nabla}\left(\vec{M}_{eff} \cdot \vec{H}_{in} + |\vec{M}_{eff}|^2\right) =$$

$$V_p \mu_0 \vec{\nabla}\left(|\vec{M}_{eff}|\frac{|\vec{M}_{eff}|}{\chi_{eff}}\cos\theta + |\vec{M}_{eff}|^2\right) =$$

$$V_p \mu_0 \vec{\nabla}\left(|\vec{M}_{eff}|^2 \frac{\mathrm{Re}\{\chi_{eff}\}}{|\chi_{eff}|^2} + |\vec{M}_{eff}|^2\right)$$

Here, $\theta$ is the angle between $\vec{M}_{eff}$ and $\vec{H}_{in}$, given by the angle of the complex susceptibility $\chi_{eff}$. Using $$\vec{M}_{eff} = 3\left(\frac{-\chi_f}{3 + 2\chi_f}\right)\vec{H}_{ext},$$

we get $$\vec{F}_{ins} = V_p \mu_0 \left(\frac{\mathrm{Re}\{\chi_{eff}\}}{|\chi_{eff}|^2} + 1\right)\left(\frac{9|\chi_f|^2}{9 + 6\mathrm{Re}\{\chi_f\} + 4|\chi_f|^2}\right)\vec{\nabla}|\vec{H}_{ext}|^2 \quad \text{(Equation G)}$$

In the presence of traveling fields, the local magnetic field varies sinusoidally, and the time-average force is just half the maximum value of the instantaneous force:

$$\vec{F}_{ave} = \quad \text{(Equation H)}$$

$$\frac{1}{2}V_p \mu_0 \left(\frac{\mathrm{Re}\{\chi_{eff}\}}{|\chi_{eff}|^2} + 1\right)\left(\frac{9|\chi_f|^2}{9 + 6\mathrm{Re}\{\chi_f\} + 4|\chi_f|^2}\right)\vec{\nabla}|\vec{H}_{ext}|^2$$

Similarly, the instantaneous torque on a magnetic dipole is given by $$\vec{\tau}_{ins} = s\int_{V_p}\left(\vec{M}_{eff} \times \vec{B}_{in}\right)dV = sV_p\left(\vec{M}_{eff} \times \vec{B}_{in}\right). \quad \text{(Equation I)}$$

(Zahn et al., 1995, *J of Magnetism and Magnetic Materials* 149:165-173). Here, the possibility that the rotation of the nonmagnetic microparticle may be subject to a slip s between 0 and 1 has been allowed for, This slip factor represents the ratio of the torque that a non-magnetic microparticle experiences in the ferro-microfluidic systems and devices described herein to the value of the torque that would be felt by an isolated particle of the same size and effective magnetization.

The remaining details of the derivation for magnetic torque mirror those for magnetic force. Substituting for the magnetic flux density, one obtains $$\vec{\tau}_{ins} = sV_p\left(\vec{M}_{eff} \times \vec{B}_{in}\right) = sV_p\mu_0\left(\vec{M}_{eff} \times (\vec{H}_{in} + \vec{M}_{eff})\right) = \quad \text{(Equation J)}$$

$$sV_p\mu_0\left(\vec{M}_{eff} \times \vec{H}_{in} \times \vec{M}_{eff} \times \vec{M}_{eff}\right)$$

Since $\vec{M}_{eff} \times \vec{M}_{eff} = 0$ and $\vec{M}_{eff} = \chi_{eff}\vec{H}_{in}$, one gets $$\vec{\tau}_{ins} = \hat{y}sV_p\mu_0\left(|\vec{M}_{eff}||\vec{M}_{eff}|\frac{|\chi_{eff}|}{|\chi_{eff}|^2}\sin\theta\right) = \quad \text{(Equation K)}$$

$$\hat{y} s V_p \mu_0 \frac{\text{Im}\{\chi_{eff}\}}{|\chi_{eff}|^2} \left( \frac{9|\chi_f|^2}{9+6\text{Re}\{\chi_f\}+4|\chi_f|^2} \right) |\vec{H}_{ext}|^2$$

And time average torque is given by $$\vec{\tau}_{ave} = \hat{y} \frac{V_p}{2} s \mu_0 \frac{\text{Im}\{\chi_{eff}\}}{|\chi_{eff}|^2} \left( \frac{9|\chi_f|^2}{9+6\text{Re}\{\chi_f\}+4|\chi_f|^2} \right) |\vec{H}_{ext}|^2. \quad \text{(Equation L)}$$

A finite element analysis program (COMSOL) was used to calculate $H_{ext}$ for given input current amplitude using a realistic, two-dimensional cross-section of the ferromicrofluidic channel and the electrodes underneath. The Reynolds' number associated with the motion of micron-scale beads and cells in a quiescent ferrofluid is very small. In this regime, inertial effects can be neglected and Stokes flow equations dominate hydrodynamics. Hence, the equilibrium between viscous drag and magnetic forces determine microparticle dynamics. Because Stokes flow equations are linear, all hydrodynamic coefficients involved can be combined into a resistance matrix:

$$\begin{bmatrix} F_{ave,x} \\ \tau_{ave,y} \end{bmatrix} = A \begin{bmatrix} v_x \\ \omega_y \end{bmatrix}, \quad \text{(Equation M)}$$

$$\text{with } A = \begin{pmatrix} 6\pi\eta R f_1(h, R) & 6\pi\eta R^2 f_2(h, R) \\ 8\pi\eta R^2 f_3(h, R) & 8\pi\eta R^3 f_4(h, R) \end{pmatrix}$$

(Happel J, Brenner 1-1 (1983) Low Reynolds Number Hydrodynamics with special applications to particulate media. (Martinus Nijhoff: Dordrecht)). Here, v is the linear velocity of the microparticle along the channel length, ω is its angular velocity, η is the ferrofluid viscosity, R is microsphere radius, and $f_i$ is a resistance factor that depends on particle radius and its distance (h) from the channel ceiling. Assuming h<<<R, these resistance factors can be obtained from standard lubrication theory as $$f_1 \approx -\frac{8}{15} \ln(h/R) + 0.9588; \quad \text{(Equaion N)}$$

$$f_2 \approx -\frac{2}{15} \ln(h/R) - 0.2526$$

$$f_3 \approx -\frac{1}{10} \ln(h/R) - 0.1895;$$

$$f_4 \approx -\frac{2}{5} \ln(h/R) + 0.3817.$$

(Goldman et al., 1967, *Chem Eng Sci* 22:637-651) In general, it is possible to estimate It through Dedaguin, Landau, Verwey and Overbeek theory (DLVO theory) (Ise, 2007, *Proc Jpn Acad B Phys. Mal Sci* 83; 192-198) using the surface charge density on the microparticle and the channel surfaces, given the ionic conditions within the ferrofluid. Interestingly, the vertical force ($F_{avg, y}$) that pushes the microparticles up to the channel ceiling is on the order of nN's and they are expected to be close to touching the channel wall.

Equation M can be solved for v and ω through a simple matrix inversion, $$\begin{bmatrix} v_x \\ \omega_y \end{bmatrix} = A^{-1} \begin{bmatrix} F_{ave,x} \\ \tau_{ave,y} \end{bmatrix} \quad \text{(Equation O)}$$

$$A^{-1} = \frac{\begin{pmatrix} 8\pi\eta R^3 f_4(h, R) & -6\pi\eta R^2 f_2(h, R) \\ -8\pi\eta R^2 f_3(h, R) & 6\pi\eta R f_1(h, R) \end{pmatrix}}{48\pi^2 \eta^2 R^4 G} \quad \text{(Equation P)}$$

Here, $G = f_1 f_4 - f_2 f_3$ has been defined for notational convenience. Hence, particle linear velocities due to magnetic force and torque alone can be determined:

$$v_{force,x} = \frac{f_4}{6\pi\eta RG} F_{ave,x} \quad \text{(Equations Q and R)}$$

$$v_{torque,x} = -\frac{sf_2}{8\pi\eta R^2 G} \tau_{ave,y}.$$

Net particle velocity is then given by $$v_x = v_{force,x} + v_{torque,x}* \quad \text{(Equation S)}$$

Both magnetic force and torque scale with particle volume ($R^3$); from Equations Q and R, it is clear that particle velocity due to magnetic force depends on $R^2$, whereas that due to torque scales with R. This observation indicates that torque effects on smaller particles is relatively more significant, and explains why smaller microparticles display smaller critical frequencies in their dynamics.

The preceding theoretical approach explains the experimental results very well (e.g., FIG. 10A) for a slip factor of 1 and h of about 1 nm, confirming the expectation that the microparticles are indeed pushed strongly towards the channel ceiling. The slip factor of 1 implies that the microspheres rotate under no-slip conditions.

APPENDIX B—FORCE ON A MAGNETIC DIPOLE

In general, the magnetic force on a magnetic dipole can be found using the Kelvin force expression, i.e., $$\vec{F} = \mu_0 \int_{V_p} (\vec{M} \cdot \nabla) \vec{H} \, dV \quad \text{(Equation T)}$$

This expression is approximately equivalent to Equation A presented in Appendix A. A key assumption is that the applied field is not too inhomogeneous and the particle radius (R) is small enough, such that $R|\nabla \vec{H}| << |\vec{H}|$ in any direction. Under this assumption, the magnetization of the ferrofluid immediately surrounding the microparticle can be taken as uniform. It is further approximated that any field value (but not its gradient) is constant within the interior extent of the microparticle.

With these simplifying assumptions in mind, vector identities can be used to rewrite the integrand of Equation A as follows:

$$\nabla(\vec{M} \cdot \vec{B}) = \vec{M} \times (\nabla \times \vec{B}) + \vec{B} \times (\nabla \times \vec{M}) + (\vec{M} \cdot \nabla)\vec{B} + (\vec{B} \cdot \nabla)\vec{M}. \quad \text{(Equation U)}$$

The first term on the right-hand-side (RHS) of Equation U involves the curl of the magnetic flux density, which could be expanded as $$\vec{M} \times (\nabla \times \vec{B}) = \vec{M} \times (\nabla \times \vec{H}) + \vec{M} \times (\nabla \times \vec{M}) \quad \text{(Equation V)}$$

The curl of the magnetic field is 0 everywhere within the integration volume of Equation A, since both the ferrofluid and the plastic microparticle are insulating and do not support electrical currents. Thus, the first term on the RHS of Equation V vanishes. The curl of the magnetization is 0 inside the microparticle, but across its surface, the effective magnetization changes as a step. Therefore, surface contributions to the force density should, in general, be considered. However, since the magnetization of the ferrofluid immediately surrounding the microparticle is assumed to be constant, the second term of Equation V also vanishes when integrated around a sphere (due to symmetry). The same logic could be applied to the $\vec{B} \times (\nabla \times \vec{M})$ term in Equation U: $(\nabla \times \vec{M})$ is 0 inside the microsphere and $\vec{B} \times (\nabla \times \vec{M})$ integrates to 0 around the sphere surface with the magnetic flux density and ferrofluid magnetization assumed constant in the immediate vicinity of the microsphere.

With the same reasoning, the $(\vec{B} \cdot \nabla)\vec{M}$ term in Equation U will also be 0 inside the microsphere and integrate to 0 around it. The only term that involves the non-zero gradient of a field vector then is $$\vec{F} = \int_{V_p} (\vec{M} \cdot \nabla)\vec{B} \, dV. \quad \text{(Equation W)}$$

The integral is valid over the volume of the microparticle, which is nonmagnetic. Hence, inside the microparticle, $\vec{B} = \mu_0 \vec{H}$ and Equation W becomes the same as Equation T. In other words, under the assumptions outlined above, Equations A and T are equivalent in the case of the setup presented herein.

Equation A may be used as the force expression instead of that in Equation T, since the former leads to a force whose direction is determined by the gradient operator requiring taking a single derivative along a given spatial direction to determine the force along that direction.

Also considered is what happens to surface gradients associated with the expression in Equation A. Once again, using the assumption that the ferrofluid magnetization and the magnetic flux density are constant inside and just around the microsphere surface (but not their derivatives), it can be determined that $$F_x = \int_{V_p} \frac{\partial}{\partial x} (\vec{M} \cdot \vec{B}) dV = \int_{V_p} \frac{\partial}{\partial x} (M_x B_x + M_z B_z) dV \quad \text{(Equation X)}$$

Here, the field and magnetization vectors are taken to be in the x-z plane due to the symmetry of the ferro-microfluidic channel. As previously described, the expression in Equation X is evaluated only within the interior of the microparticle to calculate the x-directed force. Without any loss of generality, the microsphere center is taken as the origin. Both $\vec{M}$ and $\vec{B}$ are discontinuous at the particle-ferrofluid boundary, so their derivatives result in an impulse; when integrated across the microsphere surface, each contribution $M_{x,out}B_{x,out} - M_{z,in}B_{z,in}$ to the integral from a surface patch at $x=\sqrt{(R^2-y^2-z^2)}$ gets cancelled out by the negative of that contribution at the opposite patch at $x=-\sqrt{(R^2-y^2-z^2)}$ The resulting surface integral is 0. By spherical symmetry, the same is true for the terms in $F_z$. Hence, under the described assumptions, evaluating Equation A within the interior of the microparticle yields the magnetic force on it.

What is claimed is:

1. A device to focus at least one target species suspended in a biocompatible ferrofluid, the device comprising:
    a microfluidic channel configured to receive a sample containing the at least one target species and the biocompatible ferrofluid, the at least one target species in the received sample being substantially concentrated in an input flow with an associated input width; and
    at least two of electrodes positioned proximate the microfluidic channel, the at least two electrodes configured to generate controllable magnetic forces in the sample containing the ferrofluid when controllable electrical currents are applied to the at least two electrodes, the generated controllable magnetic forces substantially parallel to each other and a longitudinal axis of the microfluidic channel, the generated controllable magnetic forces causing the at least one target species to be focused in a resultant flow having a width narrower than the input width associated with the input flow.

2. The device of claim 1, wherein the at least two electrodes positioned proximate the microfluidic channel are configured to conduct controllably supplied currents and to generate the controllable magnetic forces according to, at least in part, physical attributes of the at least two electrodes.

3. The device of claim 1 further comprising:
    a power source configured to apply the controllable electrical currents to the at least two electrodes to controllably generate the controllable magnetic forces.

4. The device of claim 3, wherein the power source is configured to apply current with one or more of a selected amplitude, a selected frequency, and a selected phase.

5. The device of claim 4, wherein focusing of the at least one target species is based, at least in part, on the one or more of the selected amplitude, the selected frequency, and the selected phase of the current.

6. The device of claim 1, wherein the at least two electrodes are configured to cause the at least one target species to focus in a direction substantially parallel to the microfluidic channel.

7. The device of claim 1 further comprising:
    a flow generation unit including at least one of: a pressure pump, a syringe pump, a peristaltic pump, a vacuum device, a structure enabling flow via gravity, and a device to generate capillary forces.

8. The device of claim 1, wherein the sample comprises cell-based species.

9. The device of claim 1, wherein the biocompatible ferrofluid comprises a suitable amount of ionic species to control the osmotic pressure on the cells to promote cell sustainability.

10. The device of claim 1, wherein the biocompatible ferrofluid comprises a citrate concentration of between about 5-200 mM.

11. The device of claim 1, wherein one or more walls of the microfluidic channel length include a pocketed, a ridged, a grooved, a trenched, or a sloped region.

12. The device of claim 1, wherein the sample includes living cells.

13. The device of claim 1, wherein one or more walls of the microfluidic channel includes one or more contours.

14. The device of claim 1, wherein the at least one of the at least two electrodes comprises an electrode layer.

\* \* \* \* \*